United States Patent
Muhsin et al.

(10) Patent No.: US 11,298,021 B2
(45) Date of Patent: Apr. 12, 2022

(54) MEDICAL MONITORING SYSTEM

(71) Applicant: MASIMO CORPORATION, Irvine, CA (US)

(72) Inventors: Bilal Muhsin, San Clemente, CA (US); Omar Ahmed, Lake Forest, CA (US); Massi Joe E. Kiani, Laguna Niguel, CA (US); Keith Ward Indorf, Riverside, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 16/164,576

(22) Filed: Oct. 18, 2018

(65) Prior Publication Data

US 2019/0117070 A1 Apr. 25, 2019

Related U.S. Application Data

(60) Provisional application No. 62/745,270, filed on Oct. 12, 2018, provisional application No. 62/683,579, (Continued)

(51) Int. Cl.
*A61B 5/00* (2006.01)
*A61B 5/021* (2006.01)
(Continued)

(52) U.S. Cl.
CPC ............ *A61B 5/0022* (2013.01); *A61B 5/022* (2013.01); *A61B 5/0295* (2013.01); (Continued)

(58) Field of Classification Search
CPC ... A61B 5/0022; A61B 5/02141; A61B 5/022; A61B 5/746; A61B 5/7465; (Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

NL 8801322 12/1989
WO WO 2017/114951 7/2017
WO WO 2019/079643 4/2019

OTHER PUBLICATIONS

International Search Report and Written Opinion for International Application No. PCT/US2018/056579, dated Mar. 18, 2019, in 23 pages.
(Continued)

*Primary Examiner* — Amanda K Hulbert
(74) *Attorney, Agent, or Firm* — Knobbe, Martens, Olson & Bear, LLP

(57) ABSTRACT

The present disclosure includes a host device that is part of a patient monitoring system. The host device can provide an improved, organized, uncluttered, and graphically-rich display that presents an integrated display of real-time patient data and alarms from multiple integrated or non-integrated devices, such as patient monitors, ventilators, anesthesia gas machines, or intravenous (IV) pumps. The host device may provide a supplementary display for the patient data collected by the multiple devices and present information, such as comprehensive real-time patient status, historical trends, or alarm indicators, in an organized manner for particular clinical scenarios. The one or more displays can be central to a care team for a patient, and the care team can together simultaneously view and act upon the information presented.

20 Claims, 73 Drawing Sheets

Related U.S. Application Data filed on Jun. 11, 2018, provisional application No. 62/574,726, filed on Oct. 19, 2017.

(51) Int. Cl.
*A61B 5/022* (2006.01)
*A61B 5/0295* (2006.01)
*A61B 5/08* (2006.01)
*A61B 5/1455* (2006.01)
*A61B 5/0205* (2006.01)
*A61B 5/01* (2006.01)
*A61B 5/369* (2021.01)
*G16H 40/60* (2018.01)
*A61B 5/145* (2006.01)

(52) U.S. Cl.
CPC .......... *A61B 5/02141* (2013.01); *A61B 5/746* (2013.01); *A61B 5/7425* (2013.01); *A61B 5/7465* (2013.01); *A61B 5/0006* (2013.01); *A61B 5/01* (2013.01); *A61B 5/0205* (2013.01); *A61B 5/08* (2013.01); *A61B 5/14542* (2013.01); *A61B 5/14553* (2013.01); *A61B 5/369* (2021.01); *A61B 5/4821* (2013.01); *G16H 40/60* (2018.01)

(58) Field of Classification Search
CPC ....... A61B 5/0006; A61B 5/01; A61B 5/0205; A61B 5/04787; A61B 5/08; A61B 5/14542; A61B 5/14553; A61B 5/4821; A61B 5/0295; A61B 5/369; A61B 5/7425; G16H 40/60; G16H 40/67
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |

(56) References Cited

U.S. PATENT DOCUMENTS

| | | |
|---|---|---|
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |

(56) References Cited

U.S. PATENT DOCUMENTS

| | | |
|---|---|---|
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |

(56) References Cited

U.S. PATENT DOCUMENTS

| | | |
|---|---|---|
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,932,217 B2 * | 1/2015 | Gibson ............ A61B 5/7275 600/301 |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |

(56) References Cited

U.S. PATENT DOCUMENTS

| | | |
|---|---|---|
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,512,436 B2 | 12/2019 | Muhsin et al. |
| 10,524,738 B2 | 1/2020 | Olsen |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,548,561 B2 | 2/2020 | Telfort et al. |
| 10,555,678 B2 | 2/2020 | Dalvi et al. |
| 10,568,514 B2 | 2/2020 | Wojtczuk et al. |

(56) References Cited

U.S. PATENT DOCUMENTS

| | | | |
|---|---|---|---|
| 10,568,553 B2 | 2/2020 | O'Neil et al. | |
| RE47,882 E | 3/2020 | Al-Ali | |
| 10,575,779 B2 | 3/2020 | Poeze et al. | |
| 10,608,817 B2 | 3/2020 | Haider et al. | |
| D880,477 S | 4/2020 | Forrest et al. | |
| 10,617,302 B2 | 4/2020 | Al-Ali et al. | |
| 10,617,335 B2 | 4/2020 | Al-Ali et al. | |
| 10,637,181 B2 | 4/2020 | Al-Ali et al. | |
| D887,548 S | 6/2020 | Abdul-Hafiz et al. | |
| D887,549 S | 6/2020 | Abdul-Hafiz et al. | |
| 10,667,764 B2 | 6/2020 | Ahmed et al. | |
| 2001/0034477 A1 | 10/2001 | Mansfield et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0133080 A1 | 9/2002 | Apruzzese et al. | |
| 2003/0013975 A1 | 1/2003 | Kiani | |
| 2003/0018243 A1 | 1/2003 | Gerhardt et al. | |
| 2003/0144582 A1 | 7/2003 | Cohen et al. | |
| 2003/0156288 A1 | 8/2003 | Barnum et al. | |
| 2003/0212312 A1 | 11/2003 | Coffin, IV et al. | |
| 2004/0106163 A1 | 6/2004 | Workman, Jr. et al. | |
| 2005/0055276 A1 | 3/2005 | Kiani et al. | |
| 2005/0234317 A1 | 10/2005 | Kiani | |
| 2006/0073719 A1 | 4/2006 | Kiani | |
| 2006/0161054 A1 | 7/2006 | Reuss et al. | |
| 2006/0189871 A1 | 8/2006 | Al-Ali et al. | |
| 2007/0073116 A1 | 3/2007 | Kiani et al. | |
| 2007/0180140 A1 | 8/2007 | Welch et al. | |
| 2007/0244377 A1 | 10/2007 | Cozad et al. | |
| 2007/0282478 A1 | 12/2007 | Al-Ali et al. | |
| 2008/0064965 A1 | 3/2008 | Jay et al. | |
| 2008/0094228 A1 | 4/2008 | Welch et al. | |
| 2008/0221418 A1 | 9/2008 | Al-Ali et al. | |
| 2009/0024008 A1 | 1/2009 | Brunner | |
| 2009/0036759 A1 | 2/2009 | Ault et al. | |
| 2009/0055735 A1* | 2/2009 | Zaleski | G16H 40/63 715/700 |
| 2009/0093687 A1 | 4/2009 | Telfort et al. | |
| 2009/0095926 A1 | 4/2009 | MacNeish, III | |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2010/0004518 A1 | 1/2010 | Vo et al. | |
| 2010/0030040 A1 | 2/2010 | Poeze et al. | |
| 2010/0099964 A1 | 4/2010 | O'Reilly et al. | |
| 2010/0234718 A1 | 9/2010 | Sampath et al. | |
| 2010/0256456 A1 | 10/2010 | Natarajan | |
| 2010/0270257 A1 | 10/2010 | Wachman et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0071420 A1* | 3/2011 | St. Pierre | A61B 5/7445 600/549 |
| 2011/0082711 A1 | 4/2011 | Poeze et al. | |
| 2011/0087081 A1 | 4/2011 | Kiani et al. | |
| 2011/0105854 A1 | 5/2011 | Kiani et al. | |
| 2011/0118561 A1 | 5/2011 | Tari et al. | |
| 2011/0125060 A1 | 5/2011 | Telfort et al. | |
| 2011/0137297 A1 | 6/2011 | Kiani et al. | |
| 2011/0169644 A1 | 7/2011 | Muhsin et al. | |
| 2011/0172498 A1 | 7/2011 | Olsen et al. | |
| 2011/0208015 A1 | 8/2011 | Welch et al. | |
| 2011/0230733 A1 | 9/2011 | Al-Ali | |
| 2012/0123231 A1 | 5/2012 | O'Reilly | |
| 2012/0165629 A1 | 6/2012 | Merritt et al. | |
| 2012/0209082 A1 | 8/2012 | Al-Ali | |
| 2012/0209084 A1 | 8/2012 | Olsen et al. | |
| 2012/0226117 A1 | 9/2012 | Lamego et al. | |
| 2012/0283524 A1 | 11/2012 | Kiani et al. | |
| 2013/0023775 A1 | 1/2013 | Lamego et al. | |
| 2013/0041591 A1 | 2/2013 | Lamego | |
| 2013/0060147 A1 | 3/2013 | Welch et al. | |
| 2013/0096405 A1 | 4/2013 | Garfio | |
| 2013/0096936 A1 | 4/2013 | Sampath et al. | |
| 2013/0243021 A1 | 9/2013 | Siskavich | |
| 2013/0253334 A1 | 9/2013 | Al-Ali et al. | |
| 2013/0296672 A1 | 11/2013 | O'Neil et al. | |
| 2013/0296713 A1 | 11/2013 | Al-Ali et al. | |
| 2013/0324808 A1 | 12/2013 | Al-Ali et al. | |
| 2013/0331660 A1 | 12/2013 | Al-Ali et al. | |
| 2013/0345921 A1 | 12/2013 | Al-Ali et al. | |
| 2014/0012100 A1 | 1/2014 | Al-Ali et al. | |
| 2014/0051953 A1 | 2/2014 | Lamego et al. | |
| 2014/0077956 A1 | 3/2014 | Sampath et al. | |
| 2014/0120564 A1 | 5/2014 | Workman et al. | |
| 2014/0121482 A1 | 5/2014 | Merritt et al. | |
| 2014/0127137 A1 | 5/2014 | Bellott et al. | |
| 2014/0163344 A1 | 6/2014 | Al-Ali | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0180160 A1 | 6/2014 | Brown et al. | |
| 2014/0187973 A1 | 7/2014 | Brown et al. | |
| 2014/0213864 A1 | 7/2014 | Abdul-Hafiz et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0288400 A1 | 9/2014 | Diab et al. | |
| 2014/0316217 A1 | 10/2014 | Purdon et al. | |
| 2014/0316218 A1 | 10/2014 | Purdon et al. | |
| 2014/0316228 A1 | 10/2014 | Blank et al. | |
| 2014/0323825 A1 | 10/2014 | Al-Ali et al. | |
| 2014/0323897 A1 | 10/2014 | Brown et al. | |
| 2014/0323898 A1 | 10/2014 | Purdon et al. | |
| 2014/0330092 A1 | 11/2014 | Al-Ali et al. | |
| 2014/0330098 A1 | 11/2014 | Merritt et al. | |
| 2014/0357966 A1 | 12/2014 | Al-Ali et al. | |
| 2015/0005600 A1 | 1/2015 | Blank et al. | |
| 2015/0011907 A1 | 1/2015 | Purdon et al. | |
| 2015/0032029 A1 | 1/2015 | Al-Ali et al. | |
| 2015/0038859 A1 | 2/2015 | Dalvi et al. | |
| 2015/0073241 A1 | 3/2015 | Lamego | |
| 2015/0080754 A1 | 3/2015 | Purdon et al. | |
| 2015/0087936 A1 | 3/2015 | Al-Ali et al. | |
| 2015/0094546 A1 | 4/2015 | Al-Ali | |
| 2015/0097701 A1 | 4/2015 | Al-Ali | |
| 2015/0099950 A1 | 4/2015 | Al-Ali et al. | |
| 2015/0101844 A1 | 4/2015 | Al-Ali et al. | |
| 2015/0106121 A1 | 4/2015 | Muhsin et al. | |
| 2015/0112151 A1 | 4/2015 | Muhsin et al. | |
| 2015/0165312 A1 | 6/2015 | Kiani | |
| 2015/0196249 A1 | 7/2015 | Brown et al. | |
| 2015/0216459 A1 | 8/2015 | Al-Ali et al. | |
| 2015/0238722 A1 | 8/2015 | Al-Ali | |
| 2015/0245773 A1 | 9/2015 | Lamego et al. | |
| 2015/0245794 A1 | 9/2015 | Al-Ali | |
| 2015/0257689 A1 | 9/2015 | Al-Ali et al. | |
| 2015/0272514 A1 | 10/2015 | Kiani et al. | |
| 2015/0320365 A1* | 11/2015 | Schulze | G06F 19/321 600/408 |
| 2015/0351697 A1 | 12/2015 | Weber et al. | |
| 2015/0359429 A1 | 12/2015 | Al-Ali et al. | |
| 2015/0366507 A1 | 12/2015 | Blank | |
| 2016/0029932 A1 | 2/2016 | Al-Ali | |
| 2016/0058347 A1 | 3/2016 | Reichgott et al. | |
| 2016/0066824 A1 | 3/2016 | Al-Ali et al. | |
| 2016/0081552 A1 | 3/2016 | Wojtczuk et al. | |
| 2016/0095543 A1 | 4/2016 | Telfort et al. | |
| 2016/0095548 A1 | 4/2016 | Al-Ali et al. | |
| 2016/0103598 A1 | 4/2016 | Al-Ali et al. | |
| 2016/0166182 A1 | 6/2016 | Al-Ali et al. | |
| 2016/0166183 A1 | 6/2016 | Poeze et al. | |
| 2016/0196388 A1 | 7/2016 | Lamego | |
| 2016/0197436 A1 | 7/2016 | Barker et al. | |
| 2016/0213281 A1 | 7/2016 | Eckerbom et al. | |
| 2016/0228043 A1 | 8/2016 | O'Neil et al. | |
| 2016/0233632 A1 | 8/2016 | Scruggs et al. | |
| 2016/0234944 A1 | 8/2016 | Schmidt et al. | |
| 2016/0270735 A1 | 9/2016 | Diab et al. | |
| 2016/0283665 A1 | 9/2016 | Sampath et al. | |
| 2016/0287090 A1 | 10/2016 | Al-Ali et al. | |
| 2016/0287786 A1 | 10/2016 | Kiani | |

(56) References Cited

U.S. PATENT DOCUMENTS

| | | |
|---|---|---|
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0357812 A1 | 11/2019 | Poeze et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000415 A1 | 1/2020 | Barker et al. |
| 2020/0015716 A1 | 1/2020 | Poeze et al. |
| 2020/0021930 A1 | 1/2020 | Iswanto et al. |
| 2020/0029867 A1 | 1/2020 | Poeze et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060591 A1 | 2/2020 | Diab et al. |
| 2020/0060628 A1 | 2/2020 | Al-Ali et al. |
| 2020/0060629 A1 | 2/2020 | Muhsin et al. |
| 2020/0060869 A1 | 2/2020 | Telfort et al. |
| 2020/0074819 A1 | 3/2020 | Muhsin et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |

OTHER PUBLICATIONS

Invitation to Pay Additional Fees for International Application No. PCT/US2018/056579, dated Jan. 21, 2019, in 17 pages.

(56) References Cited

OTHER PUBLICATIONS

International Preliminary Report on Patentability and Written Opinion for International Application No. PCT/US2018/056579, dated Apr. 30, 2020, in 14 pages.

* cited by examiner

MEDICAL MONITORING SYSTEM

RELATED APPLICATIONS

Any and all applications for which a domestic priority claim is identified in the Application Data Sheet of the present application are hereby incorporated by reference under 37 CFR 1.57.

FIELD OF THE DISCLOSURE

The present disclosure relates generally to patient monitoring systems and specifically to integration and display of patient data in a patient monitoring system.

BACKGROUND

Today's patient monitoring environments are crowded with sophisticated electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patient's file for caregiver review.

The result of such device disparity is often a caregiver environment scattered with multiple displays and alarms leading to a potentially chaotic experience. Such chaos can be detrimental to the patient, particularly in surgical environments where caregiver distraction can be deadly, and including recovery or monitoring environments where patient distraction or disturbance may increase recovery times and expense.

Various manufacturers produce multi-monitor devices or devices that modularly expand to increase the variety of monitoring or treatment endeavors a particular system can accomplish. However, as medical device technology expands, such multi-monitor devices often require specific hardware and size configurations and may be limited in the number of integrated monitors.

SUMMARY

The present disclosure describes a host device that provides an improved, organized, uncluttered, and graphically-rich display for monitoring many physiological parameters of a patient. This display can be particularly useful in treatment settings, such as in a surgical setting during administration of anesthesia, where many physiological parameters can be monitored using multiple devices and all at the same time by multiple clinicians. The display can provide a real-time and intuitive set of information for clinicians that may be customized (for example, in the format or position of the presentation of data) for different clinical scenarios and assist clinicians with understanding relevant or significant physiological parameters in the different clinical scenarios. The display may include multiple concurrently-presented areas that can each provide different information intended to be more relevant to particular clinicians than other clinicians.

The host device can be part of a patient monitoring system and present an integrated display of real-time patient data and alarms from multiple integrated or non-integrated devices, such as patient monitors, ventilators, anesthesia gas machines, or intravenous (IV) pumps. The host device may provide a supplementary display for the patient data collected by the multiple devices and present information, such as comprehensive real-time patient status, historical trends, or alarm indicators, in an organized manner on one or more displays. The one or more displays can be central to a care team for a patient, and the care team can together simultaneously view and act upon the information presented. The host device can serve to reduce clinician cognitive overload and improve patient safety, as well as promote data sharing and team coordination among multiple clinicians, at least because physiological parameters may be presented by the host device in association with patient physiology or rather than the devices used to monitor the physiological parameters. This can facilitate a rapid understanding of patient needs, such as when an alarm condition arises during treatment, without clinicians having to consider one or more sources of sensor data used for determining the physiological parameters.

The host device can provide tailored, use-case-specific, or physiological-specific screen layouts (sometimes referred to as templates) that may optimize the presentation of advanced and integrated parameters, trend data, or waveforms for a variety of clinical scenarios, types of caregivers or users, or logical views. The host device may, for example, present one or more of (i) an overview layout for displaying patient monitoring data from most or all connected point-of-care or therapeutic devices including waveforms and alarms for an overview of patient status, (ii) a hemodynamics layout for displaying trend data for noninvasive hemoglobin (SpH®), pleth variability index (PVi®), or pulse rate to aid in visualizing patient status over time, (iii) an oxygenation layout for displaying ventilator waveforms alongside noninvasive trended hemoglobin (SpHb®) and oxygen saturation (SpO2) to monitor a patient's oxygenation status, or (iv) a sedation layout for displaying electroencephaogram (EEG) waveforms, patient state index (PSi™) or anesthesia machine data to monitor a patient's sedation. Other potential layouts that may be presented by the host device can include a vital signs layout for displaying a collection of vital signs data from multiple devices, as well as a human body image layout for displaying values or magnitudes of parameters within or along a graphic of a human body that may be animated. Additionally, the host device can control one or more settings or other operations of the multiple devices or other additional components in a patient monitoring system.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

FIG. 7 illustrates controls on a display of a host device for adjusting alarm limit ranges.

FIGS. 18A, 18B, 18C, 18D, 18E, 19, and 20 illustrate configuration of a display for presentation of measurement data.

Figure 52:
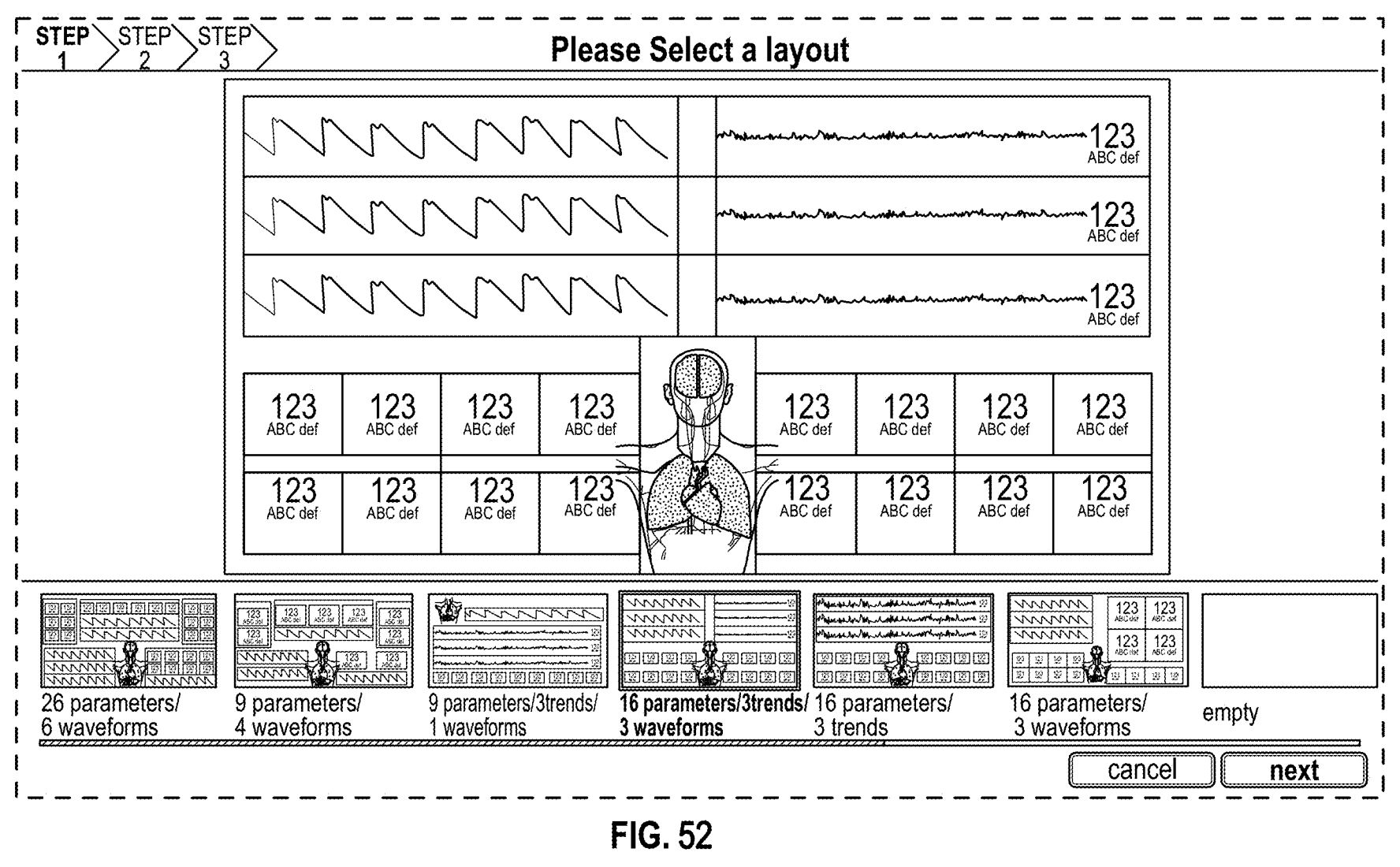

FIG. 52 is a front view of a display screen or portion thereof with a graphical user interface in accordance with a twenty-fifth embodiment;

Figure 53:
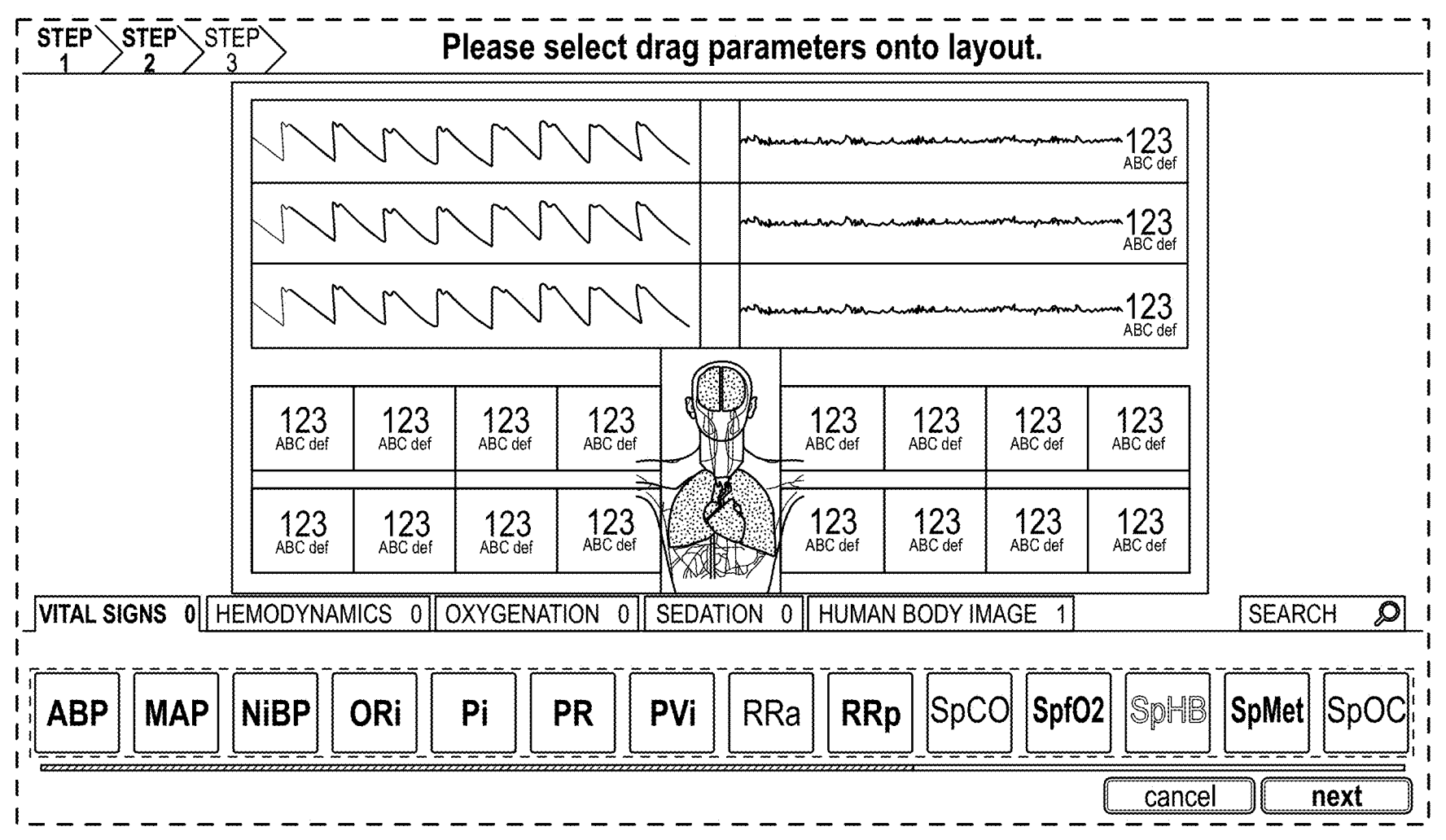

FIG. 53 is a front view of a display screen or portion thereof with a graphical user interface in accordance with a twenty-sixth embodiment;

Figure 54:
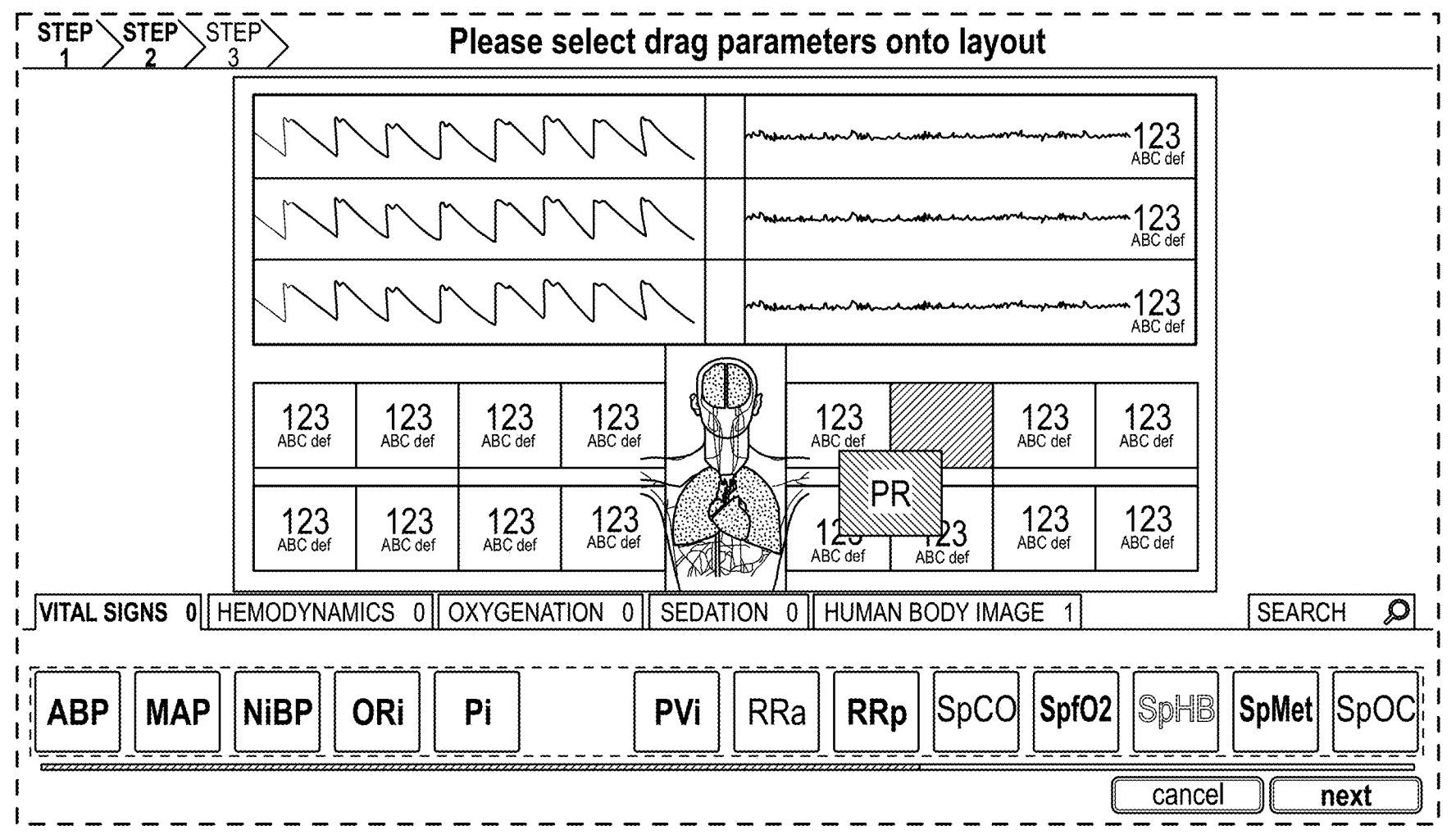

FIG. 54 is a front view of a display screen or portion thereof with a graphical user interface in accordance with a twenty-seventh embodiment;

Figure 55:
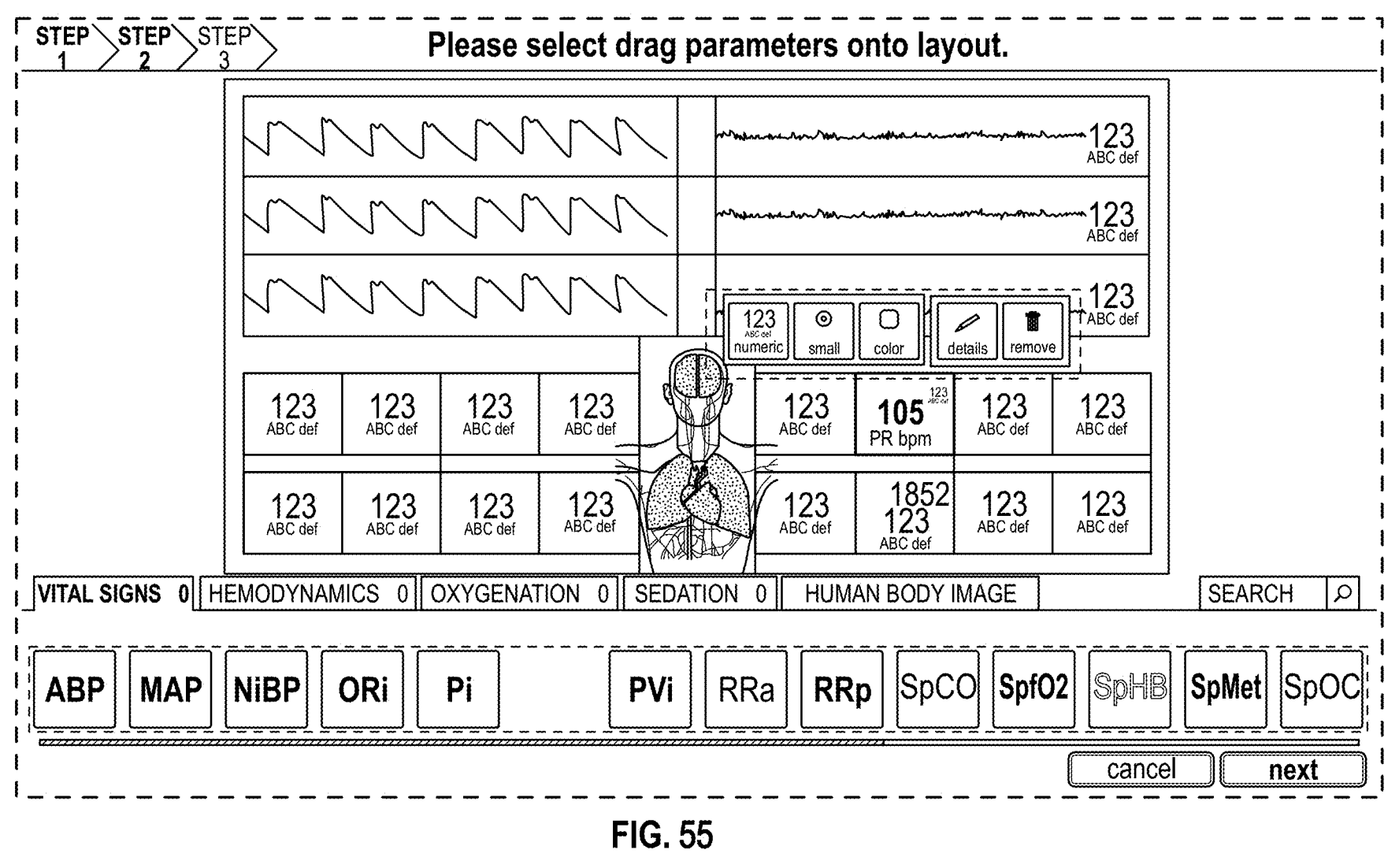

FIG. 55 is a front view of a display screen or portion thereof with a graphical user interface in accordance with a twenty-eighth embodiment;

DETAILED DESCRIPTION

Introduction

Figure 1:
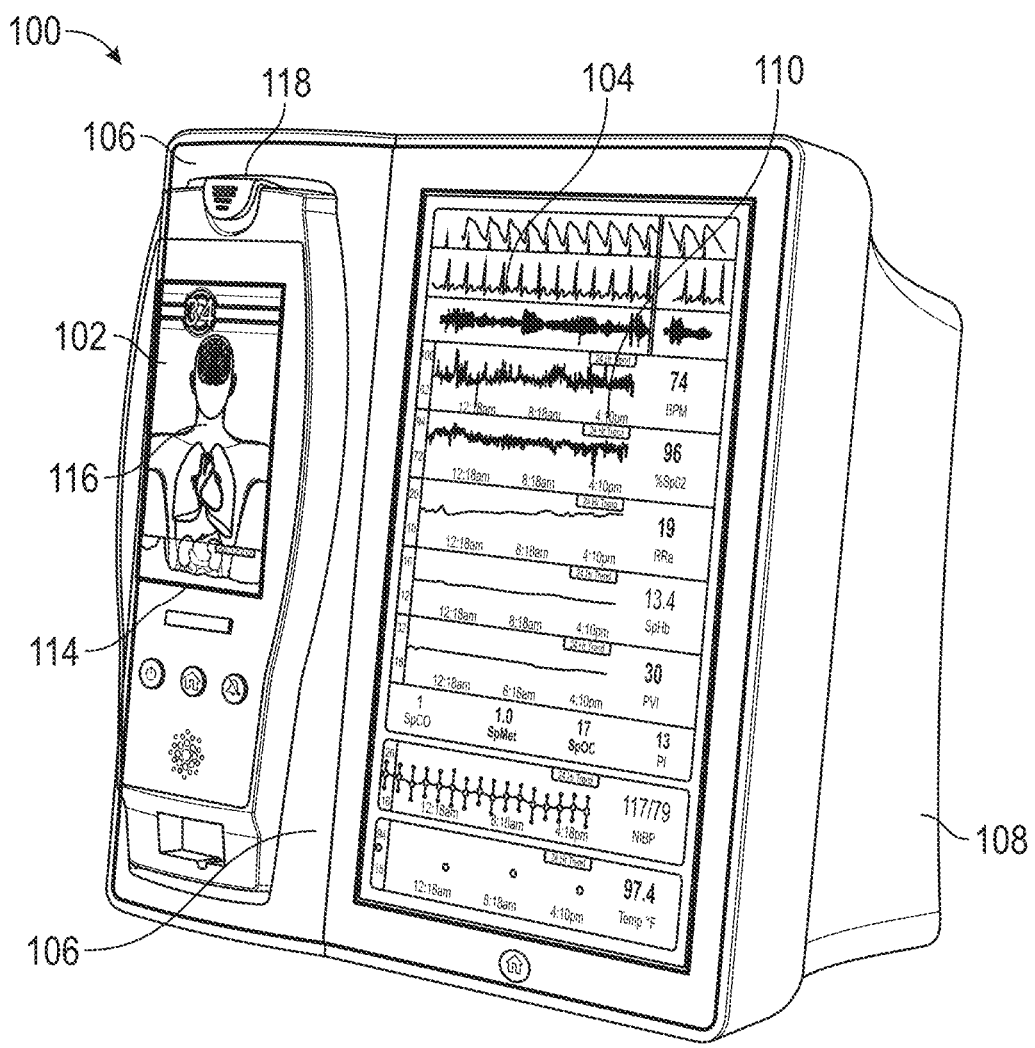
FIG. 1 illustrate a perspective view of a medical monitoring hub.

The present disclosure relates to a host device for presenting an integrated display of patient data and alarms for a single patient. The patient data and alarms can be obtained from multiple devices, such as patient monitors, ventilators, anesthesia gas machines, or intravenous (IV) pumps that are used in monitoring the single patient. The host device can provide an additional, centralized display for patient data collected from the multiple devices and present information in tailored, use-case-specific screen, or physiological-specific layouts that optimizes the presentation for a variety of clinical scenarios. The host device can also control one or more settings or other operations of the multiple devices or other additional components in a patient monitoring system.

The host device can operate in coordination with a medical monitoring hub configured to be the center of monitoring activity for a given patient. The host device can be connected to the hub directly or indirectly through a network or a server. The host device can be associated with a display screen for projecting data received from the hub. The host device may, for example, be the television, a monitor, a cellphone, tablet, laptop or desktop computer, or one or more other devices having a hardware processor configured to execute a patient data display system. The hub may itself have a patient data display system installed and can cause a display external to the hub to present patient data. Because the hub may also have its own display, some patient data may be displayed both on the display of the hub and the external display.

The host device may communicate directly with point-of-care (POC) devices. A POC device may, for instance, be a portable patient monitor or another type of device that provides patient monitoring, such as bed-side to a patient. The host device may communicate with a server system to receive patient parameter data. The display associated with the host device can provide measurement data for a wide variety of monitored parameters for the patient under observation in numerical or graphic form and may be automatically configured based on the type of data and information being received at the host device. The host device is moveable, portable, or mountable so that it can be positioned to convenient areas within a caregiver environment. For example, the host device is collected within a singular housing.

The host device or the hub may receive data from a portable patient monitor. Typical portable patient monitors, such as oximeters or co-oximeters can provide measurement data for a large number of physiological parameters derived from signals output from optical or acoustic sensors, electrodes, or the like. The physiological parameters include, but are not limited to oxygen saturation, carboxyhemoglobin, methemoglobin, total hemoglobin, glucose, pH, bilirubin, fractional saturation, pulse rate, respiration rate, components of a respiration cycle, indications of perfusion including perfusion index, signal quality or confidences, plethysmograph data, indications of wellness or wellness indexes or other combinations of measurement data, audio information responsive to respiration, ailment identification or diagnosis, blood pressure, patient or measurement site temperature, depth of sedation, organ or brain oxygenation, hydration, measurements responsive to metabolism, combinations of the same or the like, to name a few. The hub may output data sufficient to accomplish closed-loop drug administration in combination with infusion pumps or the like.

The hub communicates with other devices in a monitoring environment that are interacting with the patient in a number of ways. For example, the hub advantageously receives serial data from other devices (which may be POC devices) without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses nurse call systems to ensure that nurse call situations from the device are passed to the appropriate nurse call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn may communicate with a caregiver's data management systems, such as, for example, an Admit, Discharge, Transfer ("ADT") system or an Electronic Medical Records ("EMR") system. The hub advantageously associates the data flowing through it with the patient being monitored thereby providing the electronic measurement and treatment information to be passed to the caregiver's data management systems without the caregiver associating each device in the environment with the patient.

The hub advantageously includes a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

The hub includes a large memory for storing some or all of the data it receives, processes, or associates with the patient, or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously provide optional electrically isolated power and communications, are designed to be smaller in cross section than isolation requirements. The connectors and the hub communicate to advantageously translate or configure data from other devices to be usable and displayable for the hub. A software developers kit ("SDK") is provided to a device manufacturer to establish or define the behavior and meaning of the data output from their device. When the output is defined, the definition is programmed into a memory residing in the cable side of the universal medical connector and supplied as an original equipment manufacturer ("OEM") to the device provider. When the cable is connected between the device and the hub, the hub understands the data and can use it for display and processing purposes without necessitating software upgrades to the device or the hub. The hub can negotiate the schema and even add additional compression or encryption. Through the use of the universal medical connectors, the hub organizes the measurement and treatment data into a single display and alarm system effectively and efficiently bringing order to the monitoring environment.

As the hub receives and tracks data from other devices according to a channel paradigm, the hub may advantageously provide processing to create virtual channels of patient measurement or treatment data. A virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems or caregiver backend systems discussed above. Through receiving the serial data, the caregiver advantageously associates devices in the caregiver environment, often from varied manufactures, with a particular patient, avoiding a need to have each individual device associated with the patient and possible communicating with hospital systems. Such association is vital as it reduces caregiver time spent entering biographic and demographic information into each device about the patient. Moreover, through the SDK the device manufacturer may provide information associated with any measurement delay of their device, thereby further allowing the hub to advantageously time-wise synchronize serial incoming data and other data associated with the patient.

When a portable patient monitor is docked, and it includes its own display, the host device or hub effectively increases its display real estate. For example, the portable patient monitor may simply continue to display its measurement or treatment data, which may be now duplicated on the host device or hub display, or the display may alter its display to provide additional information. The display presents anatomical graphical data of, for example, the heart, lungs, organs, the brain, or other body parts being measured or treated. The graphical data may advantageously animate similar to and in concert with the measurement data. For example, lungs may inflate in approximate correlation to the measured respiration rate or the determined inspiration/expiration portions of a respiration cycle, the heart may beat according to the pulse rate, may beat generally along understood actual heart contraction patterns, the brain may change color or activity based on varying depths of sedation, or the like. When the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. The body portions may include animations on where, when or how to attach measurement devices.

The host device or hub may also advantageously overlap parameter displays to provide additional visual information to the caregiver. Such overlapping may be user definable and configurable. The display may also incorporate analog-appearing icons or graphical indicia.

To facilitate a complete understanding of the disclosure, the remainder of the detailed description describes the disclosure with reference to the drawings, wherein like reference numbers are referenced with like numerals throughout.

Medical Monitoring Hub Operating Environment

FIG. 1 illustrates a perspective view of a medical monitoring hub 100 with a docked portable patient monitor 102. The hub 100 includes a display 104, and a docking station 106, which is configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

The display 104 may present a wide variety of measurement or treatment data in numerical, graphical, waveform, or other display indicia 110. The display 104 occupies much of a front face of the housing 108, although an artisan will appreciate the display 104 may comprise a tablet or tabletop horizontal configuration, a laptop-like configuration or the like. The display information and data may additionally or alternatively communicated to a table computer, smartphone, television, or any display system recognizable to an artisan. The upright inclined configuration of FIG. 1 presents display information to a caregiver in an easily viewable manner.

The portable patient monitor 102 of FIG. 1 may advantageously comprise an oximeter, co-oximeter, respiratory monitor, depth of sedation monitor, noninvasive blood pressure monitor, vital signs monitor or the like, such as those commercially available from Masimo Corporation of Irvine, Calif., or disclosed in U.S. Pat. Pub. Nos. 2002/0140675, 2010/0274099, 2011/0213273, 2012/0226117, 2010/0030040; U.S. Pat. App. Ser. Nos. 61/242,792, 61/387,457, 61/645,570, 13/554,908 and U.S. Pat. Nos. 6,157,850, 6,334,065, and the like. The monitor 102 may communicate with a variety of noninvasive or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116. The display indicia may advantageously change based on a docking state of the monitor 102. When undocked, the display indicia may include parameter information and may alter orientation based on, for example, a gravity sensor or accelerometer.

The docking station 106 of the hub 100 includes a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, or wirelessly communicate with the same.

Additional or alternative features of the hub 100, its presentation of information, and its operating environment are described in U.S. Pat. No. 9,943,269, issued Apr. 17, 2018, titled "SYSTEM FOR DISPLAYING MEDICAL MONITORING DATA," the disclosure of which is incorporated by reference herein.

Figure 2:
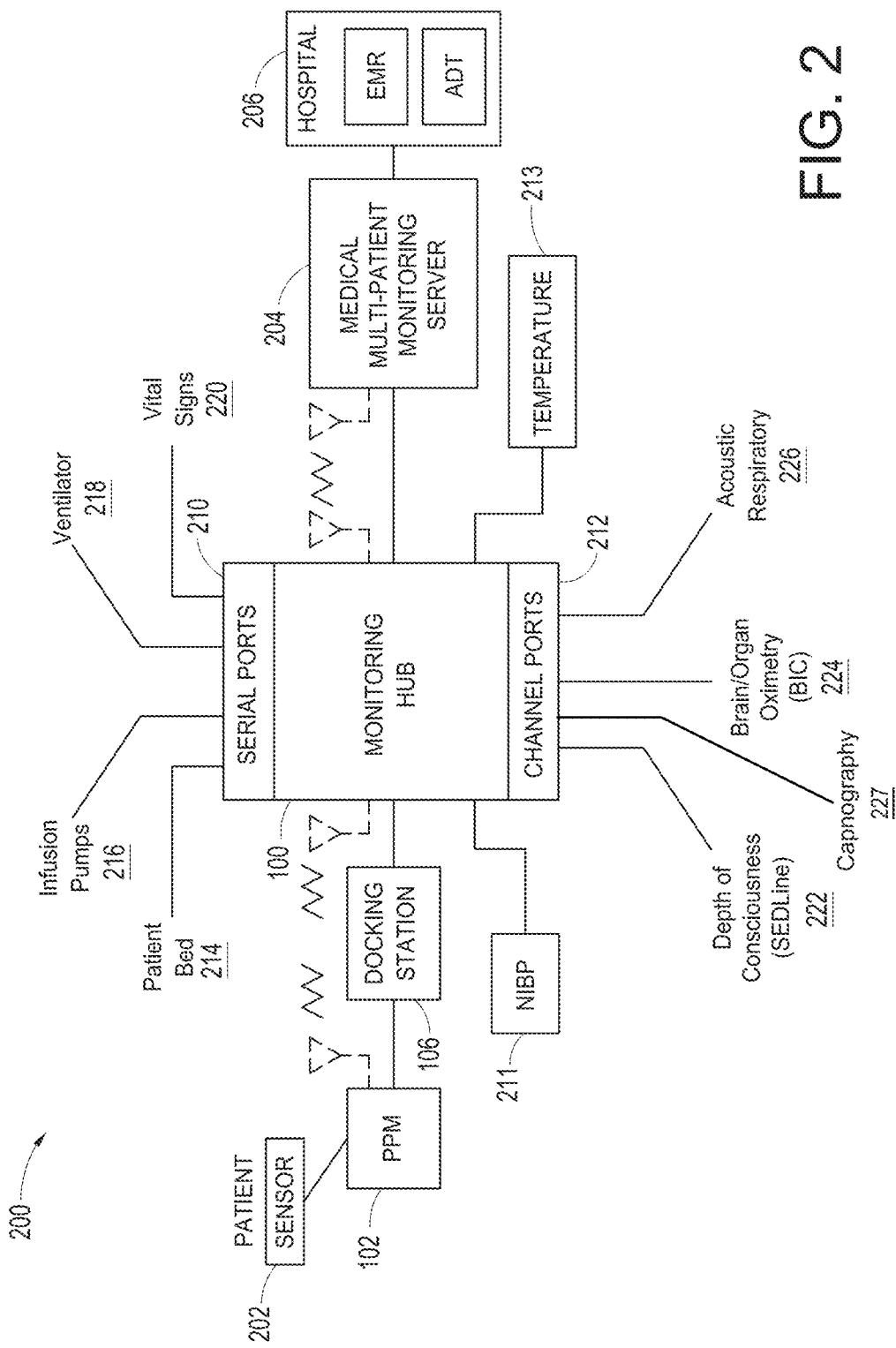
FIG. 2 illustrates a simplified block diagram of a monitoring environment including the medical monitoring hub of FIG. 1.

FIG. 2 illustrates a simplified block diagram of a monitoring environment 200 including the hub 100 of FIG. 1. As shown in FIG. 2, the environment may include the portable patient monitor 102 communicating with one or more patient sensors 202, such as, for example, oximetry optical sensors, acoustic sensors, blood pressure sensors, respiration sensors or the like. Additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

The portable patient monitor 102 may communicate with the hub 100 through the docking station 106 when docked and wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140, which are hereby incorporated by reference in their entirety. In general, the server 204 communicates with caregiver backend systems 206 such as EMR or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SedLine™, other brain or organ oximeter devices 224, noninvasive blood pressure or acoustic devices 226, capnography devices 227, or the like. Channel device may include board-in-cable ("BIC") solutions where the processing algorithms and the signal processing devices that accomplish those algorithms are mounted to a board housed in a cable or cable connector, which may have no additional display technologies. The BIC solution outputs its measured parameter data to the channel port 212 to be displayed on the display 104 of hub 100. The hub 100 may advantageously be entirely or partially formed as a BIC solution that communicates with other systems, such as, for example, tablets, smartphones, or other computing systems.

Figure 3:
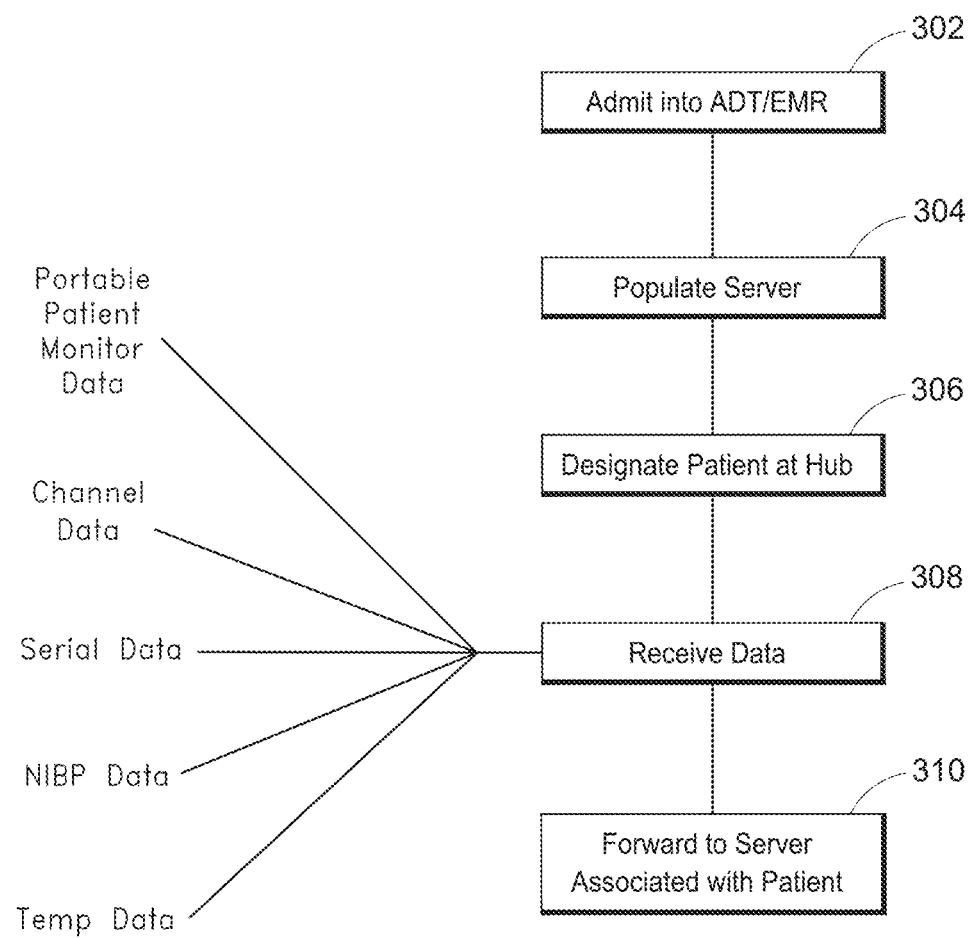
FIG. 3 illustrates a simplified patient data flow process.

FIG. 3 illustrates a simplified patient data flow process. As shown, once a patient is admitted into the caregiver environment at step 302, data about the patient is populated on the caregiver backend systems 206. The server 204 may acquire or receive this information in step 304, and then make it accessible to the hub 100. When the caregiver at step 306 assigns the hub 100 to the patient, the caregiver simply looks at the presently available patient data and selects the particular patient being currently monitored. The hub 100 at step 308 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms. At step 310, some or the entirety of the received, processed or determined data is passed to the server 204.

Host Device Data Presentation and Control

Figure 4A:
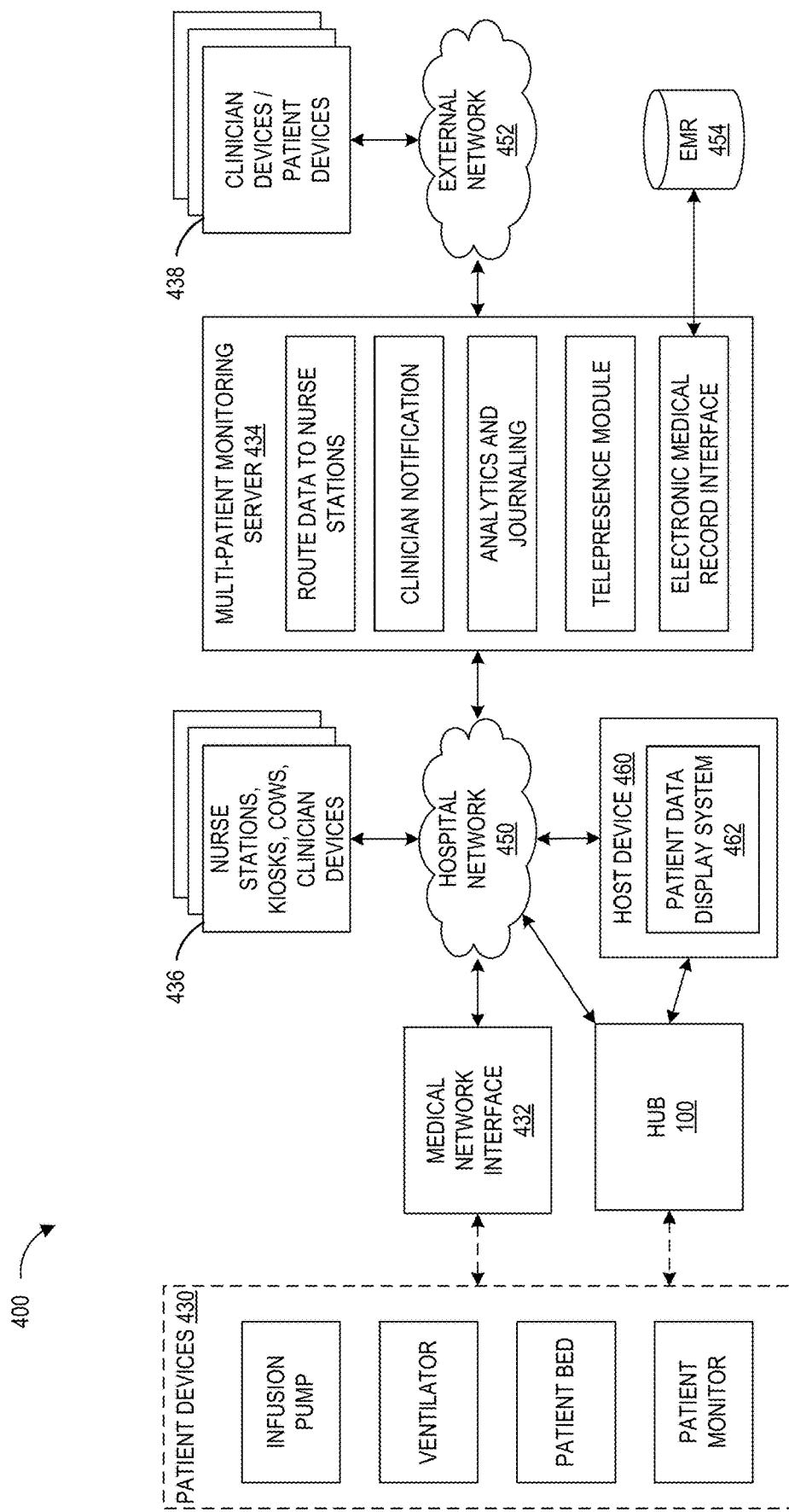
FIG. 4A illustrates a computing environment including a host device.

FIG. 4A illustrates an example computing environment 400 in which patient data is acquired and processed. In the computing environment 400, patient devices 430 connect with a medical network interface 432, which provides network connection functionality for these devices by connecting to a hospital network 450. The patient devices 430 may be PoC devices. Also connected to the hospital network 450 is a multi-patient monitoring server (MMS) 434, a host device 460, and other hospital devices 436, such as nurses stations, kiosks, computers on wheels (COWs), and clinician devices (such as phones, pagers, tablets, and the like). The MMS 434 is also in communication with an external network 452 which may communicate with clinician devices or patient devices 438, which can include, for instance, devices that may be remote from the hospital. The MMS 434 for also interfaces with EMR 454. Thus, the medical network interface 432 may enable data from the patient devices 430 to be communicated to any of the other components shown in FIG. 4, among possibly others.

The MMS 434 may route data to nurse stations (sometimes referred to as central stations). Data received from the patient devices 430 of the medical network interface 432 may be provided to their stations, central stations, and clinician devices, among others. The MMS 434 may perform clinician notification, for example, by routing alarms obtained from the patient devices 430 to the devices 436, 438. Further, the MMS 434 may perform analytics and journaling, for example, as disclosed in U.S. Pat. No. 9,142,117, filed Sep. 22, 2015, titled "Systems and Methods for Storing, Analyzing, Retrieving and Displaying Streaming Medical Data," the disclosure of which is hereby incorporated by reference in their entirety. Further, the MMS 434 may include telepresence module that performs telepresence monitoring of patients by clinicians remotely, for example, as described in U.S. Pub. No. 2014/0077956, filed Sep. 18, 2013, titled "Intelligent Medical Network Edge Router," the disclosure of which is hereby incorporated by reference in its entirety. Further, the MMS 434, like the MMS 434, may be expandable and can supply data to other software engines and databases, including the EMR 454.

The data obtained by the medical network interface 432 from the patient devices 430 (or from the hub 100) may come in one or more of the following forms: waveform data, parameter data, or event data. Waveform data can include trend data, which may be high-frequency data. The medical network interface 432 or the MMS 434 may treat this data akin to video streaming data, such that if there are losses (for example, due to buffer overruns), those losses are ignored. Parameter data (for example, physiological parameter measurement such as oxygen saturation values), may come at a set frequency such as once every second (1 Hz). The medical network interface 432 may combine parameter data into a patient snapshot and provide this snapshot to the MMS 434 or to other devices shown. Event data can include event driven data, such as alarms (for example, parameter values going out of bounds) and alerts (for example, a progress fallen off or alarm settings were change on one of the patient devices 430). Events may be supplied asynchronously, when they occur, and the medical network interface 432 may apply a time stamp to any events received from the patient devices 430 before supplying the event data to other devices on the network.

The host device 460, the patient devices 430, the MMS 434 may be connected to the hospital network 450. The hub 100 can be connected to the host device 460 directly or via the hospital network 450. The hospital network 450 can support wireless or hard wired network communications. The patient devices 430 can include devices that provide bedside patient monitoring.

The host device 460 can include a display 464 configured to present patient information. In one example, the host device 460 may be a television, monitor, cellphone, tablet, laptop or desktop computer and include a patient data display system 462, which may be installed on a memory of the host device 460. The patient data display system 462 can be configured to communicate with the MMS 434, the patient devices 430, the hub 100, the medical network interface 432, alone or in combination, to receive patient data or provide control instructions. In one implementation, the host device 460 executes an Android™ operating system, and the patient data display system 462 is a program loaded and that runs on the Android™ operating system.

The patient data display system 462 can, for example, group data based on the parameters being monitored, a source of the data, a patient physiology, or a use-case-specific manner. The patient parameters may be prioritized for display. The prioritization may be associated with parameters within the patient devices 430. For example, where one of the patient devices 430 provides data from three parameters, the three parameters may be prioritized among themselves. Parameters may also be prioritized depending on the patient devices 430 connected, such as to the hub 100, and the display layout selected for the host device 460. For example, in one screen layout, such as for a sedation clinical scenario, the sedation layout (shown in FIG. 6C) may cause one set of parameters to be prioritized for display, whereas in another screen layout, such as for an overview scenario, the overview layout (shown in FIG. 5) may cause a different set of parameters to be prioritized.

As will further be described with reference to FIGS. 7, 8A, and 8B, the patient data display system 462 can include alarm features, and the patient data display system 462 can allow a user to adjust the alarm limit of one or more of the patient devices 430 via the host device 460. The host device 460 can accordingly send the adjusted alarm limit to the patient devices 430 or another device (such as, the medical network interface 432 or the MMS 434) for implementation by the patient devices 430. The host device 460 may not itself generate or manage alarms but instead provide an interface through which alarms may be presented, grouped, and acted on.

The patient data display system 462 can provide animations associated with anatomical features of a patient, such as shown in the examples described with reference to FIG. 9. The anatomical features of the patient may, for instance, be animated at the rate of associated parameters. Similar animations may be provided on the hub 100.

Figure 4B:
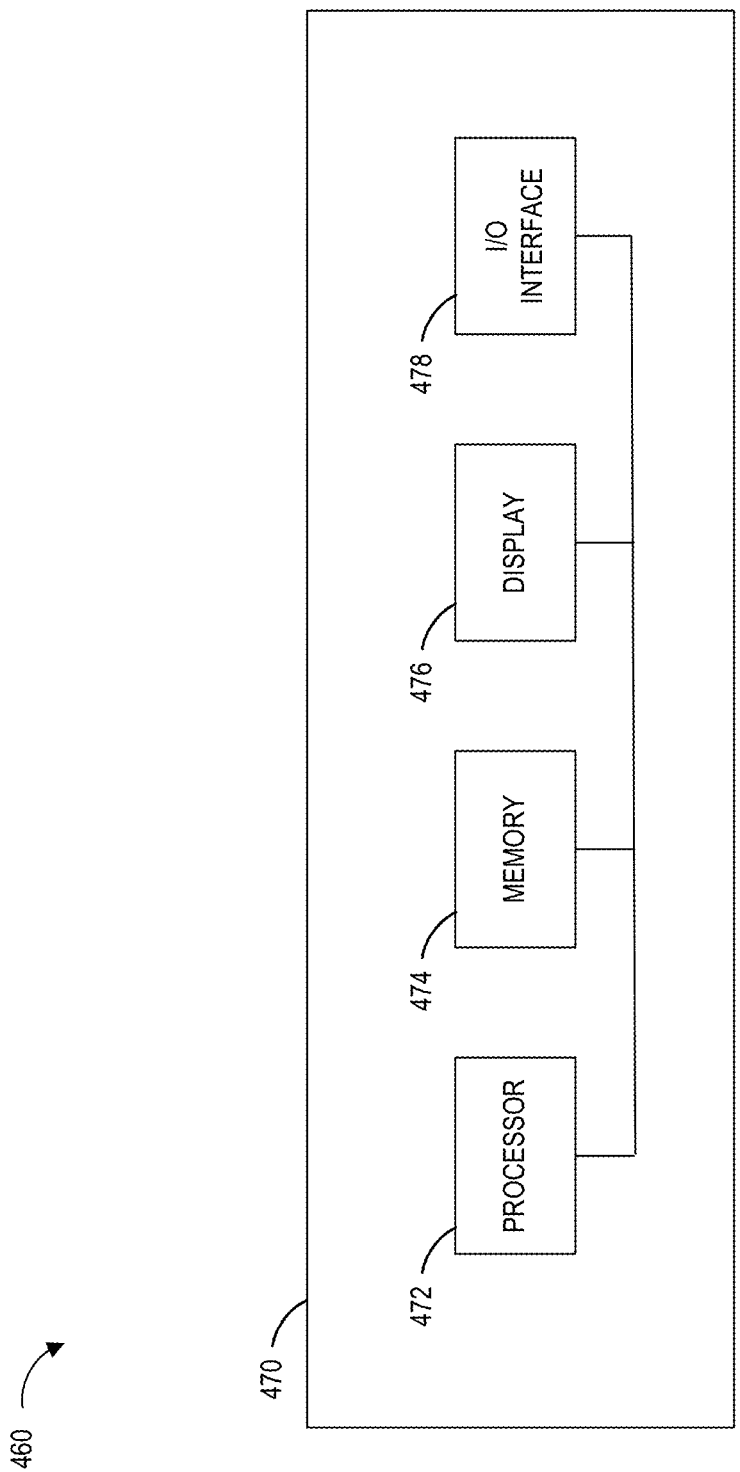
FIG. 4B illustrates a simplified hardware block diagram of the host device of FIG. 4A.

FIG. 4B illustrates a simplified hardware block diagram of the host device 460 of FIG. 4A. The host device 460 can include a housing 470, a processor 472, a memory 474, a display 476, and an input/output (I/O) interface 478. The housing 470 can support or enclose one or more of the other components of the host device 460. The processor 472, the memory 474, the display 476, and the input/output (I/O) interface 478 can communicate with one another via wired or wireless communication. The processor 472 can control operations of the host device 460 according at least to instructions stored on the memory 474. The memory can, for example, store the patient data display system 462. The processor 472 can present information on the display 476, such as by presenting one or more of the screens or user interfaces described herein. The input/output interface 478 can be used by the processor 472 to receive or transmit data, such as patient data, from or to one or more other electronic devices via wired or wireless communication.

Figure 5:
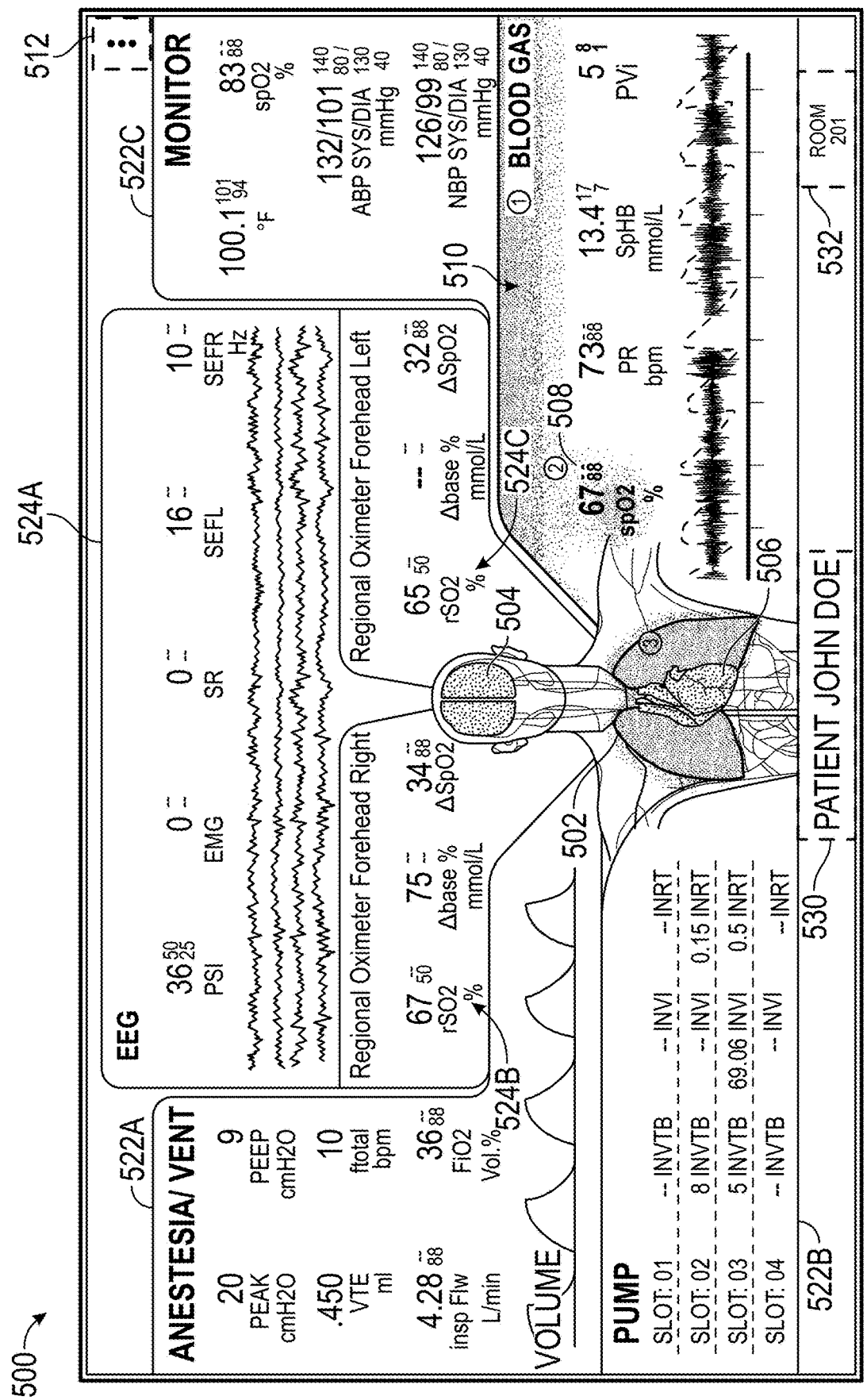
FIG. 5 illustrates a display of measurement data organized by source electronic devices or channels.

FIG. 5 illustrates displays of measurement data on a display of a host device, such as the display 476, or another display described herein. The measurement data may be organized by source electronic devices or channels. As shown in FIG. 5, the parameters received from a particular source electronic device or channel or computed from the particular source electronic device or channel can be grouped together and presented in a dedicated area on the display corresponding to the particular source electronic device or channel.

The screen layout shown in FIG. 5 may be an overview screen 500. The overview screen 500 may be a default layout screen displayed after a patient is selected. The identifier for the patient can be provided at a patient identifier area 530, and a room in a physical treatment facility in which the patient is being treated can be identified at a patient room area 532. The patient may be selected after the patient has been admitted as described with respect to FIG. 3.

The overview screen 500 can include one or more of the dedicated areas (sometimes referred to as windows for purposes of illustration, but may take forms other than windows), such as an anesthesia/vent window 522A, EEG window 524A, regional oximeter forehead right window 524B, regional oximeter forehead left window 524C, monitor window 522C, blood gas window 510, and infusion pump window 522B, among others. More or fewer windows may alternatively be shown on the overview screen 500. For example, the overview screen 500 can additionally or alternatively include a window for capnography.

The anesthesia/vent window 522A can display data from an anesthesia or ventilator device. A first-connected or a last-connected anesthesia or ventilator device may have a highest priority and its data will be displayed. The anesthesia/vent window 522A can display data for a variety of parameters, such as, for example, PEEP, Ppeak, Pmean, PLAT, Vte, Ve, $EtO_2$, $FiO_2$. The anesthesia/vent window 522A can also display waveforms, such as, for example, pressure, volume, and flow waveforms.

The size of the anesthesia/vent window 522A may change depending on whether one or more associated devices are disconnected or connected, such as from or to the hub 100. For example, the anesthesia/vent window 522A may expand when one or more capnography or pump devices is disconnected or powered off. Because the size of the anesthesia/vent window 522A can change, no waveforms may be visible, for instance, if a capnography device is connected or all three waveforms may be visible if the capnography device is not connected. The pressure waveform may be visible if a pump device is connected and a capnography device is disconnected.

Although not shown in FIG. 5, the overview screen 2500 can also display data from a capnography device. For example, the overview screen 500 can include a window for displaying parameters such as $EtCO_2$, $FiCO_2$, RR, or $CO_2$ waveform. The window for a capnography device can be visible when the capnography is connected, such as to the hub 100.

The infusion pump window 522B can display parameters related to fluid delivery, such as INVTB, INV, INRT, and INRMT. The infusion pump window 522B may, for instance, be visible when an infusion pump device is connected, such as to the hub 100.

The EEG window 524A can display data received from a EEG monitoring device, such as the EEG monitor marketed under the name SedLine® and sold by Masimo Corporation of Irvine, Calif. The EEG window 524A can display parameters indicative of brain activity, such as PSi™, EMG, SR, SEFL, SEFR, ARTF. The EEG window 524A can also display the EEG waveform. The EEG window 524A may change size as one or more regional oximeter devices is connected or disconnected, such as to or from the hub 100.

The regional oximeter forehead right and left windows 524B and 524C can display regional oximeter sensor data from regional oximeter sensors. One such regional oximeter sensor is marketed under the name O3® and sold by Masimo Corporation of Irvine, Calif. For example, the regional oximeter forehead right and left windows 524B and 524C can display data for parameters indicative of cerebral oxygenation, such as $rSO_2$, Delta Baseline (Abase), Delta $SpO_2$ ($\Delta SpO_2$).

The monitor window 522C can display data from third-party monitoring devices, such as devices other than those provided or manufactured by someone other than a provider or manufacturer of the hub 100 or the host device 460. For example, the monitor window 522C can display data related to one or more of the following parameters: Temperature, NiBP Systolic, NiBP Diastolic, ECG HR, PVC, CVP, ST aVL, ST aVR. The monitor window 522C may be visible when at least one of the third-party monitoring devices is connected, such as to the hub 100.

The blood gas window 510 can display measurement data from native sensors, such as, for example, sensors that are compatible with the hub 100 or sensors that can be directly connected to the hub 100 or are provided or manufactured by a provider or manufacturer of the hub 100. One such blood gas sensor is marketed under the name Rainbow and sold by Masimo Corporation of Irvine, Calif. The size of the blood gas window 510 may change, for example, depending on whether a third-party monitoring device is connected or disconnected, such as to or from the hub 100. For example, the blood gas window 510 may expand (for example, to also include the area corresponding to the monitor window 522C) when the third-party monitoring device is disconnected, such as from the hub 100, or powered off. The blood gas window 510 can display one or more parameters indicative of pH, oxygen level, or carbon dioxide level, such as SpO2% PVi %, etc. The blood gas window 510 can also display Pleth, Signal I.Q.®, and Respiration Envelope waveforms.

The display shown in FIG. 5 may not be able to fit in all patient parameters that are being monitored. As a result, the windows displayed may be displayed based on priority, or the parameters may be displayed within individual windows based on priority. For example, the monitor window 522C may be hidden if the monitor window 522C is considered to be a relatively lower priority, and the blood gas window 510 may display the first 8 parameters that have a highest priority but not one more or additional parameters that may other be displayed.

The display illustrated in FIG. 5 can present a graphic of an upper portion of a person. The graphic can include a lung 502, a brain 504, and a heart 506. Each of the lung 502, the brain 504, and the heart 506 can be colored green or red where green indicates an alarm inactive and red indicates an alarm active for the organ depicted by the red graphic. An area around a particular parameter may additionally turn red to indicate an alarm active associated with the particular parameter, and a portion of a dedicated area in which the particular parameter is shown may also turn red. For instance, an area 508 around the displayed SpO2% value or another area in the blood gas window 510 can be red indicating an alarm condition. A menu element 512 can enable a user to transition from displaying FIG. 5 to displaying an alternative interface, such as an option configuration interface for adjusting one or more of enabling/disabling alarm status visualizer animations, viewing patient data for a different patient, disconnecting from a patient monitoring device or system, or viewing a current version of the software for the patient data display system 462.

The display depicted in FIG. 5 can include a shading (not shown), such as a gray shading in an area similar to the area 508, which may indicate that a window or a parameter presents input information rather than output information. The output information may, for example, include information measured by one or more sensors monitoring a patient while the input information can include information used to control treatment of the patient. The shading can thus provide a quick and accessible indication to a caregiver whether information on the display may be input or output information. The display can include a highlighting (not shown) of particular parameters or windows. The highlighting can be used to attract attention of a user to the particular parameters or windows so assist the user with processing presented information. One or more parameters or windows can be automatically hidden from display when the parameters may be within a safe or acceptable range to reduce the amount of information that may be presented at one time.

Figure 6A:
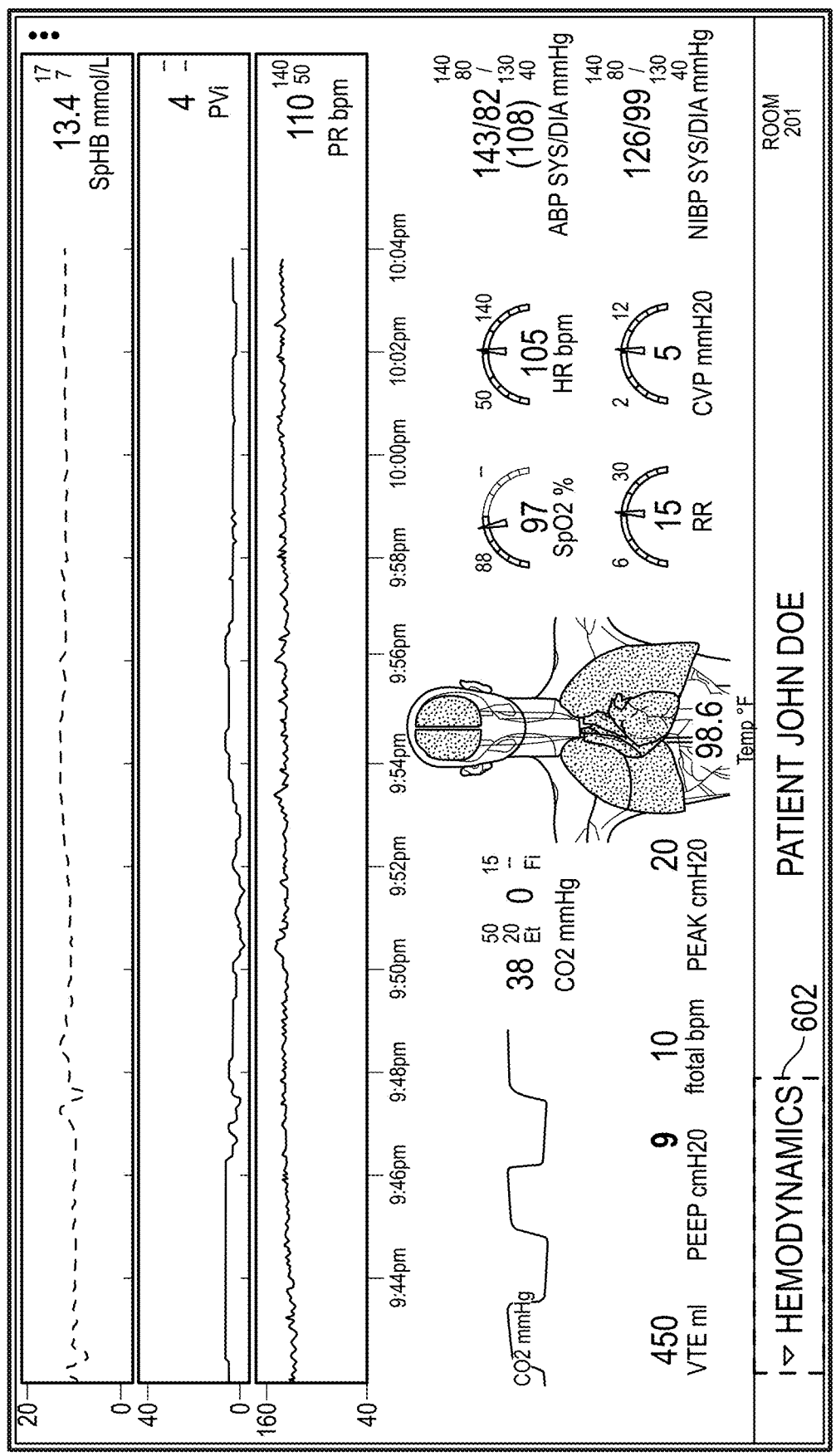
FIGS. 6A, 6B, and 6C illustrate displays of measurement data organized by a clinical scenario for the patient.
Figure 6B:
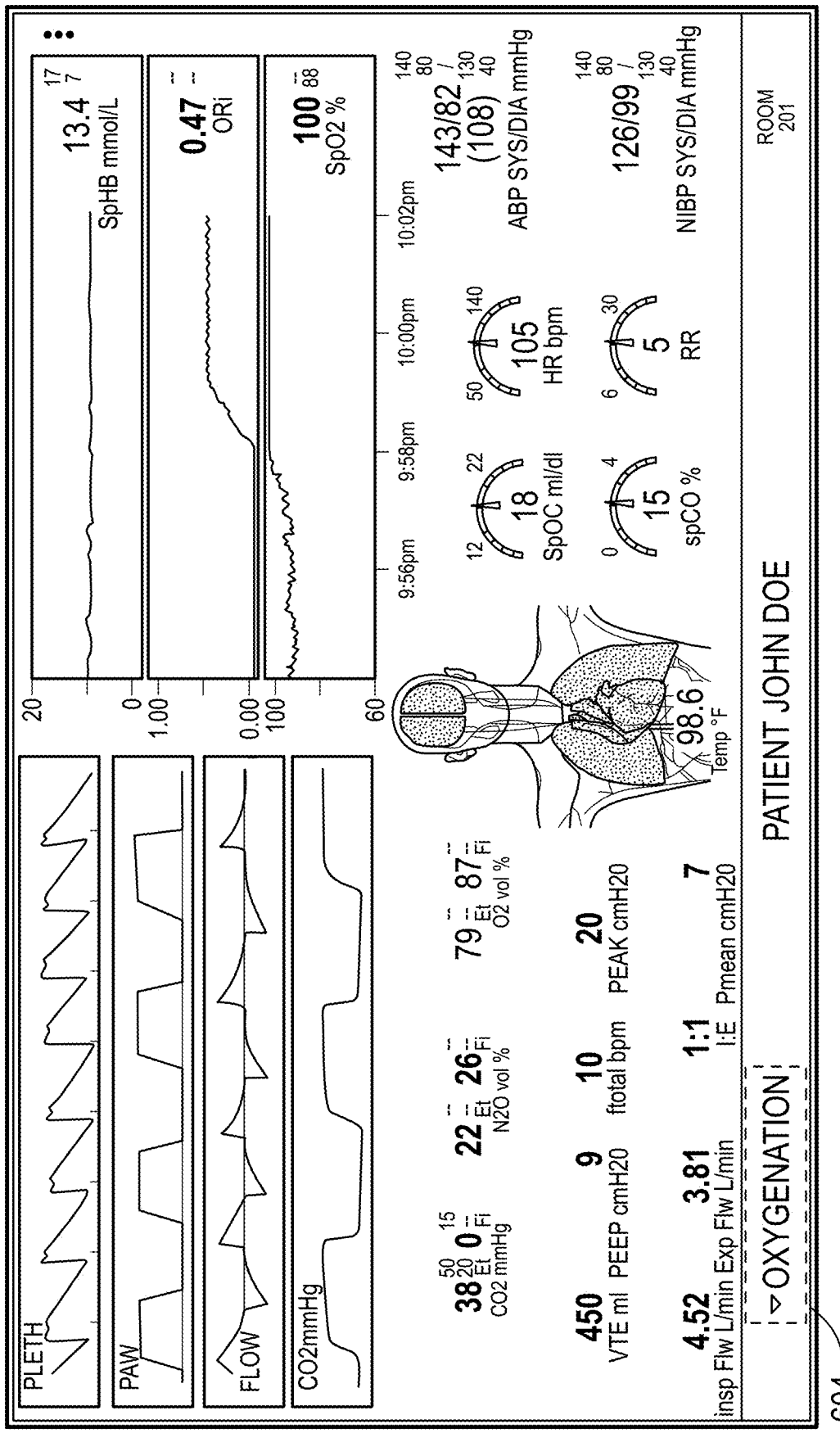
Figure 6C:
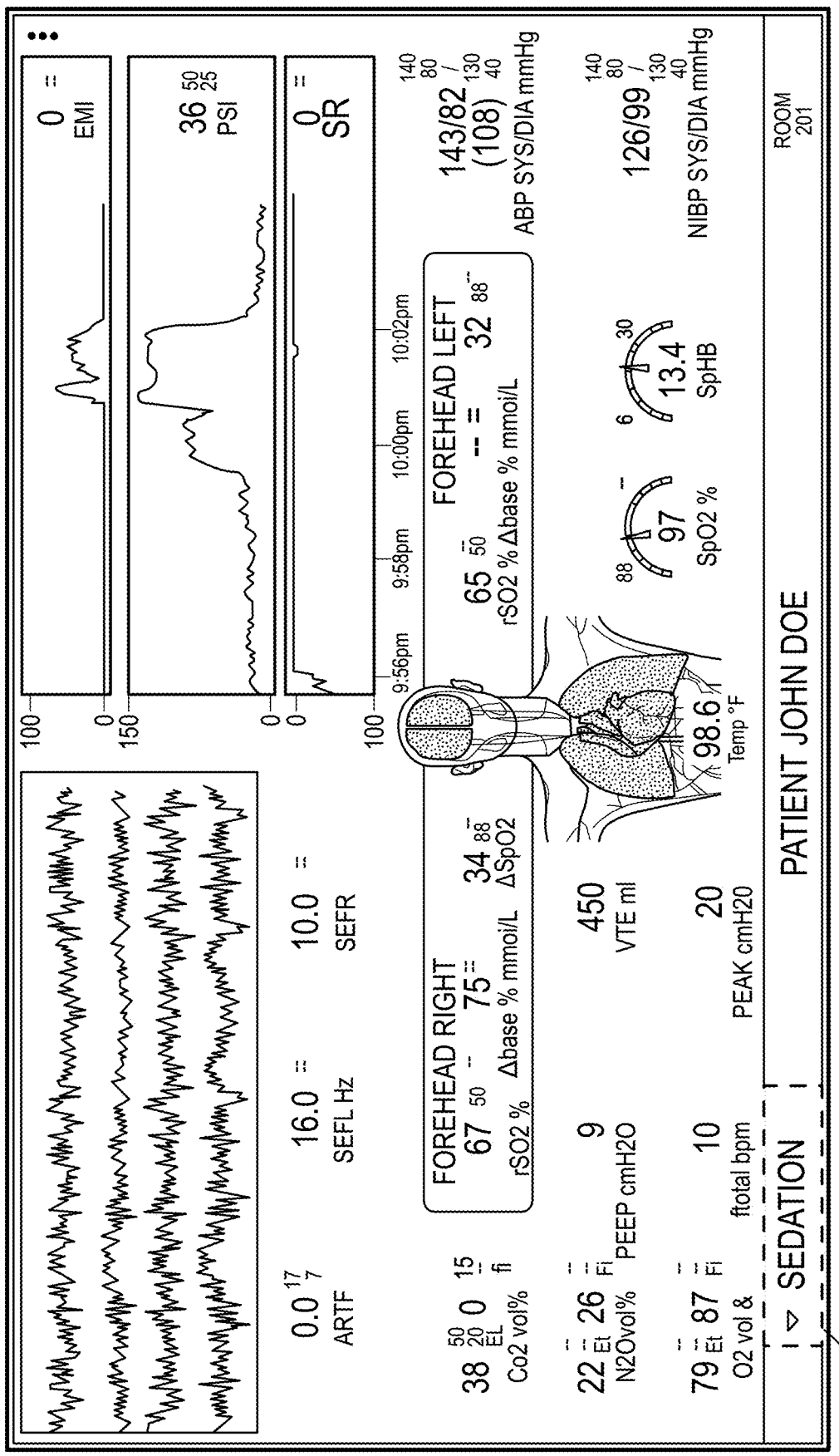

FIGS. 6A, 6B, and 6C illustrate displays of measurement data on the display of a host device, such as the display 476, or another display described herein. The displays of measurement data can, for instance, be presented or organized according to a physiological system of a patient, clinical scenarios, or various use cases. The displays of FIGS. 6A, 6B, and 6C may contrast with the displays of FIG. 5, which instead may present or organize measurement data according to source electronic devices or channels. Accordingly, the displays of FIGS. 6A, 6B, and 6C can be usable for assessing the status of particular physiology or a particular physiological system of the patient as a whole (for example, cardiac status, pulmonary status, neurological status, or the like) without concern for the source of the measurement data that is being shown. The measurement data can be presented in the form of parameters, trends, waveforms, or the like in the displays.

FIG. 6A illustrates the display of measurement data presented or organized according to hemodynamics for a patient (this display arrangement may be referred to as a hemodynamics screen). An area 602 can denote that the provided measurement data relates to hemodynamics of the patient. FIG. 6A may be presented on the display in response to receipt of a user input, such as via selection of and in a dropdown menu selectable at the area 602 or selection of an organ (for example, the heart) of the graphic of the upper portion of the person corresponding to hemodynamics. The hemodynamics screen may display parameter data from multiple channels such as, for example, third-party monitoring, anesthesia/ventilator, or capnography. This screen can additionally or alternatively display, for example, pleth wavefrom, pressure waveform, flow waveform, or $CO_2$ waveform.

FIG. 6B illustrates the display of measurement data presented or organized according to oxygenation for a patient (this display arrangement may be referred to as an oxygenation screen). An area 604 can denote that the provided measurement data relates to oxygenation of the patient. FIG. 6B may be presented on the display in response to receipt of a user input, such as via selection of and in a dropdown menu selectable at the area 604 or selection of an organ (for example, the lungs) of the graphic of the upper portion of the person corresponding to oxygenation. The oxygenation screen can display parameter data from one or more the following channels: third-party monitoring, anesthesia/ventilator, or capnography. The oxygenation screen can additionally or alternatively display for example, Pleth waveform, pressure waveform, flow waveform, or $CO_2$ waveform. Although some screens, such as the hemodynamics screen and the oxygenation screen, display the similar parameters or waveforms, the layout (for example, the location or size) of some of the waveform data or parameter data may be different between two screen layouts, which can show the different emphasis of each screen layout.

FIG. 6C illustrates the display of measurement data presented or organized according to sedation for a patient (this display arrangement may be referred to as a sedation screen). An area 606 can denote that the provided measurement data relates to sedation of the patient usable to monitor a depth of anesthesia for the patient. FIG. 6C may be presented on the display in response to receipt of a user input, such as via selection of and in a dropdown menu selectable at the area 606 or selection of an organ (for example, the brain) of the graphic of the upper portion of the person corresponding to sedation. The sedation screen can display parameter data from one or more the following channels: third-party monitoring devices, anesthesia/ventilator, capnography, EEG monitoring, or region brain oximetry. The sedation screen can additionally or alternatively display waveforms generated based on data from a EEG monitoring device.

The areas 602, 604, and 606 can be used to cause one of the individual displays of FIGS. 6A, 6B, and 6C to be presented in place of another of the individual displays of FIGS. 6A, 6B, and 6C. In addition, although FIGS. 6A, 6B, and 6C depict measurement data presented or organized according to a care scenario such as hemodynamics, oxygenation, and sedation, the measurement data may additionally or alternatively be presented or organized according to other physiological systems or care scenarios tailored for certain groups care providers. For example, possible care scenarios used for selecting for presentation or organizing the measurement data can include circulation, blood oxygenation and ventilation, brain function and oxygenation, and organ/tissue oxygenation, and possible physiological systems used for selecting for presentation or organizing the measurement data can include organs (such as heart, brain, lungs, pharynx, larynx, lymph nodes, arteries, muscles, spleen, bone marrow, stomach, veins, arteries, pancreas, urinary bladder, kidney, skeleton, intestines, gallbladder, or liver) or organ systems (such as, respiratory system, digestive system, nervous system, muscular system, urinary system, reproductive system, endocrine system, integumentary system, immune system, or circulatory system), among other possibilities.

Further examples of displays and communications in a patient monitoring system are disclosed in U.S. Pat. No. 9,943,269, issued Apr. 17, 2018, titled "SYSTEM FOR DISPLAYING MEDICAL MONITORING DATA," the disclosure of which is hereby incorporated by reference in its entirety. Such displays or features of such displays, for instance, may be presented by the host device 460.

The host device 460 may present a user interface which allows a user to adjust a setting of one or more of the patient devices 430, where a patient parameter data acquired by the patient devices 430 is displayed on a display associated with the host device. For example, the user interface can allow a user to adjust alarm limits of devices that are connected to the hub 100 or to the host device 460 directly via wired or wireless communications.

For example, sliders could be provided as user interface controls on the display of the host device 460, which allow a user to adjust alarm limits or other settings of the one or more of the patient devices 430. Upon receipt of an updated setting, the host device can communicate this setting update to the one or more of the patient devices 430 (for example, over a cable, a network, etc., or via the hub 100). The one or more of the patient devices 430 can know how to read the setting update because the one or more of the patient devices 430 can include code that can interpret the settings update (for example, because the setting update can be formatted in a way, such as by the host device 460, the hub 100, or another device in the computing environment 400, that the one or more of the patient devices 430 can understand it).

The host device 460 can receive an alarm from the one or more of the patient devices 430, the hub 100 (if the host device is connected to the hub directly or via a computer network), or another device in the computing environment 400. The host device 460 can, for example, communicate alarm settings to the hub 100. Based on the alarm settings, the hub 100 can be configured to generate an alert based on the data received from its connected medical devices or sensors and communicate the alert to the display of a host device.

The displays shown in FIGS. 6A, 6B, and 6C can include parameter or window shading (not shown) in gray, parameter or window highlighting (not shown), or parameter or window hiding as described with respect to the display of FIG. 5 so that a caregiver may quickly understand and focus on important information collected and presented by the displays. Moreover, a user may transition between the display depicted in FIG. 5 and one or more of the displays shown in FIGS. 6A, 6B, and 6C and vice versa responsive to a user input, such as via a user selection on one of the displays.

Figure 7:
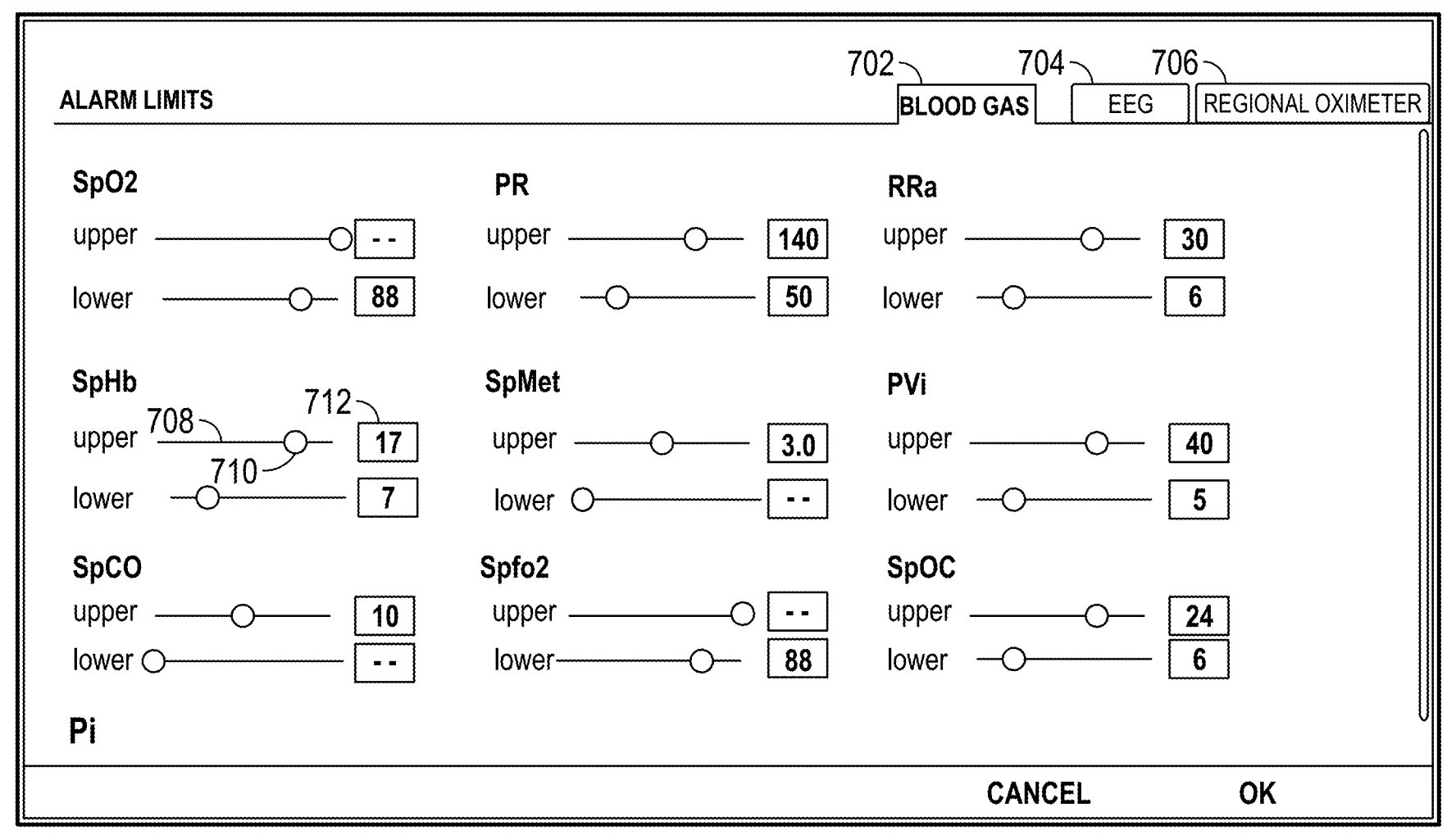

FIG. 7 illustrates controls on a display of a host device, such as the display 476, for adjusting alarm limit ranges of source electronic devices. Tabs 702, 704, 706 can respectively be used to switch between viewing and adjusting alarm limits for the blood gas device, EEG monitoring device, or regional oximetry device. As shown by FIG. 7, when the tab 702 corresponding to the blood gas device may be selected, multiple parameters monitored by the blood gas device can be presented along with corresponding upper and lower ranges for each of the parameters with some upper or lower ranges being unavailable as indicated by "--". The lines and dots, such as a line 708 and a dot 710, can form sliders that are movable by user input to increase the upper and lower alarm limits for the parameters within ranges and may cause generation and transmission of instructions to the blood gas device to appropriately adjust the corresponding alarm limits. To diminish clutter on the display, a value corresponding to a position of a particular slider, such as the slider composed of the line 708 and the dot 710, may not be indicated on the display other than by a value displayed alongside the particular slider, such as at area 712.

Although the display may be shown as being longer than wider, the display instead may have other dimensions like being wider than longer, such as would fit the displays of FIGS. 5, 6A, 6B, 6C, and 7 or such as those on a mobile device.

A user can adjust the setting of a medical device on the hub 100. For example, the hub 100 can present user interface element(s), such as, for example, slider bars to adjust alarm limits of connected medical device. Additional examples of adjusting the setting of a medical device on the hub are also described in U.S. Pat. Appl. Pub. No. 2018/0247712, entitled "SYSTEM FOR DISPLAYING MEDICAL MONITORING DATA", the disclosure of which is hereby incorporated by reference in its entirety.

The user interface controls shown herein are merely illustrative examples and can be varied. For instance, any of the user interface controls shown may be substituted with other types of user interface controls that provide the same or similar functionality. Some examples of user interface controls that may be used include buttons, dropdown boxes, select boxes, text boxes or text fields, checkboxes, radio buttons, toggles, breadcrumbs (for example, identifying a page or interface that is displayed), sliders, search fields, pagination controls, tags, icons, tooltips, progress bars, notifications, message boxes, image carousels, modal windows (such as pop-ups), date or time pickers, accordions (for example, a vertically stacked list with show/hide functionality), and the like. Additional user interface controls not listed here may be used.

Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input (for example, finger or pen), remote control, or keyboard input, among other user interface input options.

Figure 8A:
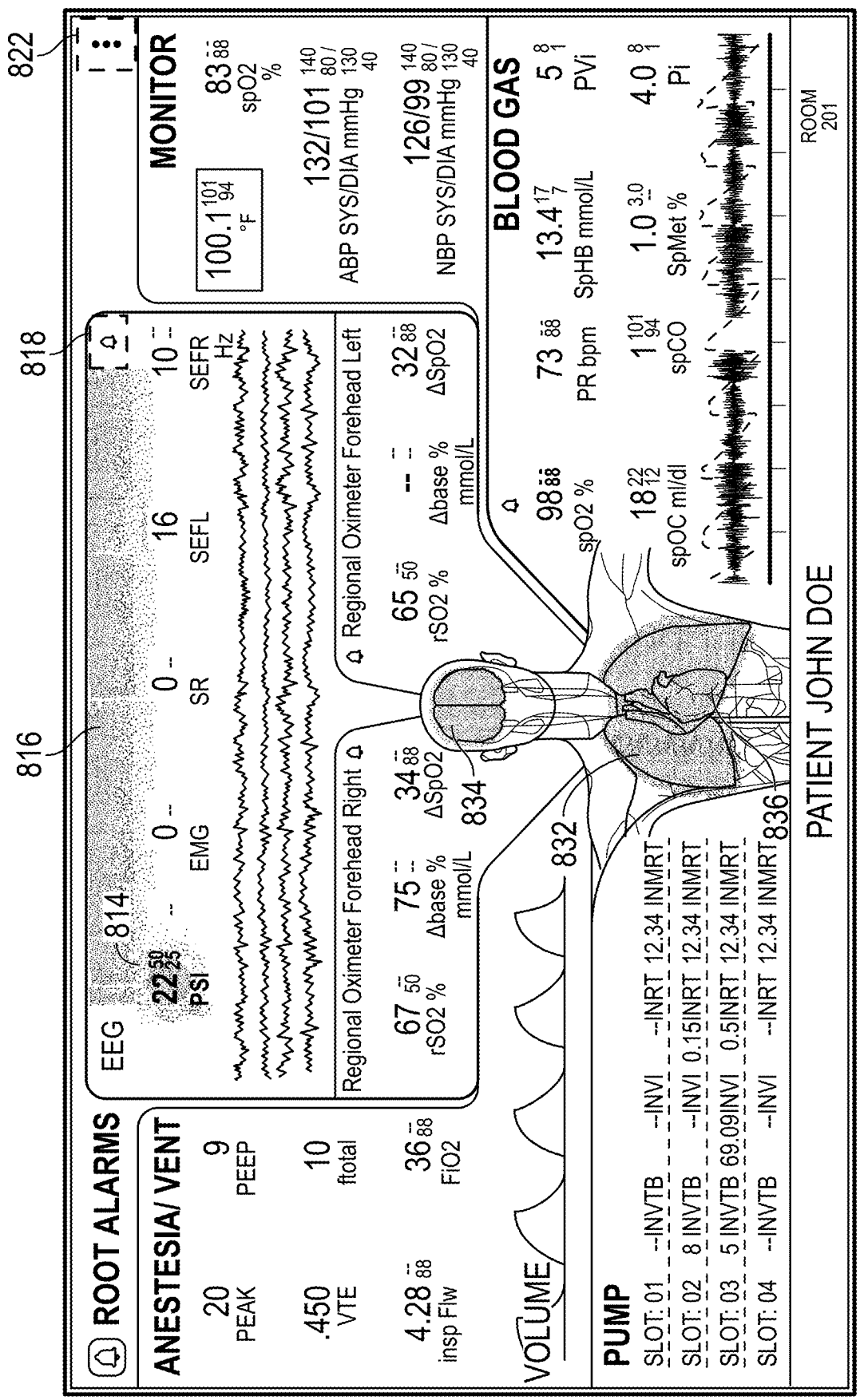
FIGS. 8A and 8B illustrate displays with alarms.

FIG. 8A depicts an area 814 around a displayed EEG parameter value, such as PSi™ value, that can be red indicating an alarm condition for the EEG parameter value, and the brain 834 and an area 816 in a dedicated area labeled EEG monitoring which includes the displayed EEG parameter value can further be red. In addition, an audible alarm may be presented concurrently by the hub 100 or a EEG monitoring device used for monitoring brain activity with presentation of the red on the brain 834, the area 814, and the area 816.

A user of the host device 460 can provide a user input to the host device 460 that causes an audible or visual alarm presented by the host device 460, a source device (for example, one of the patient devices 430), or the hub 100 to be silenced. The host device 460 may moreover silence alarms on any and all devices to which the host device 460 is connected or communicating. When silencing an audible or visual alarm of a source device, an instruction can be generated and transmitted to the source device that causes the source device to silence the audible alarm. For example, the user can provide a user input via selection of an area 418 on the display that causes the audible alarm presented by the hub 100 to be silenced or that an instruction to be generated and sent to the EEG monitoring device to silence the audible alarm.

Figure 8B:
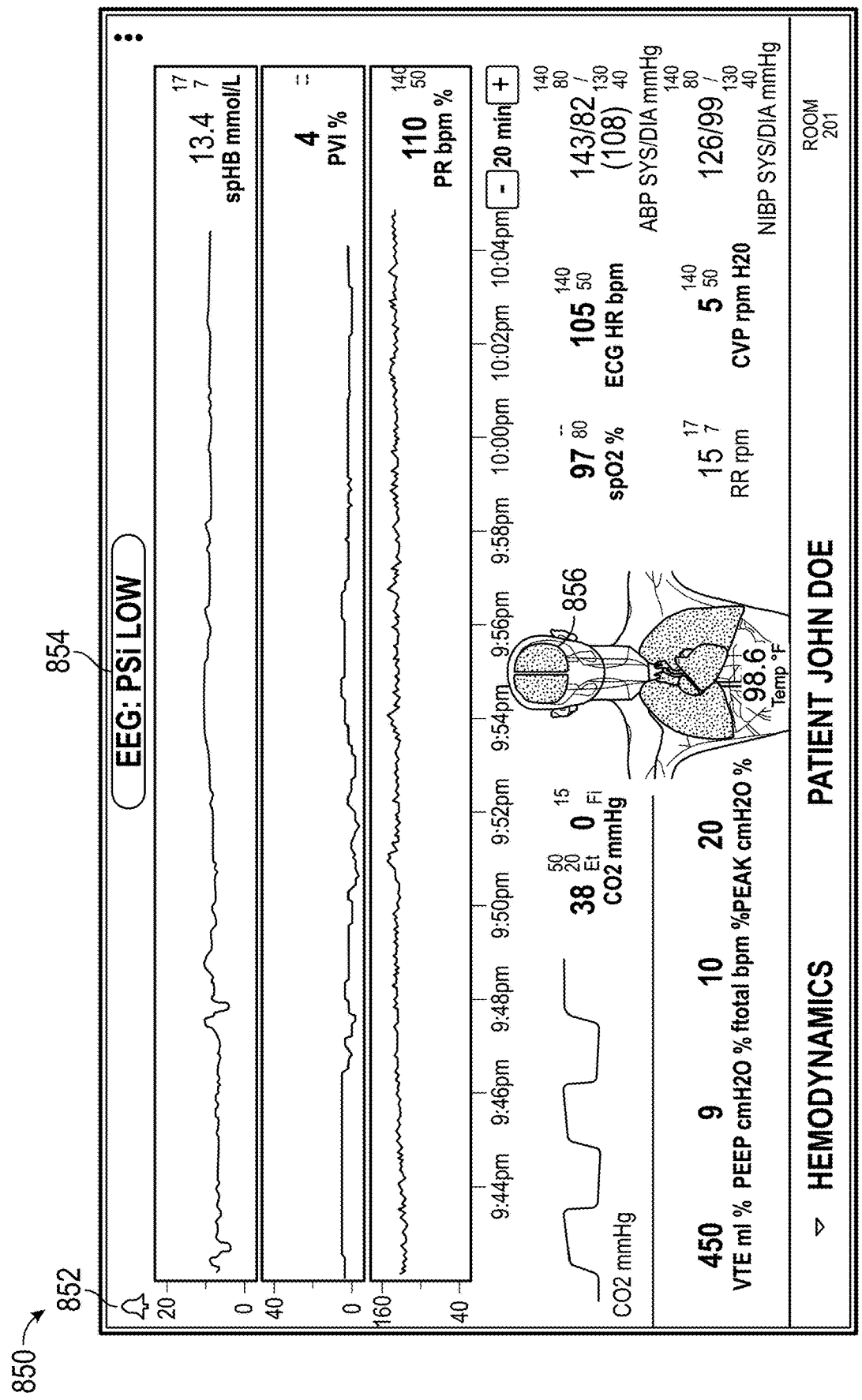

FIG. 8B illustrates a EEG monitoring alarm display 850 where an alarm is presented by the host device 460. In this example, the alarming parameter may not be viewable on the overview screen 500, which may be because the priority of the alarming parameter is relatively lower compared to that of the other parameters being displayed. The EEG monitoring alarm display 850 shows an alarm icon 852 (which may be in red) when an alarm for a parameter is a triggered. In addition to the alarm icon 852, the EEG monitoring alarm display 850 also shows a pill-shaped message 854 at the top-center of the screen indicating the source of the alarming parameter (for example, EEG monitoring) and the parameter that has passed the alarm limit (for example, PSi™). If more than one parameter is alarming, the parameters may be shuffled in the pill-shaped message. The display may provide other visual indications, such as, for example, a red glow pulse behind the pill-shaped message 854 to emphasize the alarm. The EEG monitoring alarm display 850 can also include the organ 856 corresponding to the alarming parameter. For example, the display can change show a red color for an image of the organ 856.

In situations where the alarming parameter is viewable in a screen layout, the display may change the font color of the alarming parameter.

The patient data display system 462 can include an alarm status visualizer which can be configured to show a 3D image of a human body. The 3D image may be present on multiple layout screens, such as those shown in FIGS. 5, 6A, 6B, 6C, and 7. The 3D image can display organ animations and can be color coded for alarm conditions. The animations can be updated based on as the host device 460 receives the values of relevant patient parameters.

Figure 9:
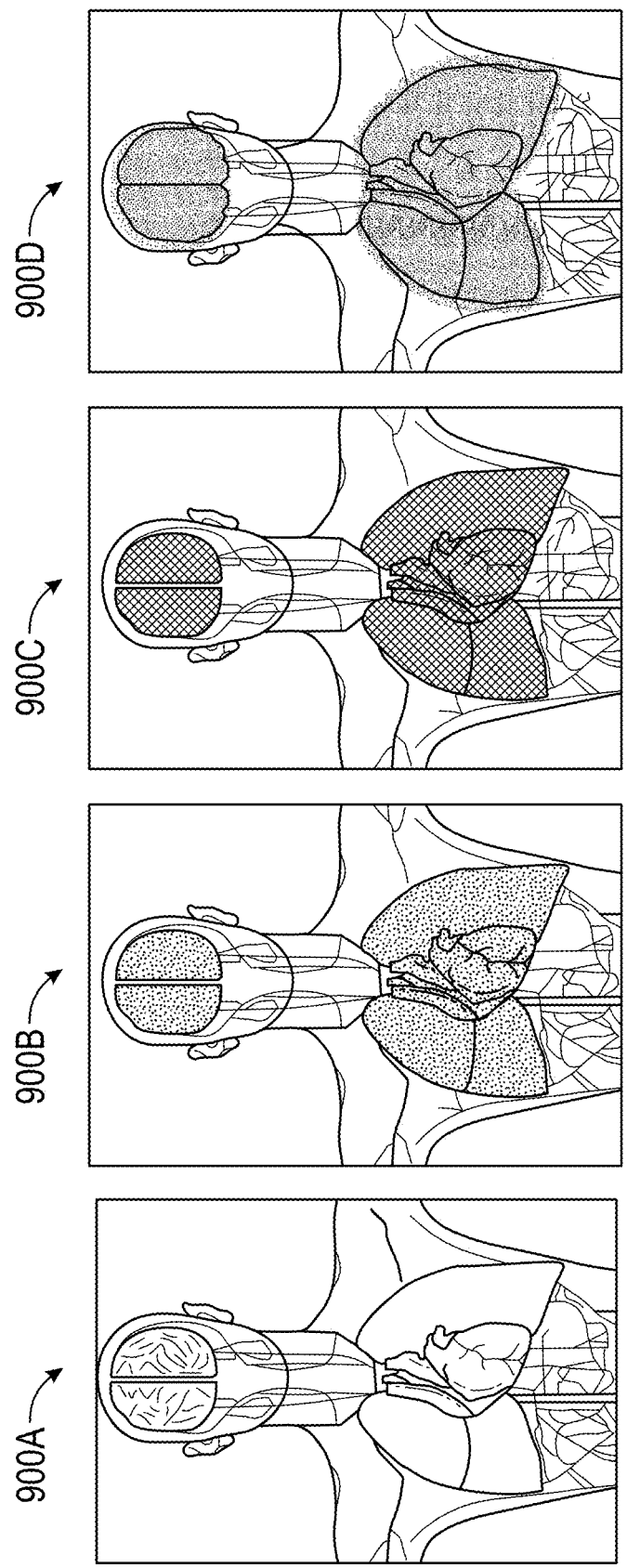
FIG. 9 illustrates animating of a 3D image of a portion of the patient's body based on measurement data.

FIG. 9 illustrates a display of 3D images, such as on the display 476, where certain organs are color coded to represent the status of monitoring and alarm conditions. In this example, the lungs and hearts are highlighted in the views 900B and 900D. The lungs and heart can be animated, for example, based on data collected from sensors associated with the lungs or heart or parameters associated with the lungs or heart. For example, the lungs and heart can be animated based on parameter values, such as those shown in the blood gas window 510 in FIG. 5. The lungs can be animated based on RRa® and RRp® parameter values, and the heart can be animated based on pulse rate (PR) parameter values.

In FIG. 9, four views 900A, 900B, 900C, and 900D are illustrated for different points in time during a monitoring process. In the view 900A, the color of the lungs and the heart is shown in gray, which represents there is no monitoring because the corresponding one or more patient devices 430 is disconnected. The view 900B shows the color of the lungs and the heart in green indicating the successful connection to the one or more patient devices 430 and that the parameters being monitored are in the normal range. The view 900C shows the color of the lungs and the heart in yellow indicating that the statues, notifications, modifiers, notification devices have not been linked to a patient although the one or more patient devices 430 is connected. The view 900D shows the color of the lungs and the heart in red indicating that the parameter is in the alarm range while the one or more patient devices 430 is connected.

Figure 10:
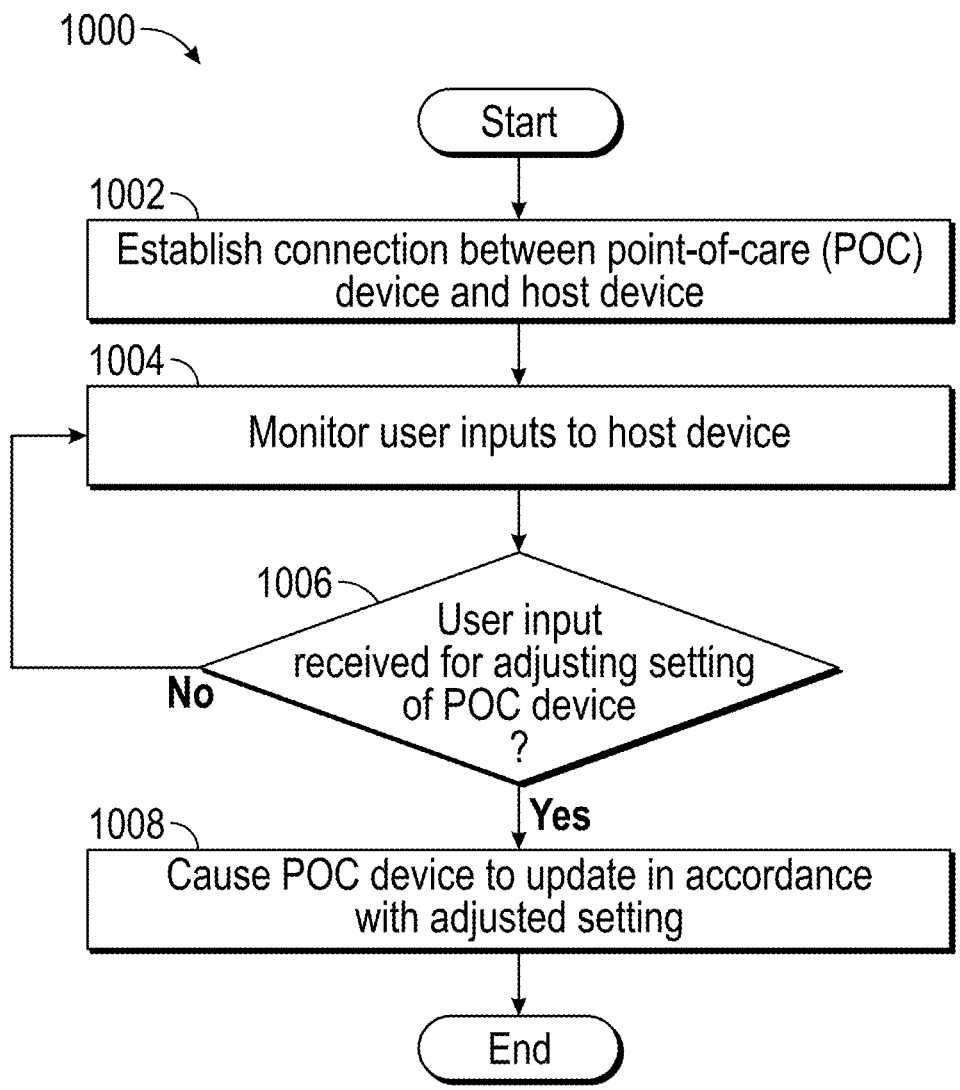
FIG. 10 illustrates an process of adjusting a setting of a patient device via a host device.

FIG. 10A illustrates a process 1000 of adjusting a setting of a PoC device, such as one of the patient devices 430, via a host device, such as the host device 460. The process 1000 may be performed, for instance, by the host device host device 460 or another device described herein. The process 1000 can be programmed as part of the patient data display system 462.

At block 1002, a connection can be established between a PoC device and a host device. For example, one of the patient devices 430 can be connected to the host device 460 directly or via the hub 100.

At block 1004, the host device can monitor user inputs. For example, the host device 460 can determine whether a user has actuated a display of the host device 460, such as the display 464, or another user input device associated with the host device 460.

At block 1006, the host device can determine whether the host device has received a user input for adjusting a setting of the PoC device. For example, a user can adjust a slider bar on the user interface presented by the host device 460 to adjust conditions for triggering an alarm of a patient parameter (for example, whether the value of the patient parameter is above or below a threshold condition). The user interface for adjusting the alarm may be presented in response to a user actuating an user interface element on a patient monitoring screen. As an example, the user can select the menu element 512 on the display 464 to cause the host device 460 to show the user interface screen for adjusting alarm limits for one or more parameters being monitored or for one or more of the patient devices 430 monitored by the host device 460.

If the user input is not received, the process 1000 goes back to the block 1004 where user inputs on the host device are continuously monitored. If the user input is received, at block 1004, the host device can cause the PoC device to update in accordance with the adjusted setting. For example, where an alarm limit is adjust by the user, the one of the patient devices 430 can communicate the adjusted limit to the PoC device (either directly or through the hub 100) which will cause the one of the patient devices 430 to generate an alarm of the associated patient parameter(s) based on the adjusted limit.

Figure 11:
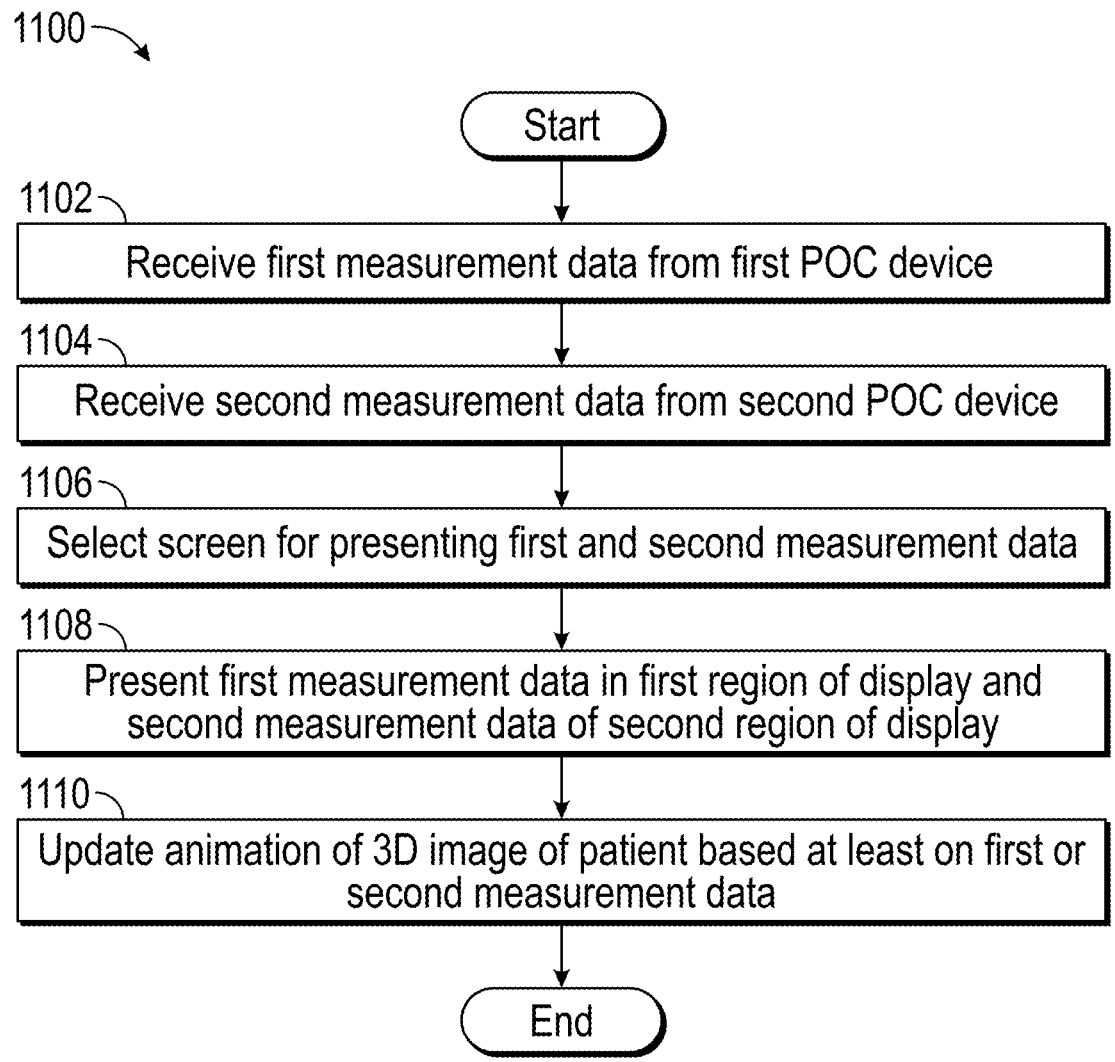
FIG. 11 illustrates a process of presenting patient measurement data on a display associated with a host device.

FIG. 11 illustrates a process 1100 of presenting patient measurement data on a display associated with a host device. The process 1100 can, for instance, be performed by the host device 460 or another device described herein and be programmed as part of the patient data display system 462.

At block 1102, the host device can receive first measurement data gathered by a first PoC device, such as one of the patient devices 430.

At block 1104, the host device can receive second measurement data gathered by a second PoC device, such as another of the patient devices 430. The host device 460 can communicate with the first PoC device or the second PoC device directly (for example, via wired or wireless communications) or indirectly (such as, for example, through the hub 100 or another device disclosed herein).

At block 1106, a screen for the host device can be selected for presenting the first measurement data and second measurement data. The screen may be selected based on the types of devices being connected to the host device 460 for display, the types of parameters being displayed, or the priorities of types of measurement data, etc.

At block 1108, the host device can present the first measurement data in the first region of the display and present the second measurement data in the second region of the display. As a result, the host device 460 can group data based on a clinical scenario, use-case, or physiological system for a patient.

At block 1110, the host device can update an animation of a 3D image of a patient based at least on the first measurement data or the second measurement data. For example, the 3D image may include a portion of the user's brain or lungs. The animations of the brain or lungs may change color from green to red in response to a determination that an alarm is triggered based on the first or second data.

Interface Customization

The layouts of the displays described herein can be customized by users, such as clinicians or other non-clinician users. The layouts, for instance, can be populated in part or fully with user-selected data presentation modules (sometimes referred to as containers or display elements) that together cover part or all of a particular layout of the display. The populated layout may then receive measurement data from one or more devices and present or animate based on measurement data. In this way, the presentation of information by the displays can be tailored for types of caregivers, procedures being performed, user preferences, or the like.

Figure 12:
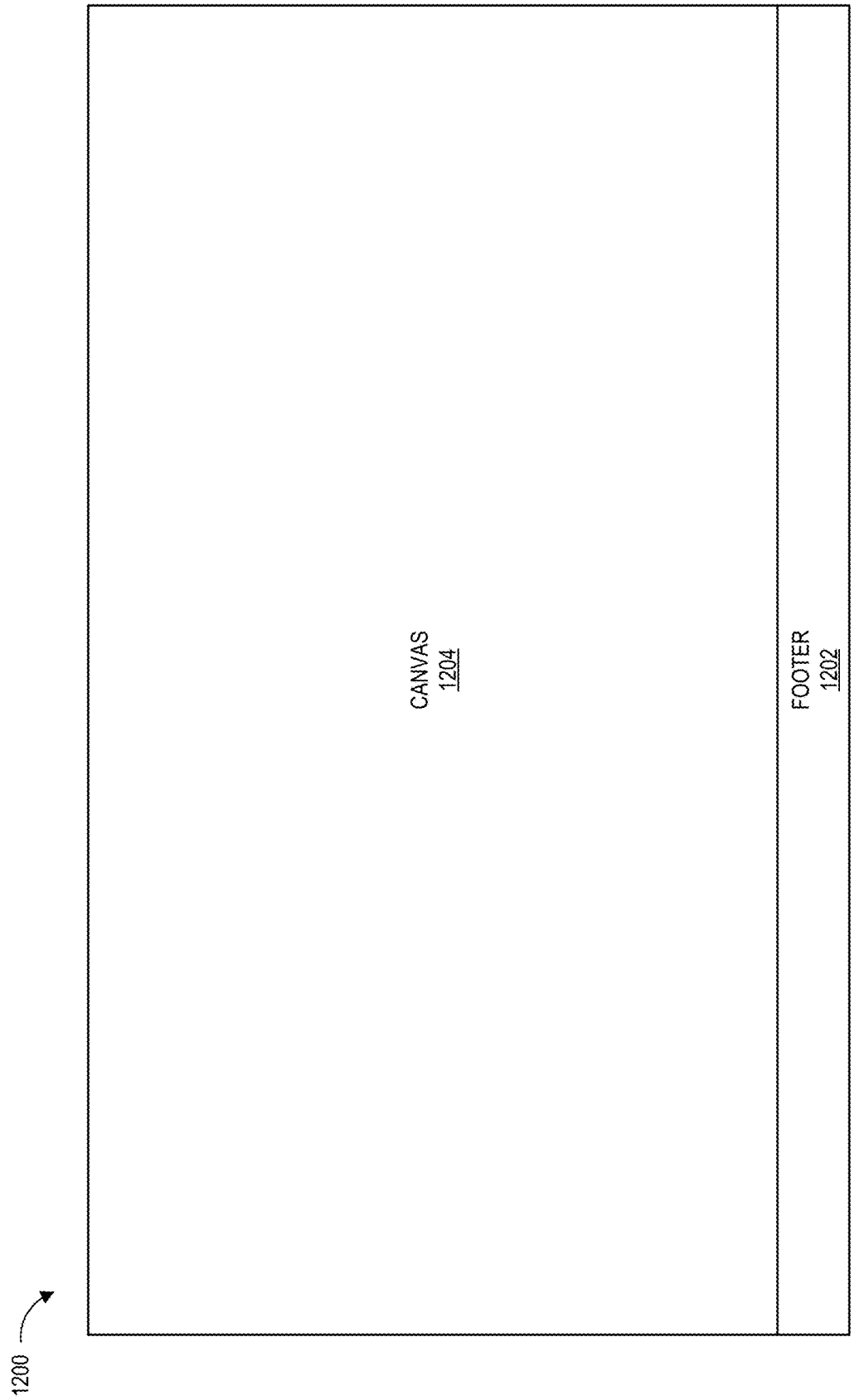
FIG. 12 illustrates areas on a display for presenting information including measurement data.

FIG. 12 illustrates an empty screen 1200 on a display of a host device, such as the display 476, for presenting information. The empty screen 1200 can be divided into two areas including a footer 1202 and a canvas 1204. As shown in the examples of FIGS. 5, 6A-6C, 7, and 8 and elsewhere herein, the footer 1202 can include an identifier for a patient, an identifier for a room in a physical treatment facility in which the patient is being treated, or an identifier for a physiological system or a template corresponding to the display of information on the canvas 1204, among other information or interface controls. The canvas 1204 can present various measurement data as, for instance, shown in FIGS. 5, 6A-6C, 7, and 8 or elsewhere herein, among other information or interface controls.

In one example, the canvas 1204 can be divided into 25 rows of squares where each square may have a height of around 4% of a height of the canvas 1204. The canvas 1204 can include 48 squares per row with each square's width being around 2.1% of a width of the canvas 1204. For a resolution of 1280×1920, each square may be 40×40 pixels. In other examples, the canvas 1204 can be divided into a different number of rows, a different size of squares or other shapes, or a different number of squares per row. One or more outer rows or columns may or may not include measurement data or user interface controls.

Figure 13:
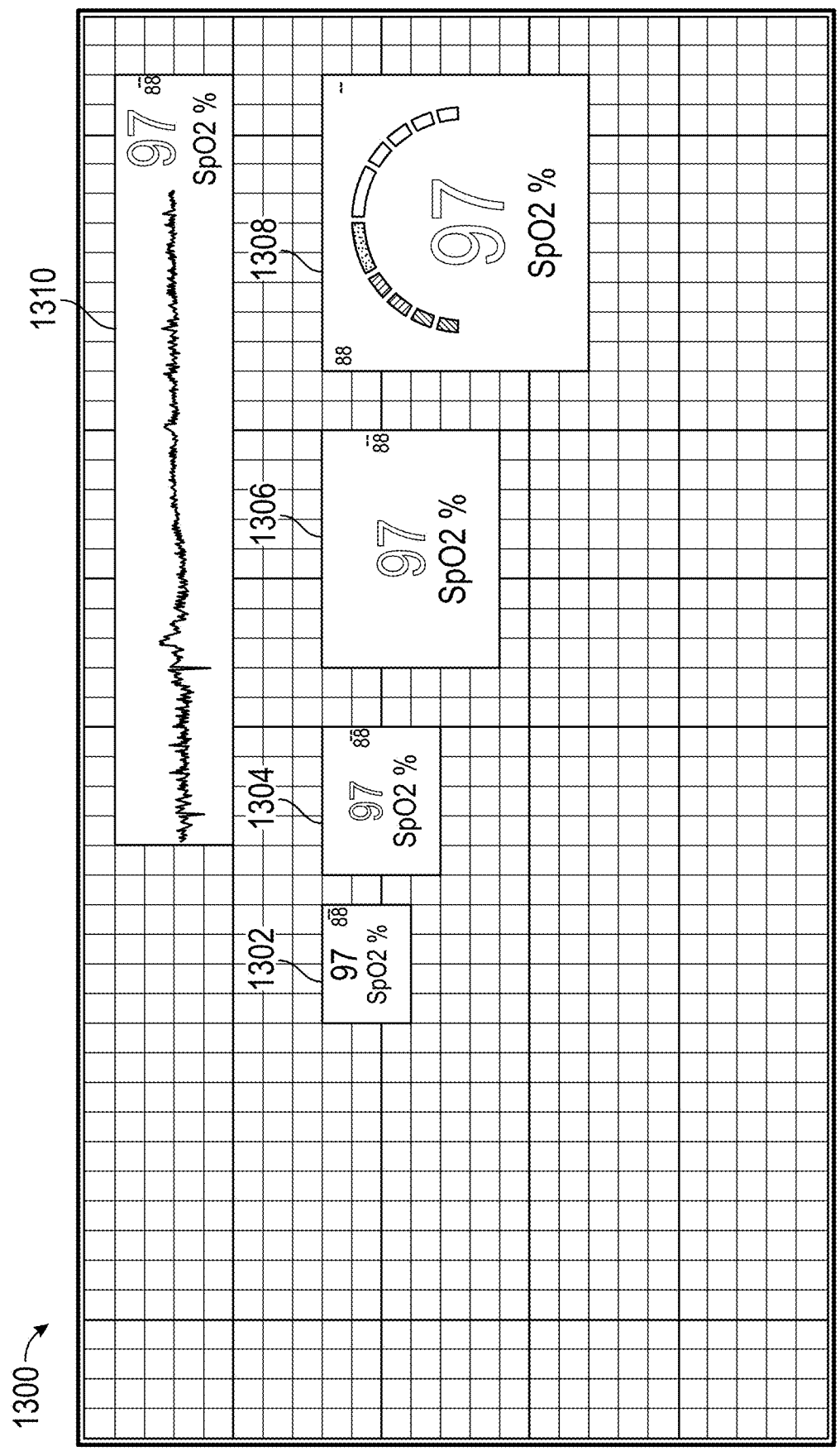
FIG. 13 illustrates bounding boxes on a display.

FIG. 13 illustrates a bounding box screen 1300 on a display of a host device, such as the display 476. The bounding box screen 1300 can include bounding boxes 1302, 1304, 1306, 1308, 1310 that are positioned around numerical values, gauges, or trends for particular measurement data, as well as include an identifier that indicates a parameter associated with the measurement data displayed by a particular one of the bounding boxes 1302, 1304, 1306, 1308, 1310. The bounding boxes 1302, 1304, 1306, 1308, 1310 can be moved around by on the display by a user (for example, by a drag and drop action), aligned by the display to the gridlines on the bounding box screen 1300, and non-overlapping with one another so that the bounding box screen 1300 is arranged and organized. The bounding boxes 1302, 1304, 1306, 1308, 1310 may be permitted to overlap in some instances. The bounding boxes 1302, 1304, 1306, 1308, 1310 may be moved in a configuration mode (for example, a mode when not presenting measurement data of a patient) but not an operation mode (for example, a mode when presenting measurement data of a patient) or may be moved in any mode. Although SpO2% may be shown as the associated parameter for all of the bounding boxes 1302, 1304, 1306, 1308, 1310, this is merely for illustrative purposes and other parameters described herein or yet other parameters may be presented via the bounding boxes 1302, 1304, 1306, 1308, 1310.

Figure 14:
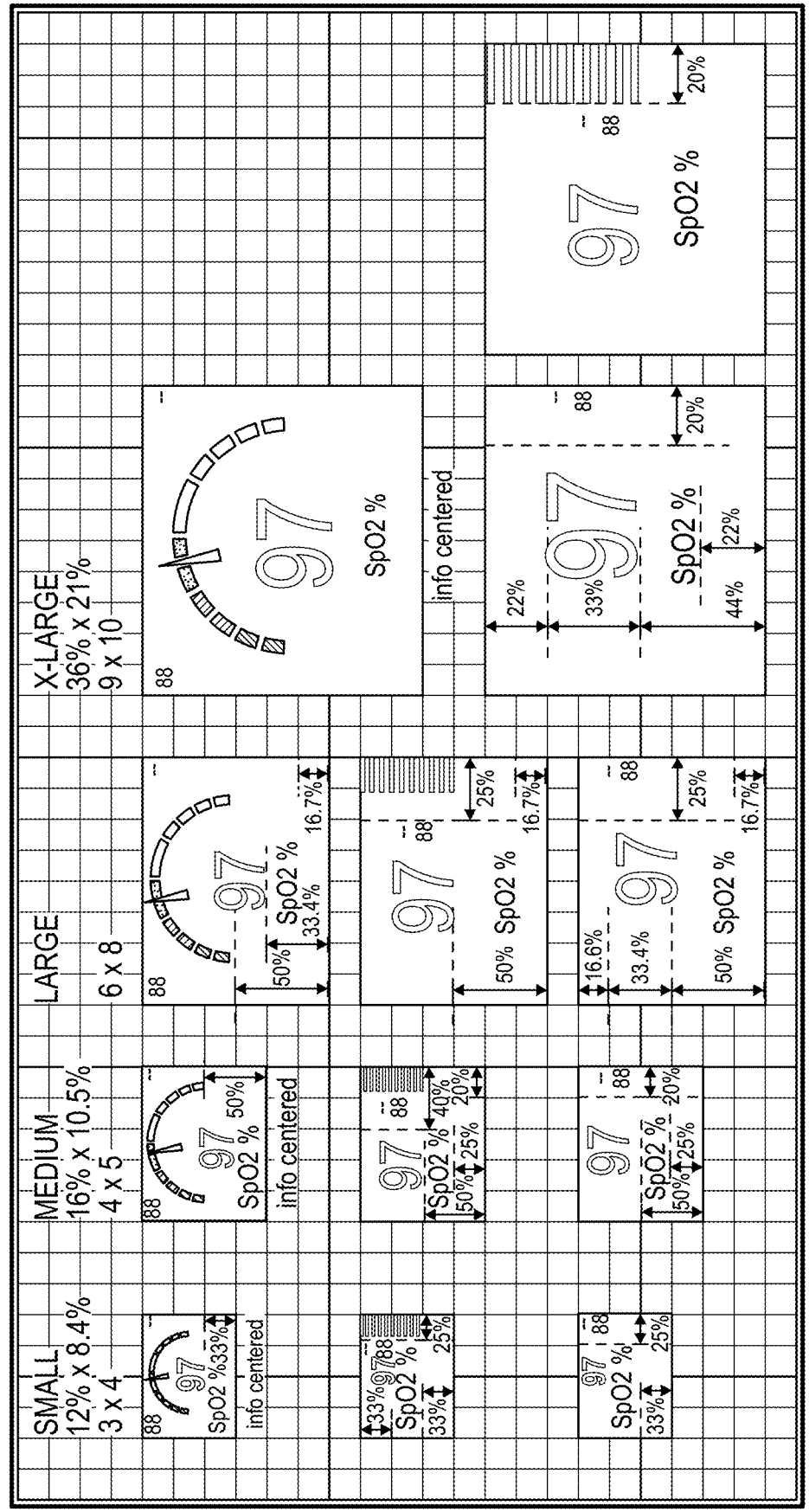
FIG. 14 illustrates parameter containers on a display for presenting measurement data.

FIG. 14 illustrates a parameter container screen 1400 on a display of a host device, such as the display 476. The parameter container screen 1400 can include parameter containers that are various sizes, such as small, medium, large, or extra-large. The parameter containers can present measurement data in various different forms or in various different formats. The spacing between certain elements of the parameter container screen 1400 is shown as a percentage of a particular parameter container. The size of certain elements of the parameter container screen 1400 is shown as a number of squares of the background grid. The parameter containers can each be surrounded by a bounding box as described with respect to FIG. 13 and may be moved around a layout of the display by a user.

Figure 15A:
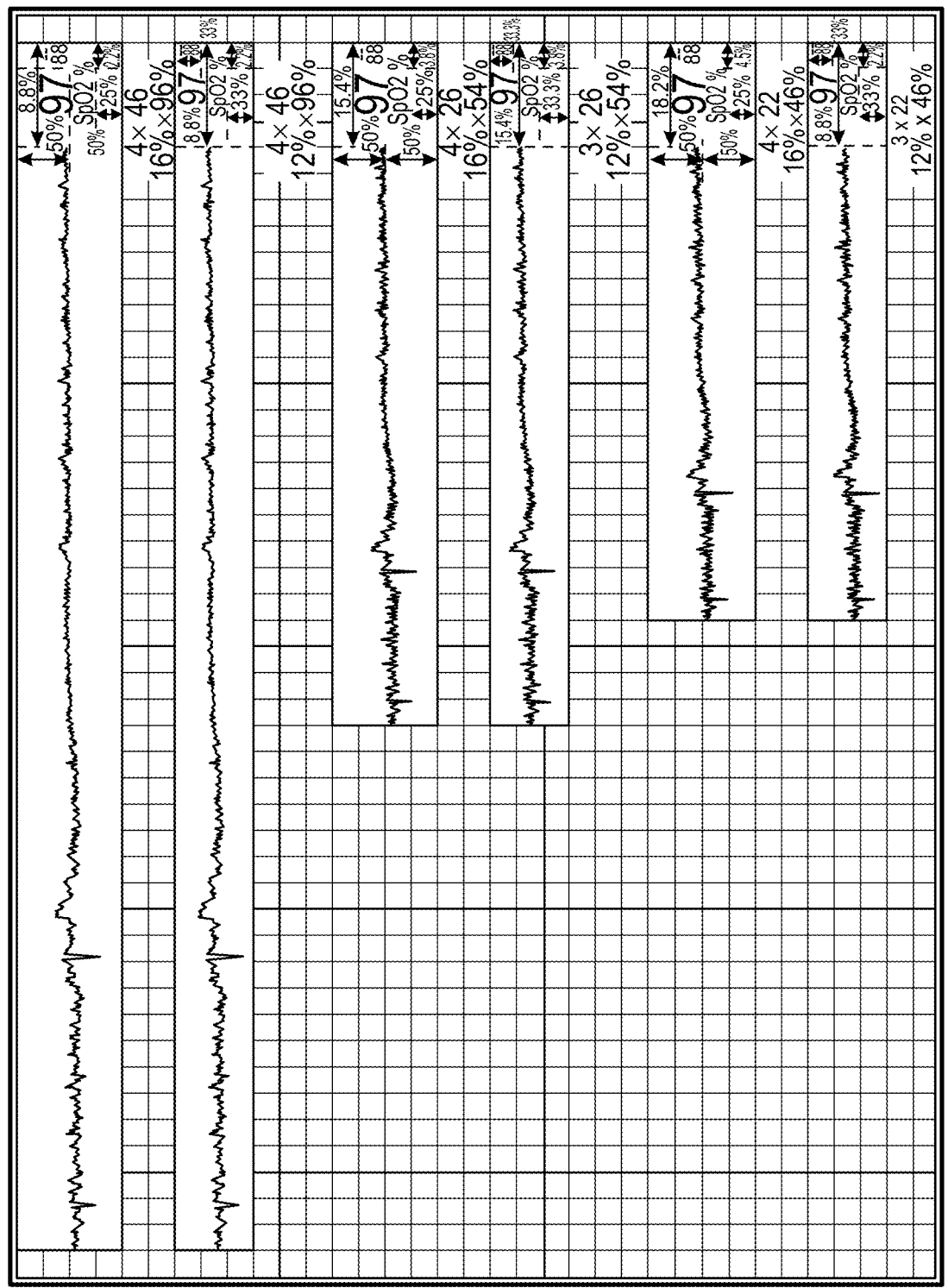
FIGS. 15A and 15B illustrate trend containers on a display for presenting measurement data.
Figure 15B:
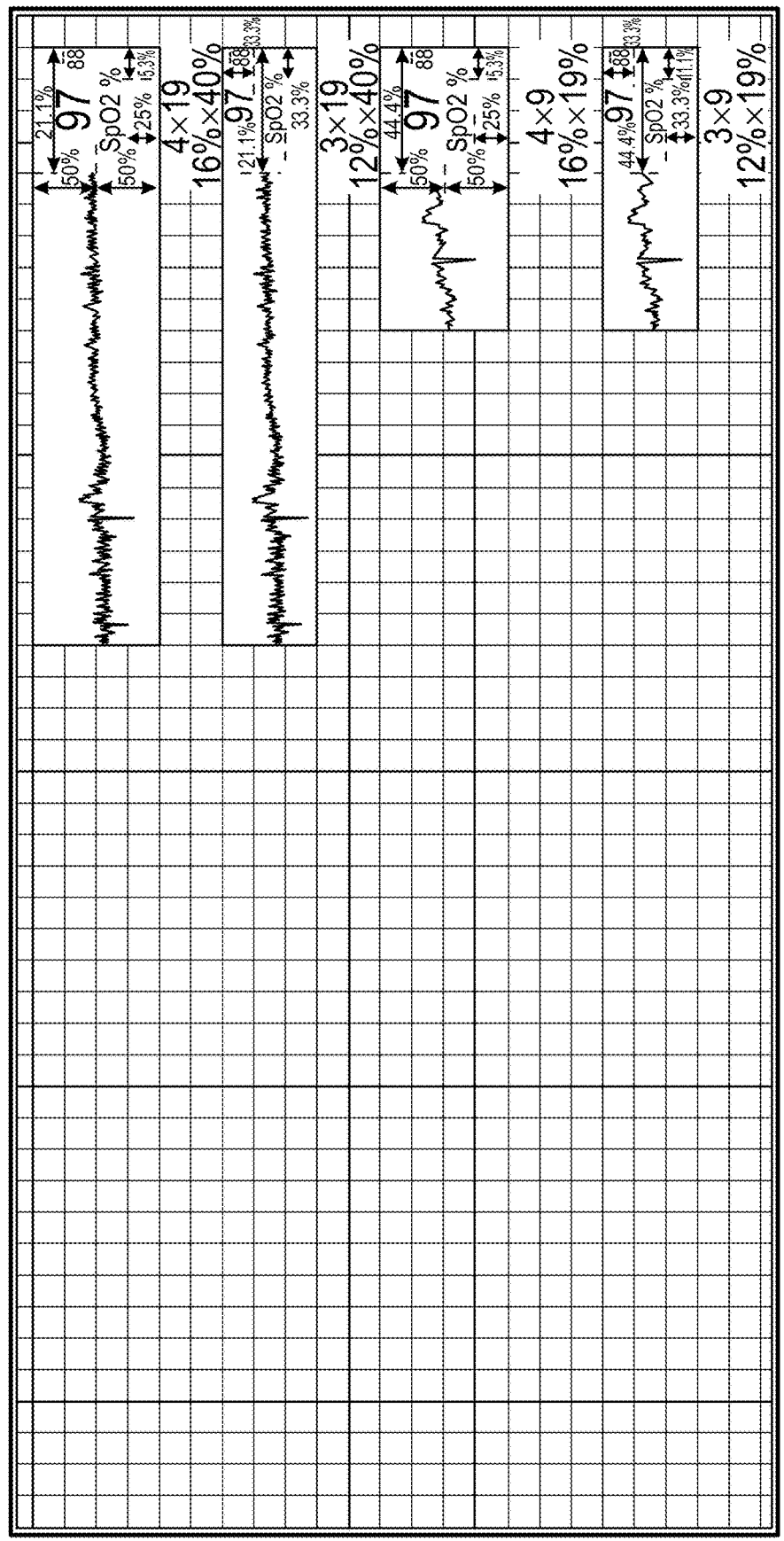

FIGS. 15A and 15B illustrate trend container screens 1500A, 1500B on a display of a host device, such as the display 476. The trend container screens 1500A, 1500B can include trend containers that are various sizes, such as extra-small tall or short, small tall or short, medium tall or short, large tall or short, or extra-large tall or short. The parameter containers can present measurement data in various different forms or in various different formats. The spacing between or size of certain elements of the trend container screens 1500A, 1500B is shown as a percentage of a particular parameter container. The size of certain elements of the trend container screens 1500A, 1500B is shown as a number of squares of the background grid. The trend containers can each be surrounded by a bounding box as described with respect to FIG. 13 and may be moved around a layout of the display by a user.

Figure 16:
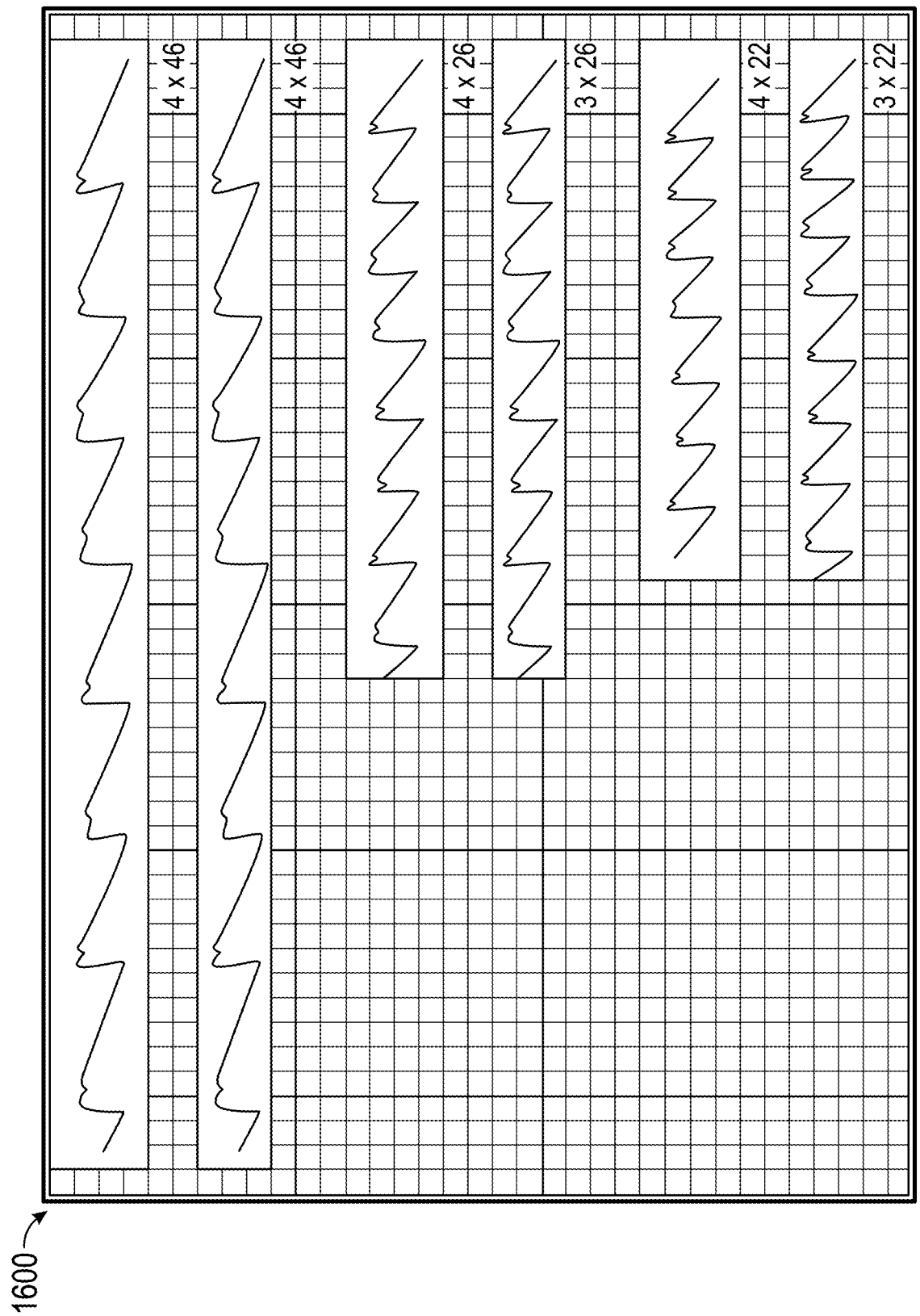
FIG. 16 illustrates waveform containers on a display for presenting measurement data.

FIG. 16 illustrates a waveform container screen 1600 on a display of a host device, such as the display 476. The waveform container screen 1600 can include waveform containers that are various sizes, such as small tall or short, medium tall or short, or large tall or short. The waveform containers can present measurement data in various different forms or in various different formats. The size of certain elements of the waveform container screen 1600 is shown as a number of squares of the background grid. The waveform containers can each be surrounded by a bounding box as described with respect to FIG. 13 and may be moved around a layout of the display by a user.

Figure 17:
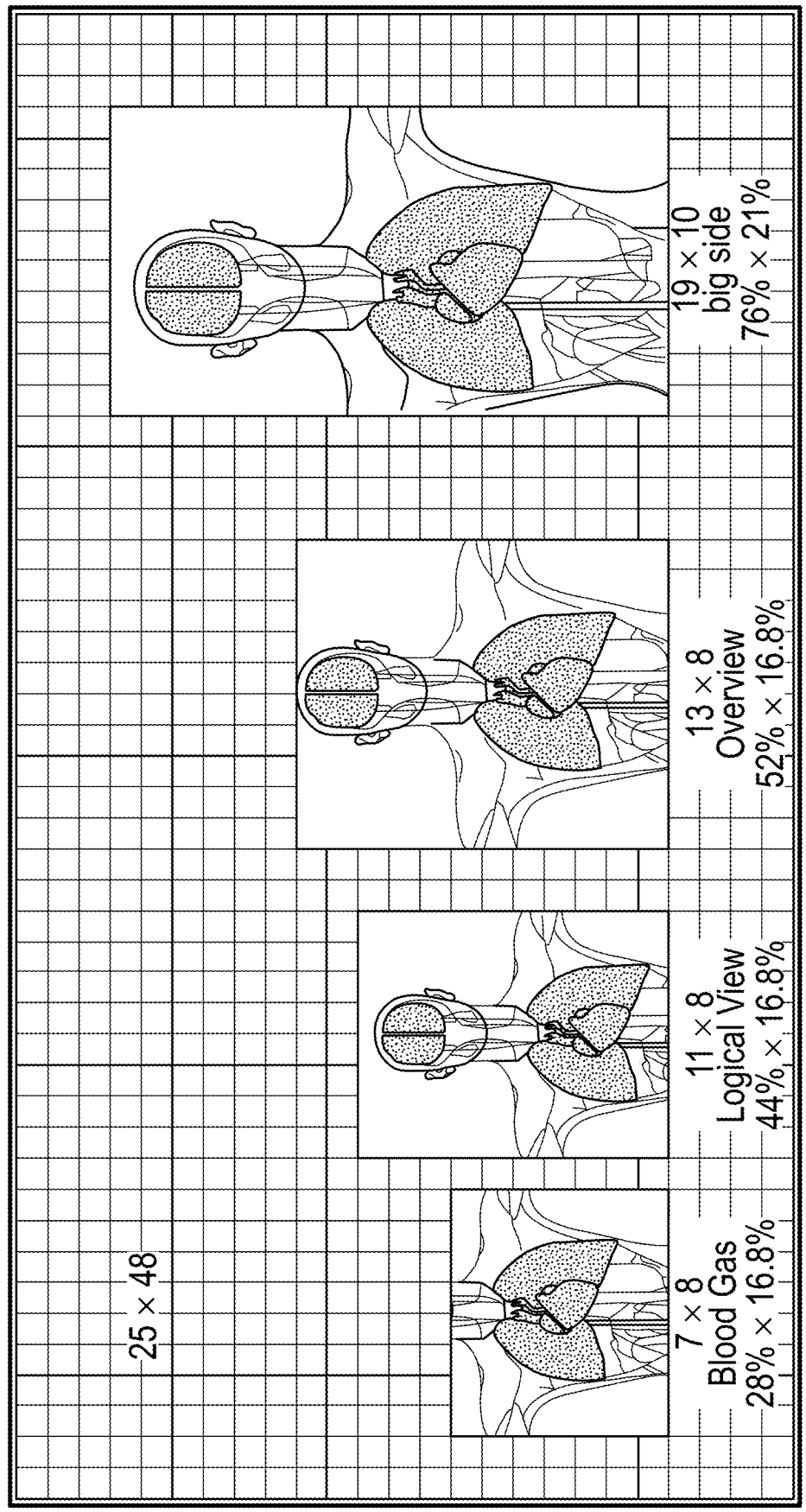
FIG. 17 illustrates human body image containers on a display.

FIG. 17 illustrates a human body image container screen 1700 on a display of a host device, such as the display 476. The human body image container screen 1700 can include human body image containers that are various sizes, such as small, medium, large, or extra-large. The human body image containers can present measurement data or alarms in various different forms or in various different formats, such as is described elsewhere herein. The size of certain elements of the human body image container screen 1700 is shown as a number of squares of the background grid. The human body image containers can each be surrounded by a bounding box as described with respect to FIG. 13 and may be moved around a layout of the display by a user.

Figure 18A:

FIG. 18A illustrates a template selection screen 1800A for selection of a template for presentation on a display of a host device, such as the display 476. The template selection screen 1800A can include templates 1802, 1804, 1806, 1808, 1810, 1812, 1814. As can be seen, the template 1808 can be selected in FIG. 18A and displayed in the area above the templates 1802, 1804, 1806, 1808, 1810, 1812, 1814. The templates 1802, 1804, 1806, 1808, 1810, 1812, 1814 can include different numbers or types of containers from one another and may have different formats or organizations from one another.

Figure 18B:
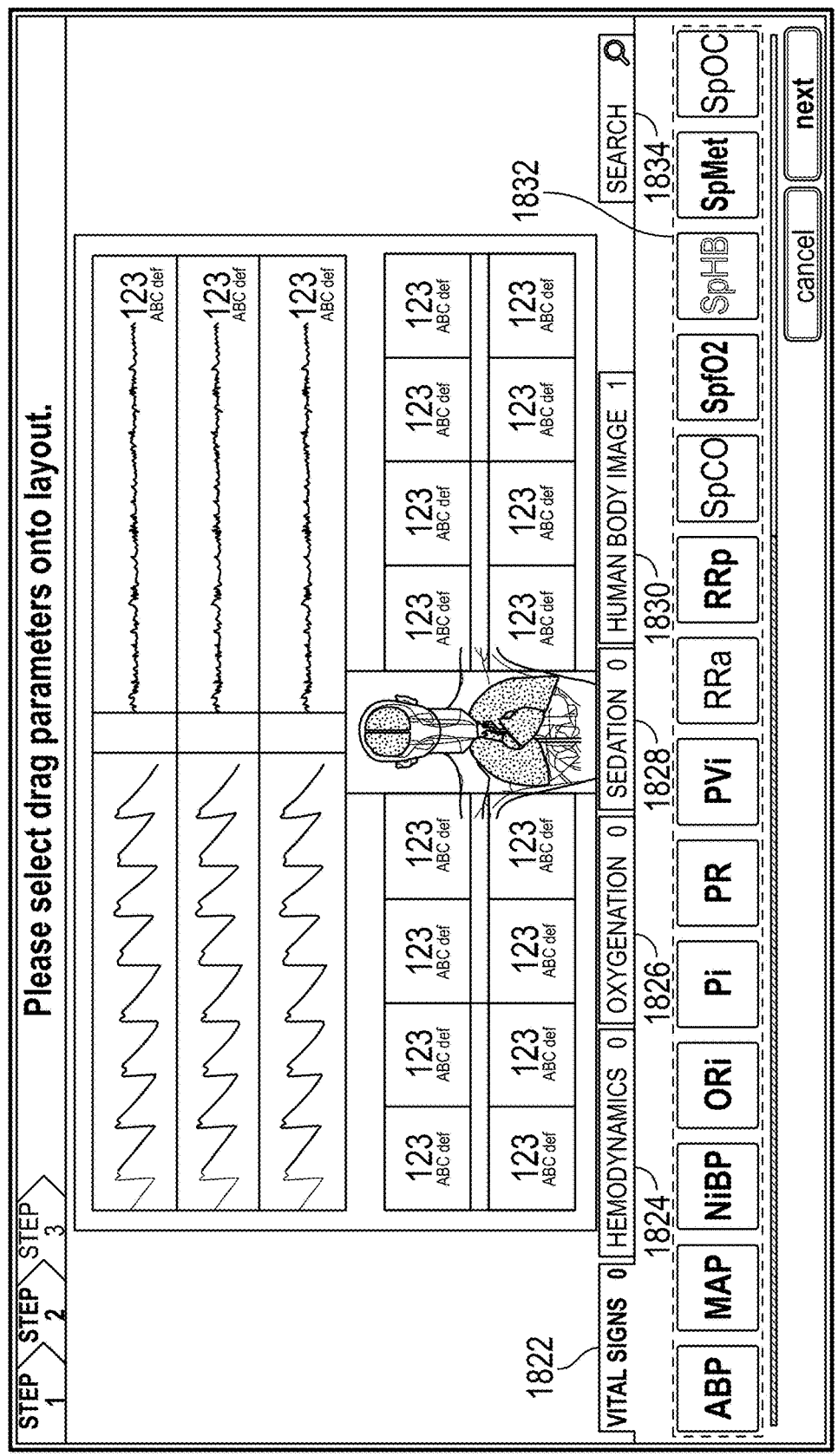

FIG. 18B illustrates a layout screen 1800B for configuration of a display of a host device, such as the display 476. The layout screen 1800B can include a vital signs tab 1822, a hemodynamics tab 1824, a oxygenation tab 1826, a sedation tab 1828, a human body image tab 1830, a parameter selection area 1832, and a search area 1834. The vital signs tab 1822, the hemodynamics tab 1824, the oxygenation tab 1826, the sedation tab 1828, and the human body image tab 1830 can permit a user to adjust the parameters or measurement data that are displayed for the corresponding screens by selection from the parameter selection area 1832 or parameter searching via the search area 1834.

Figure 18C:

FIG. 18C illustrates a layout construction screen 1800C for configuration of a display of a host device, such as the display 476. The layout construction screen 1800C can include a pulse rate container 1840 and a container slot 1842. As illustrated, a user can drag the pulse rate container 1840 from a pulse rate selection area 1844 and drop pulse rate container 1840 in the container slot 1842 to include the pulse rate container 1840 as part of the layout of the screen at the container slot 1842.

Figure 18D:

FIG. 18D illustrates a setting modification screen 1800D for configuration of a display of a host device, such as the display 476. The setting modification screen 1800D can include settings interface elements 1850 for adjusting format settings associated with presentation measurement data in an added pulse rate container 1852. The settings interface elements 1850 can include a numeric change element (for example, to select a formatting of a number presented by the added pulse rate container 1852), a small change element (for example, to select a size of data presented by the added pulse rate container 1852), a color change element (for example, to select a color of information presented by the added pulse rate container 1852), a details display element (for example, to select or configure a source, priority, or order of data presented by the added pulse rate container 1852), and a remove element (for example, to delete the added pulse rate container 1852 from the current layout). The details display element can, in one implementation, be used to prefer one manufacturer or source of data over other so that, for instance, PR derived from oximeter data is preferred to PR derived from acoustic data and accordingly presented first if available or determined to be of a sufficient quality level. The settings interface elements 1850 can be similarly presented and used to configure other added containers on the current layout.

Figure 18E:
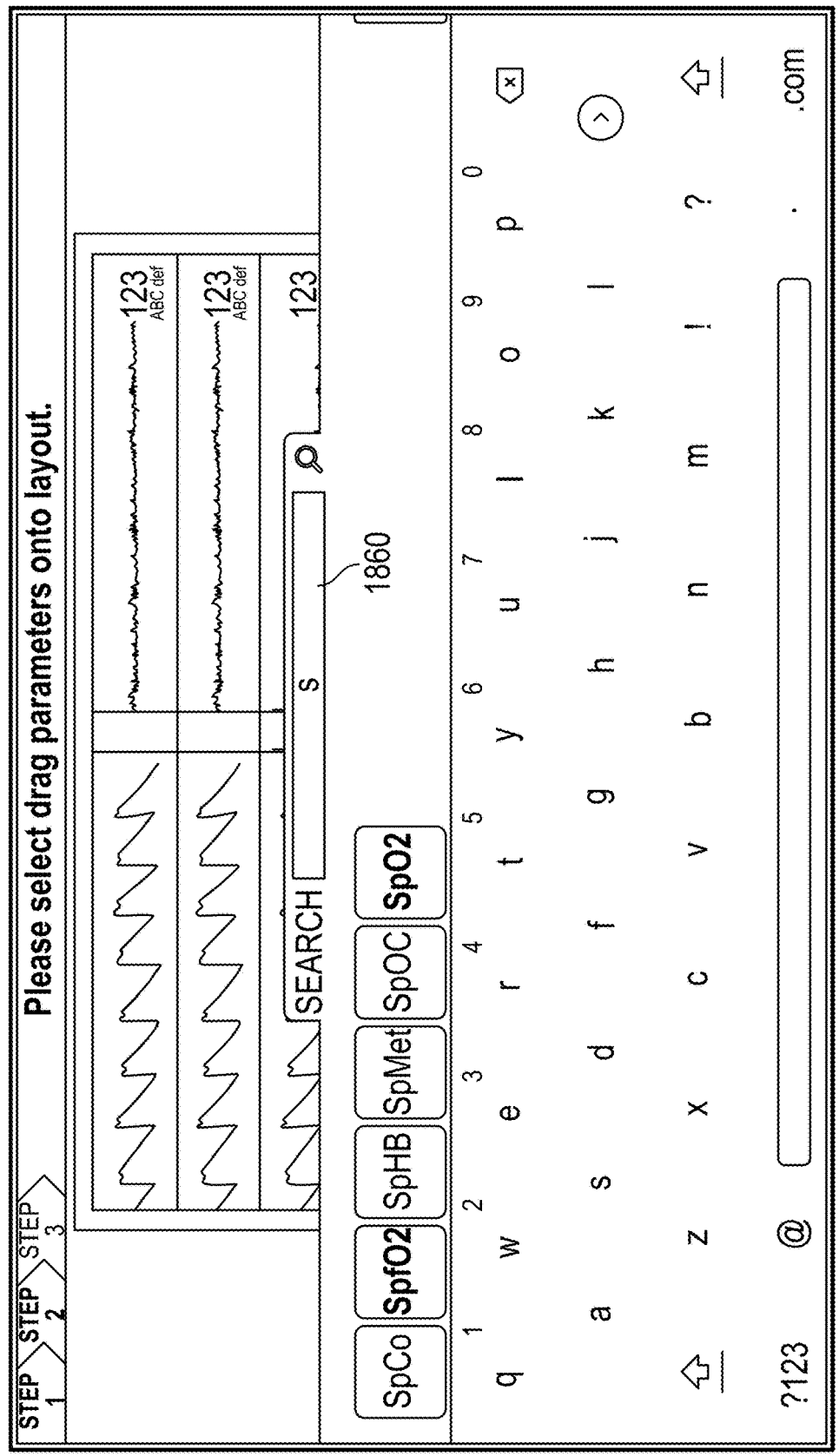

FIG. 18E illustrates a selection search screen 1800E for configuration of a display of a host device, such as the display 476. The selection search screen 1800E can include a search control area 1860 for searching for parameters that may be displayed as part of a particular screen or template. The selection search screen 1800E can, for example, appear upon selection of the search area 1834 of the layout screen 1800B.

Figure 19:
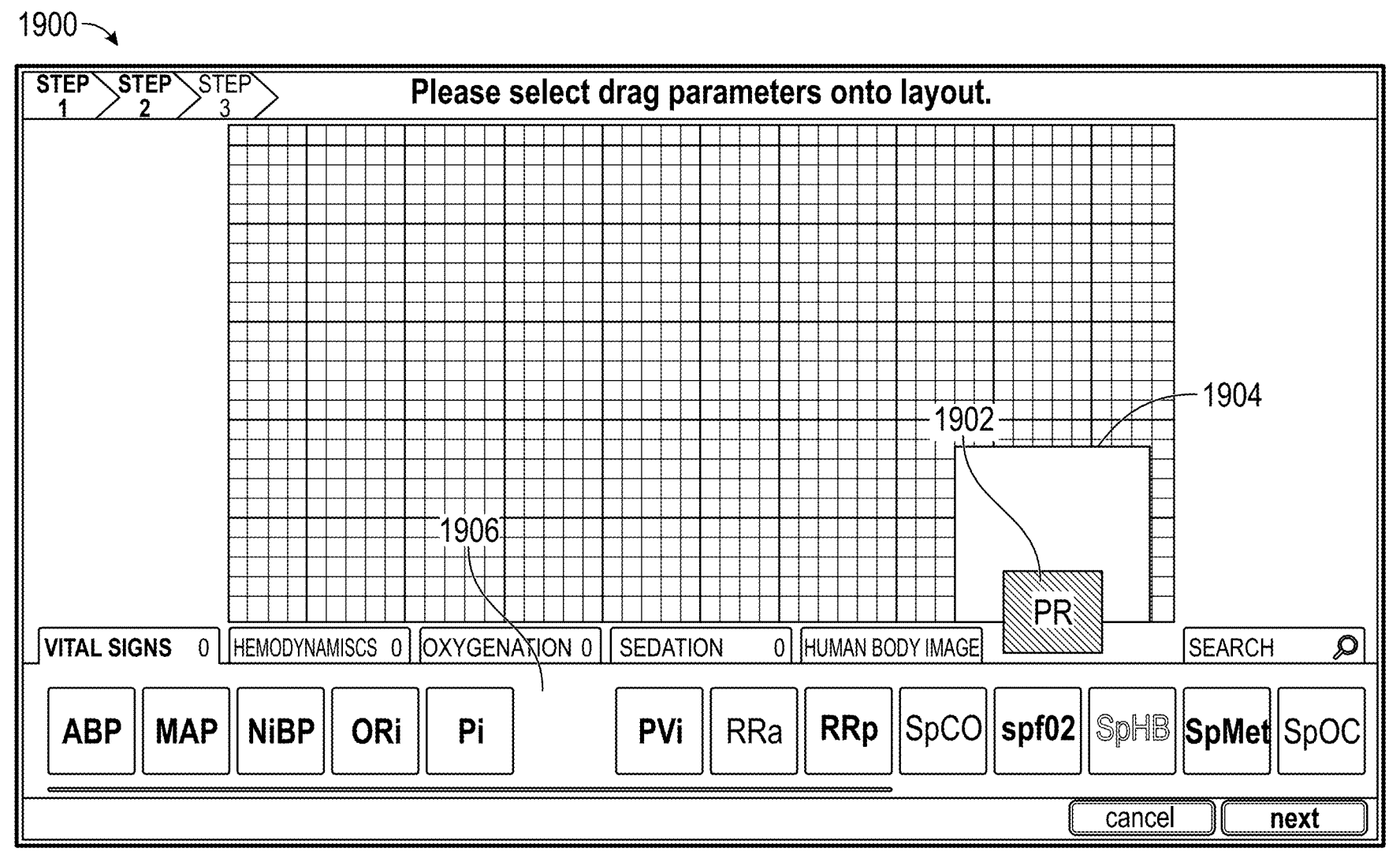

FIG. 19 illustrates another layout construction screen 1900 for configuration of a display of a host device, such as the display 476. The another layout construction screen 1900 can include a pulse rate container 1902 and a container slot 1904. As illustrated, a user can drag the pulse rate container 1902 from a pulse rate selection area 1906 and drop pulse rate container 1902 in the container slot 1904 to include the pulse rate container 1902 as part of the layout of the screen at the container slot 1904. The container slot 1904 can be presented in an empty background template, such as by selection of the template 1814 on the template selection screen 1800A.

Figure 20:
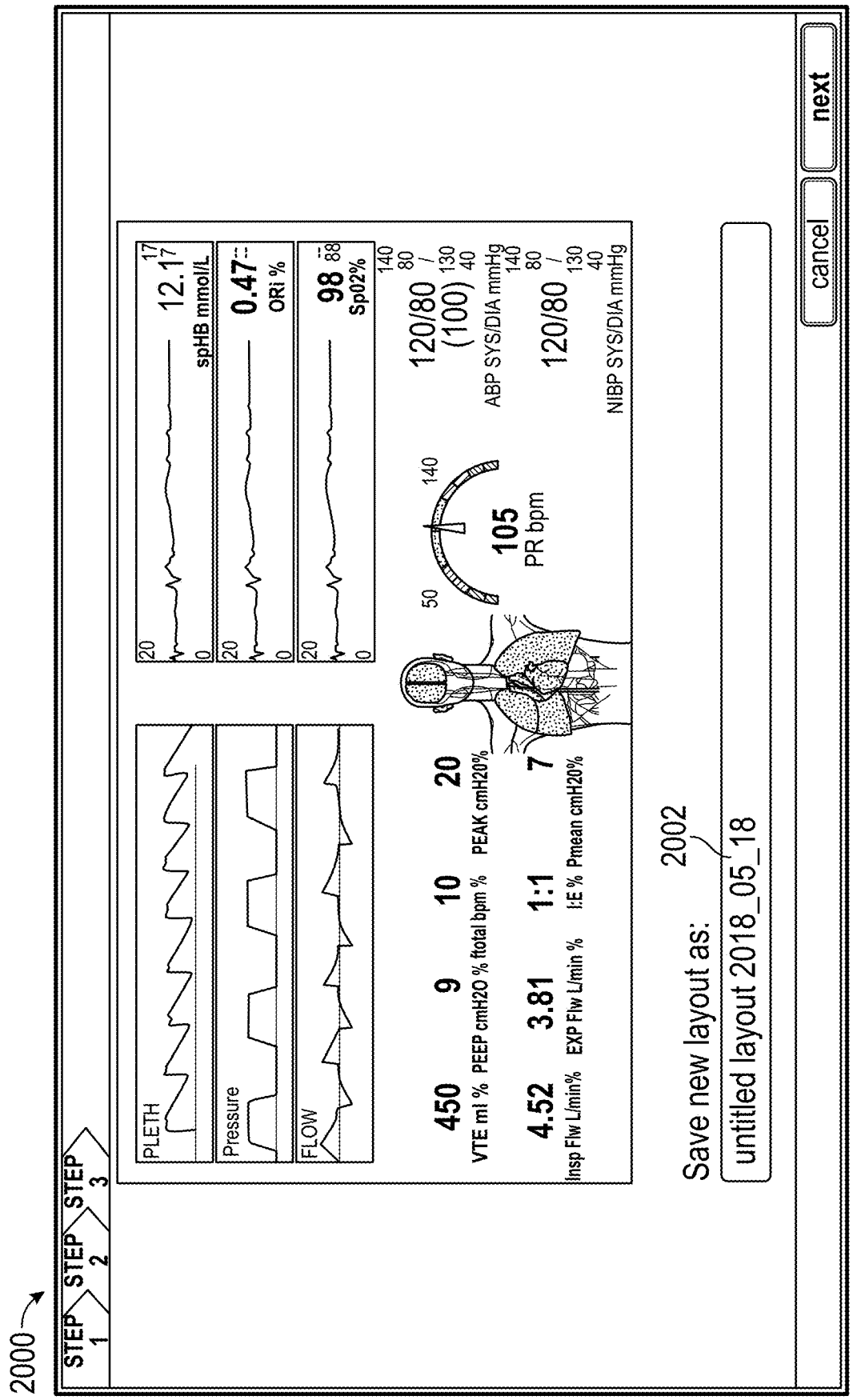
Figure 21:
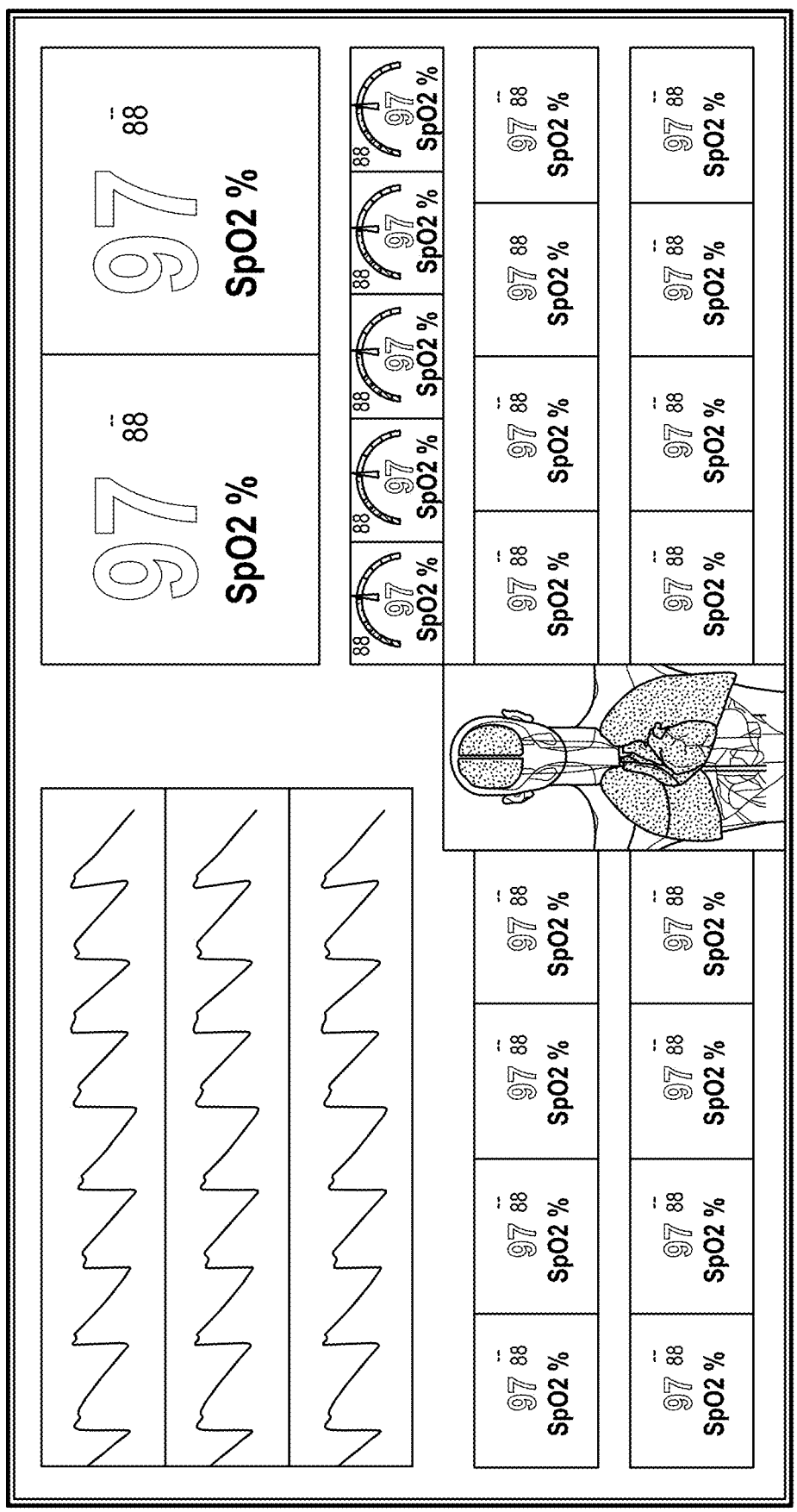
FIGS. 21, 22, 23, 24, 25, 26, and 27 illustrate templates for presenting information including measurement data.
Figure 22:
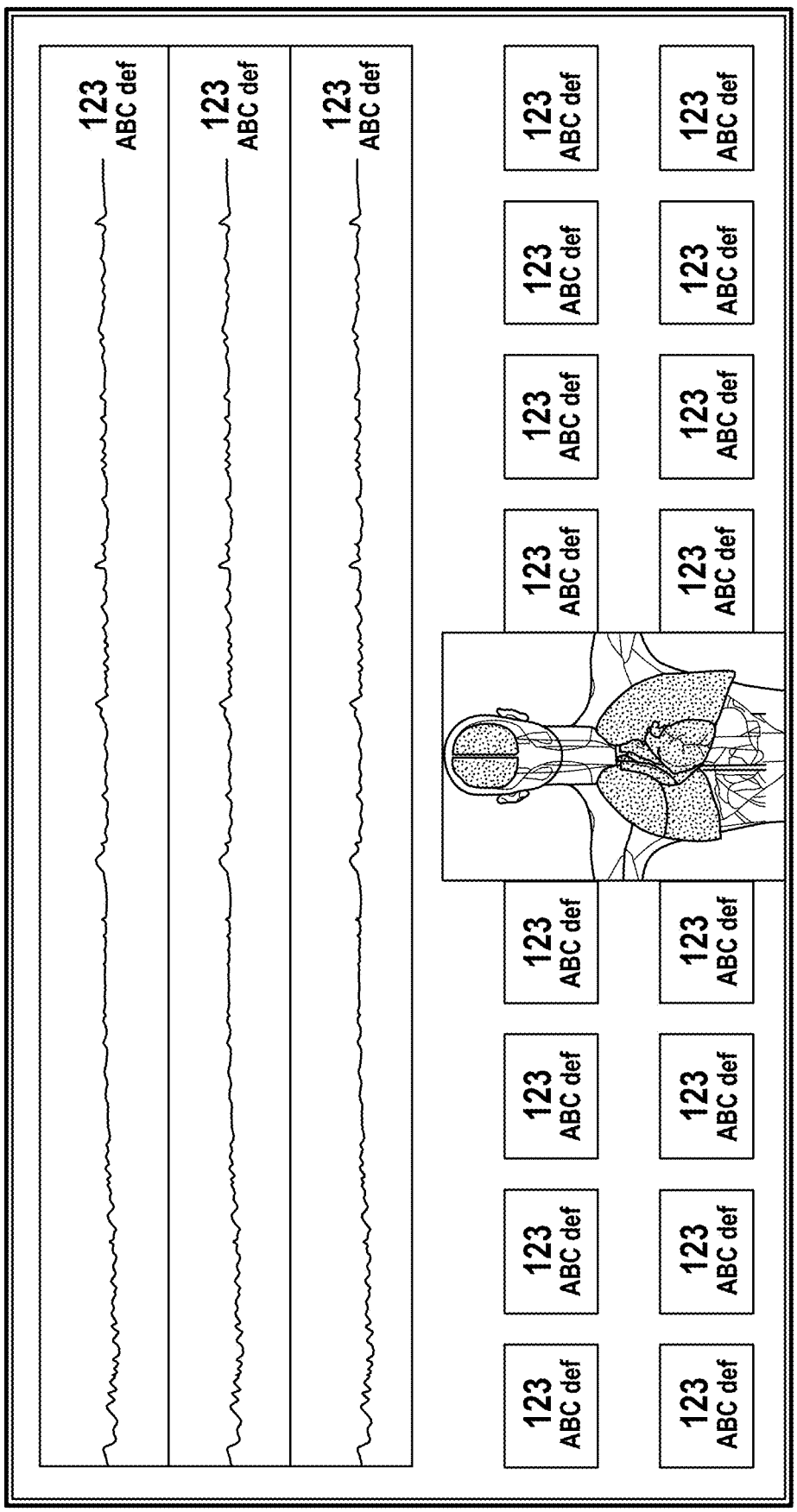
Figure 23:
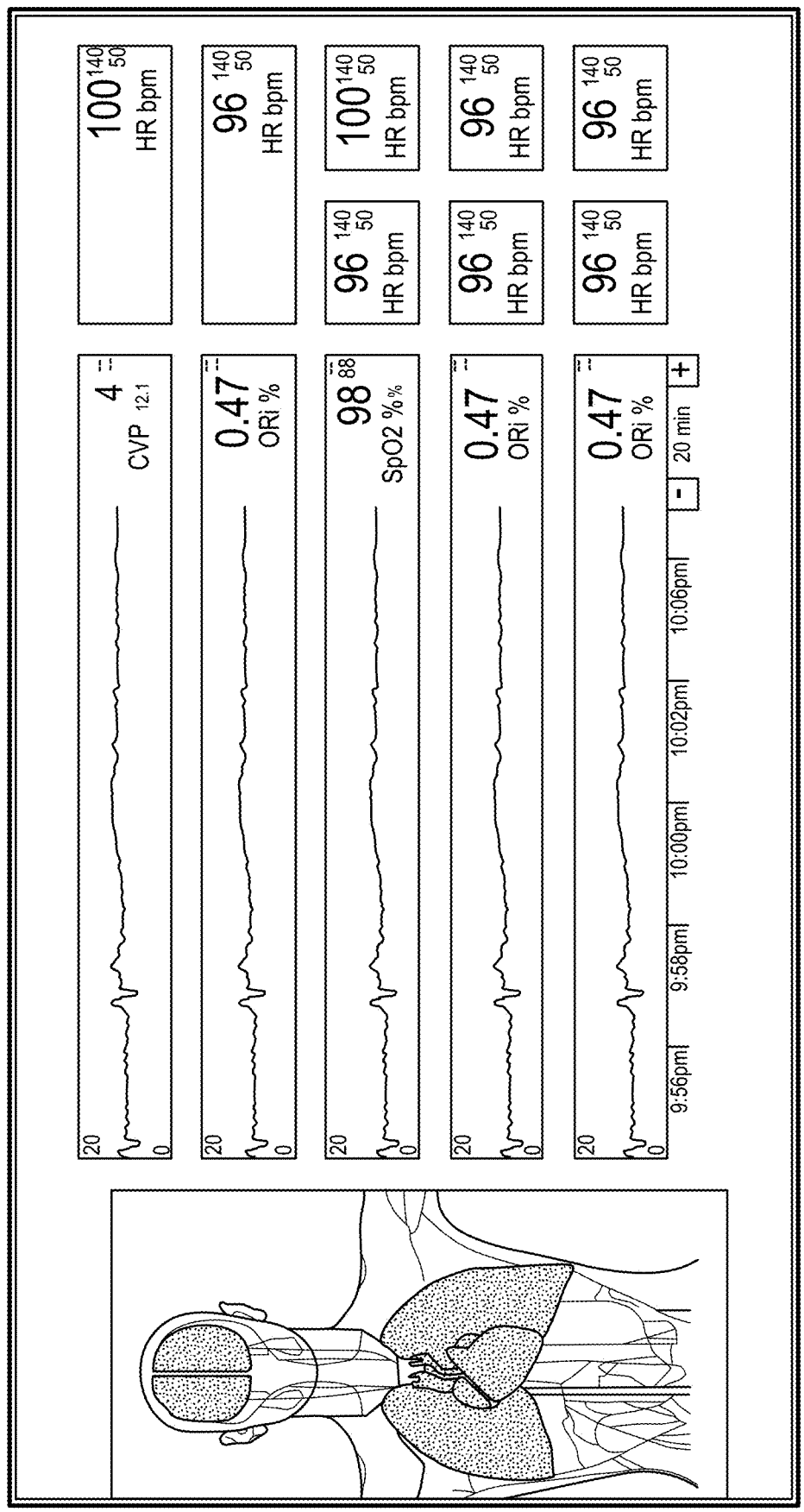
Figure 24:
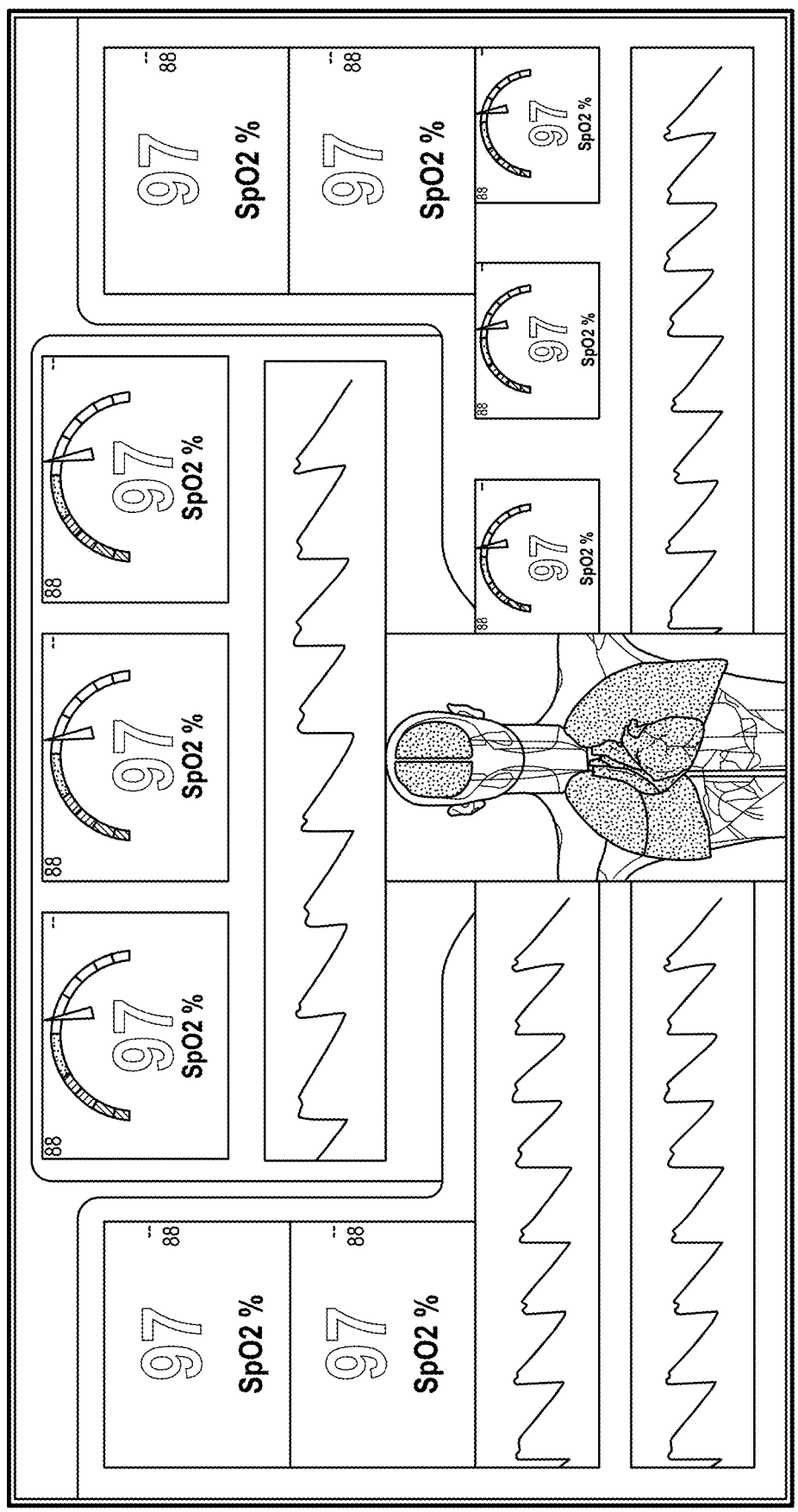
Figure 25:
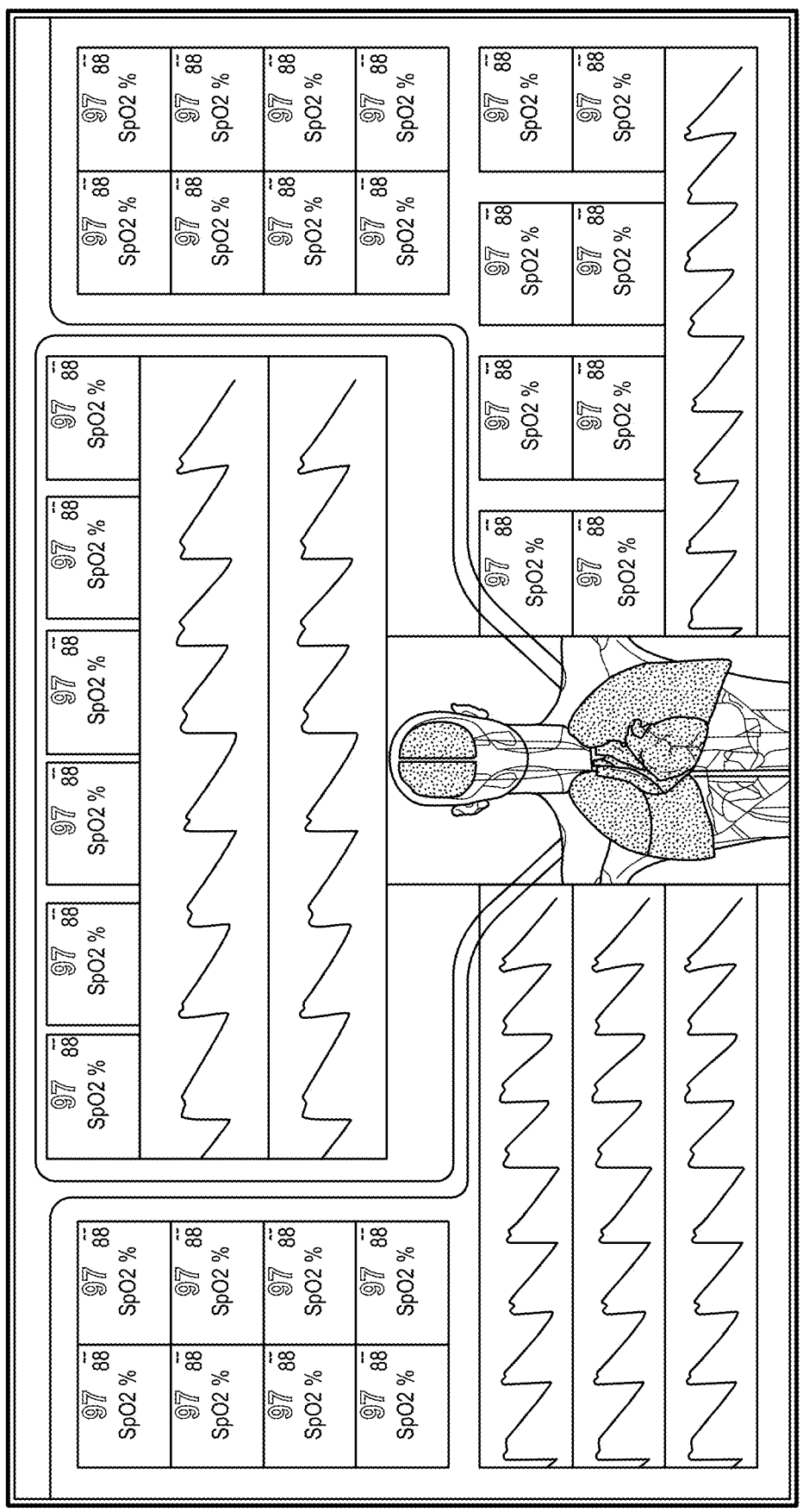
Figure 26:
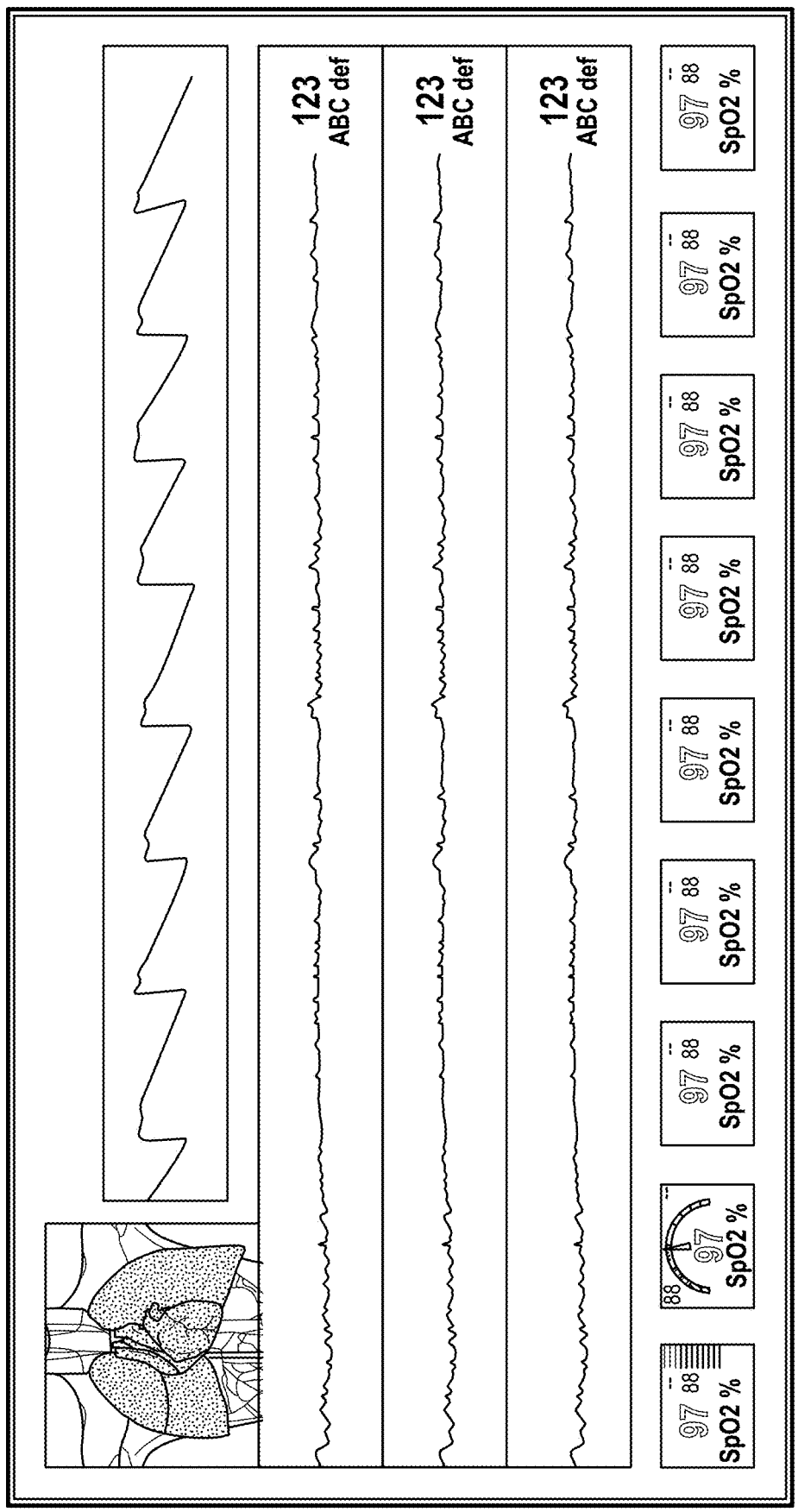
Figure 27:
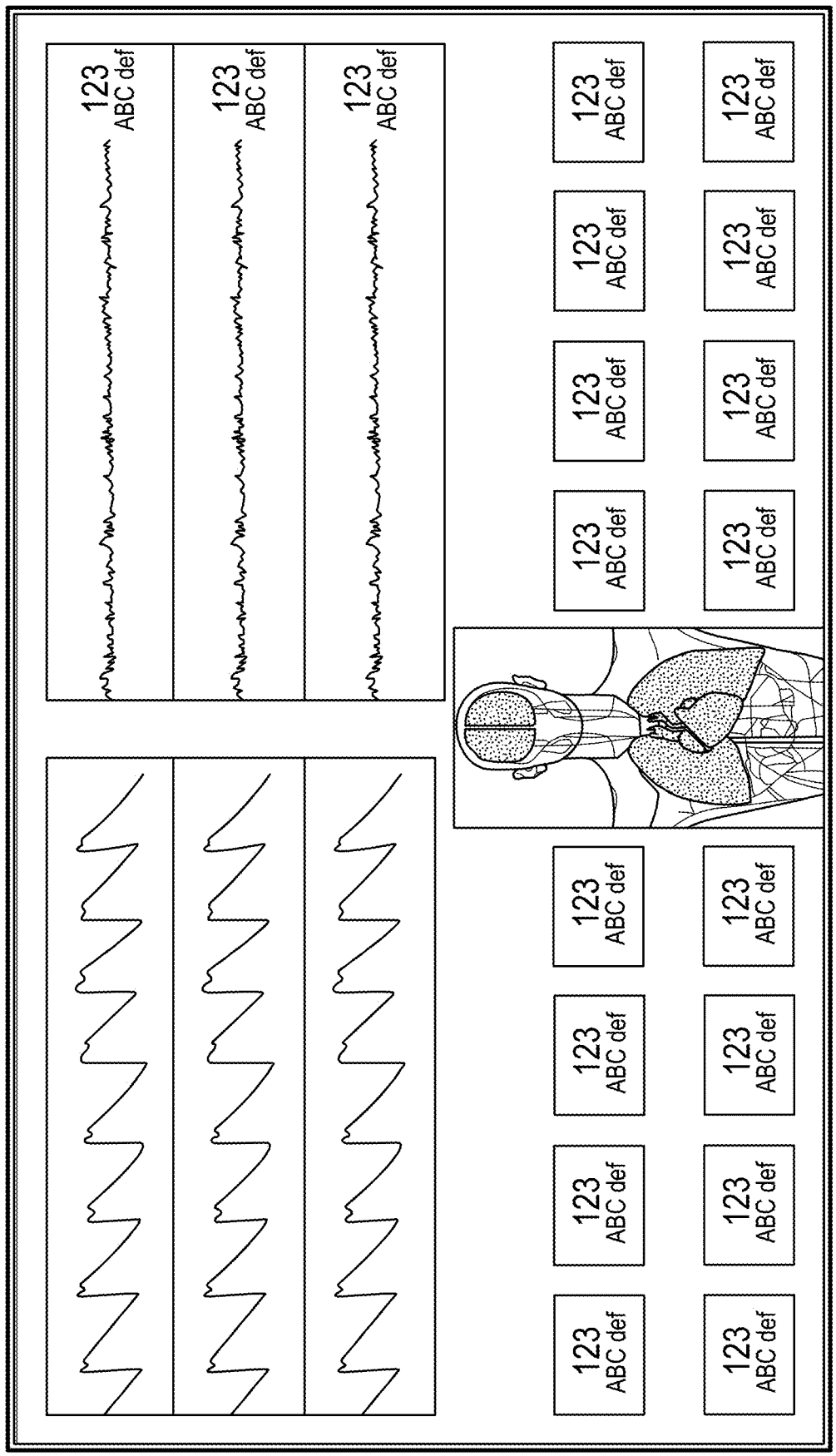
Figure 28:
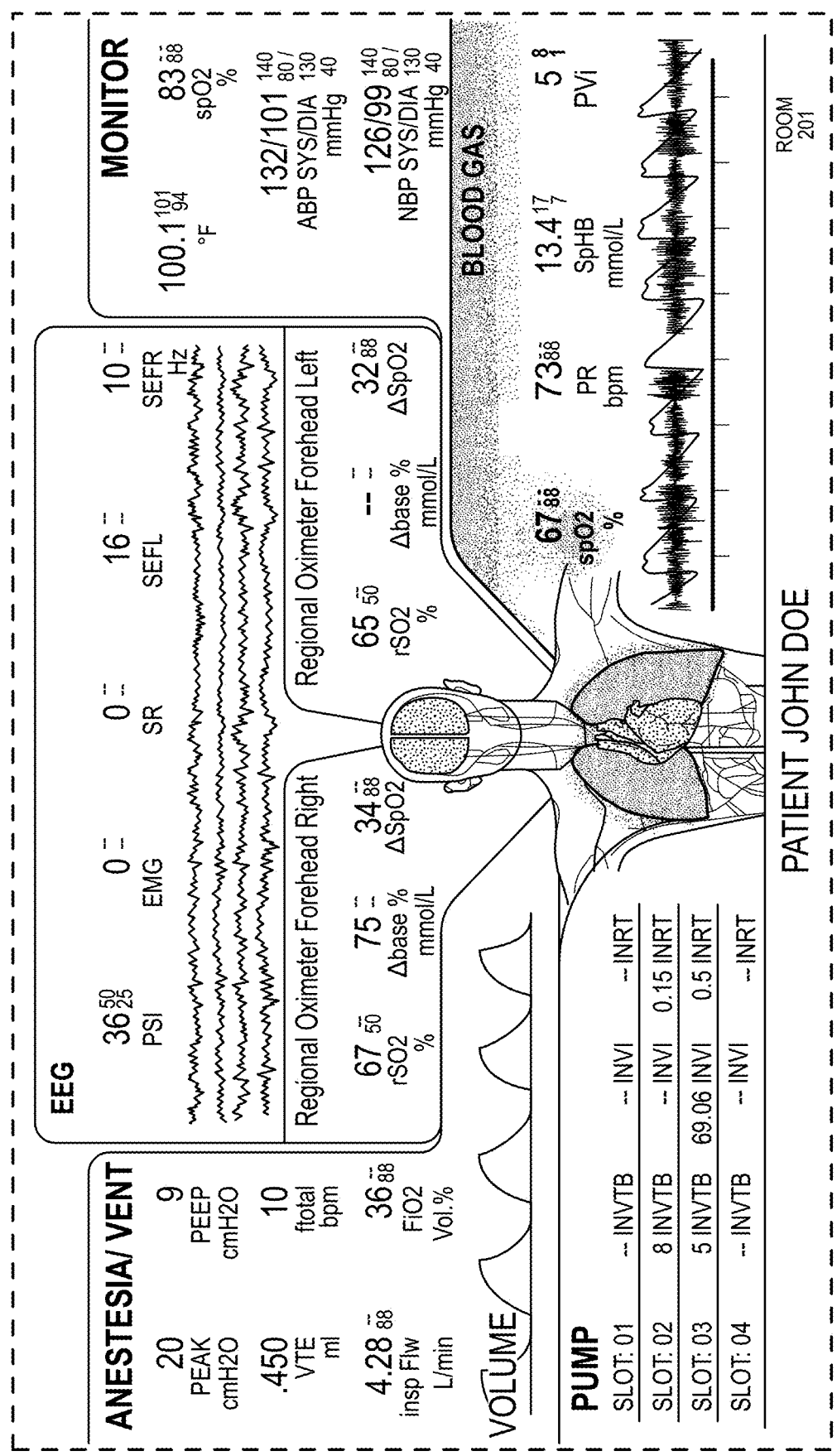
FIG. 28 is a front view of a display screen or portion thereof with graphical user interface showing an ornamental design.
Figure 29:
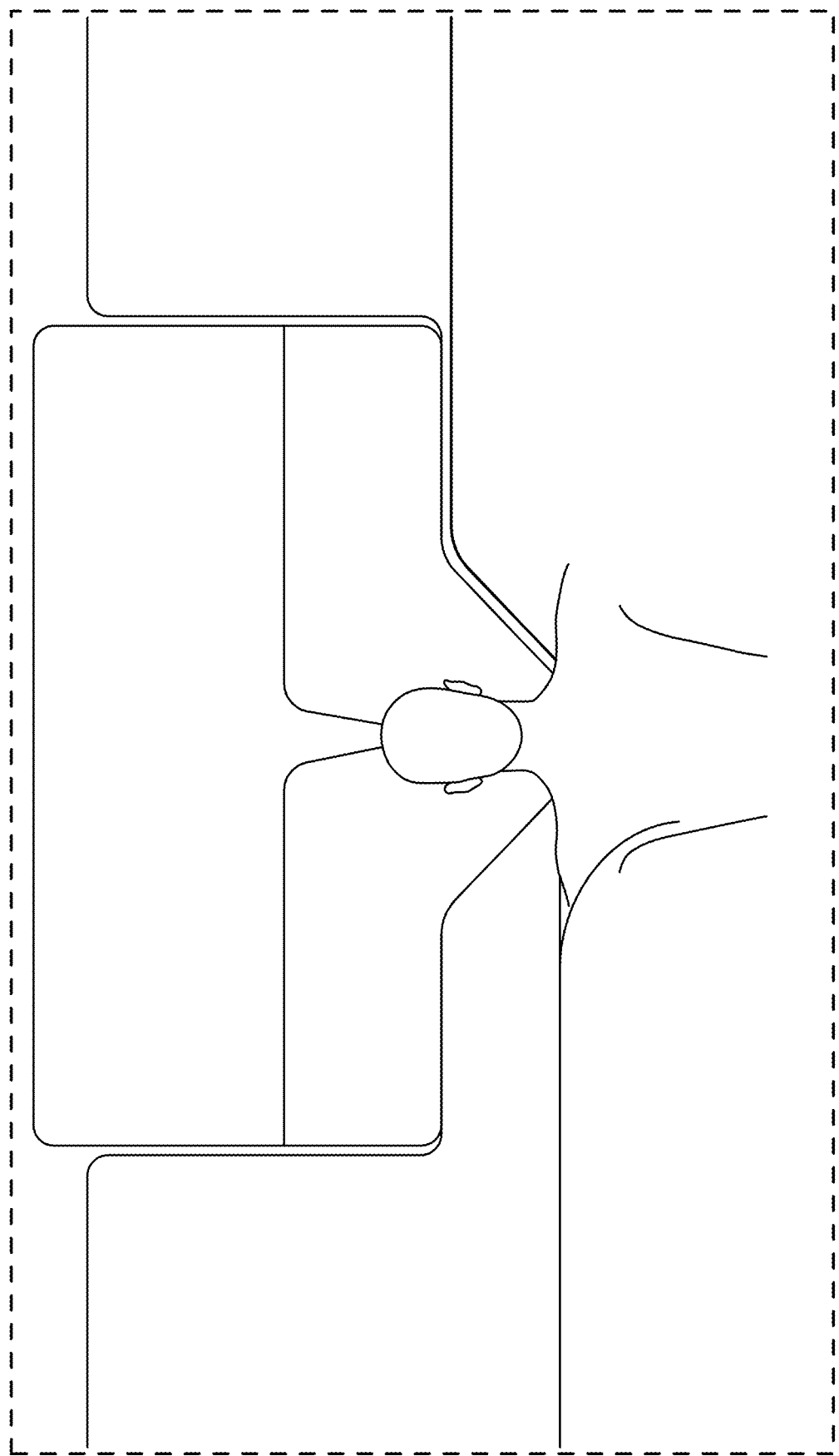
FIG. 29 is a front view of a display screen or portion thereof with graphical user interface in accordance with a second embodiment.
Figure 30:
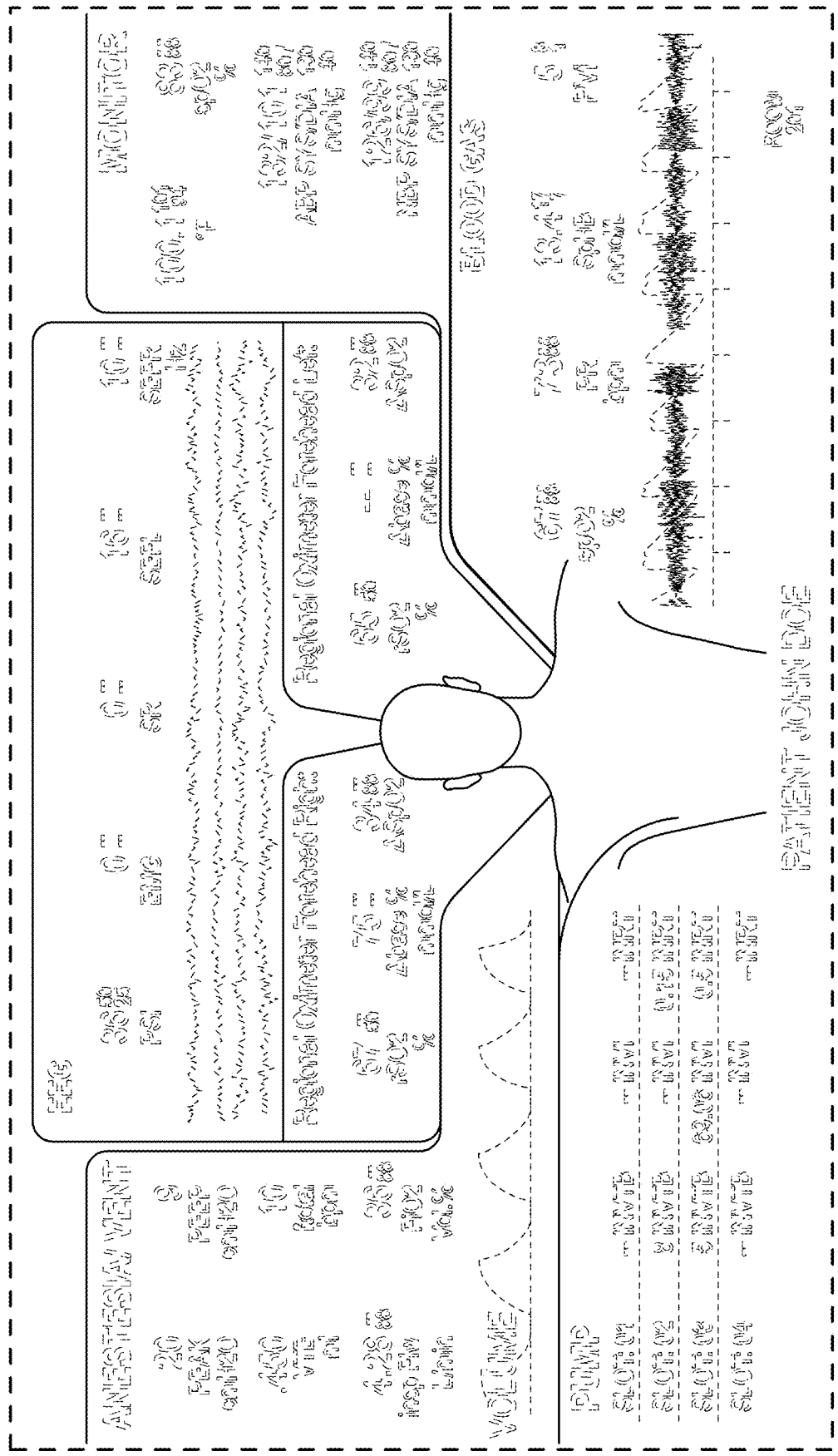
FIG. 30 is a front view of a display screen or portion thereof with graphical user interface in accordance with a third embodiment.
Figure 31:
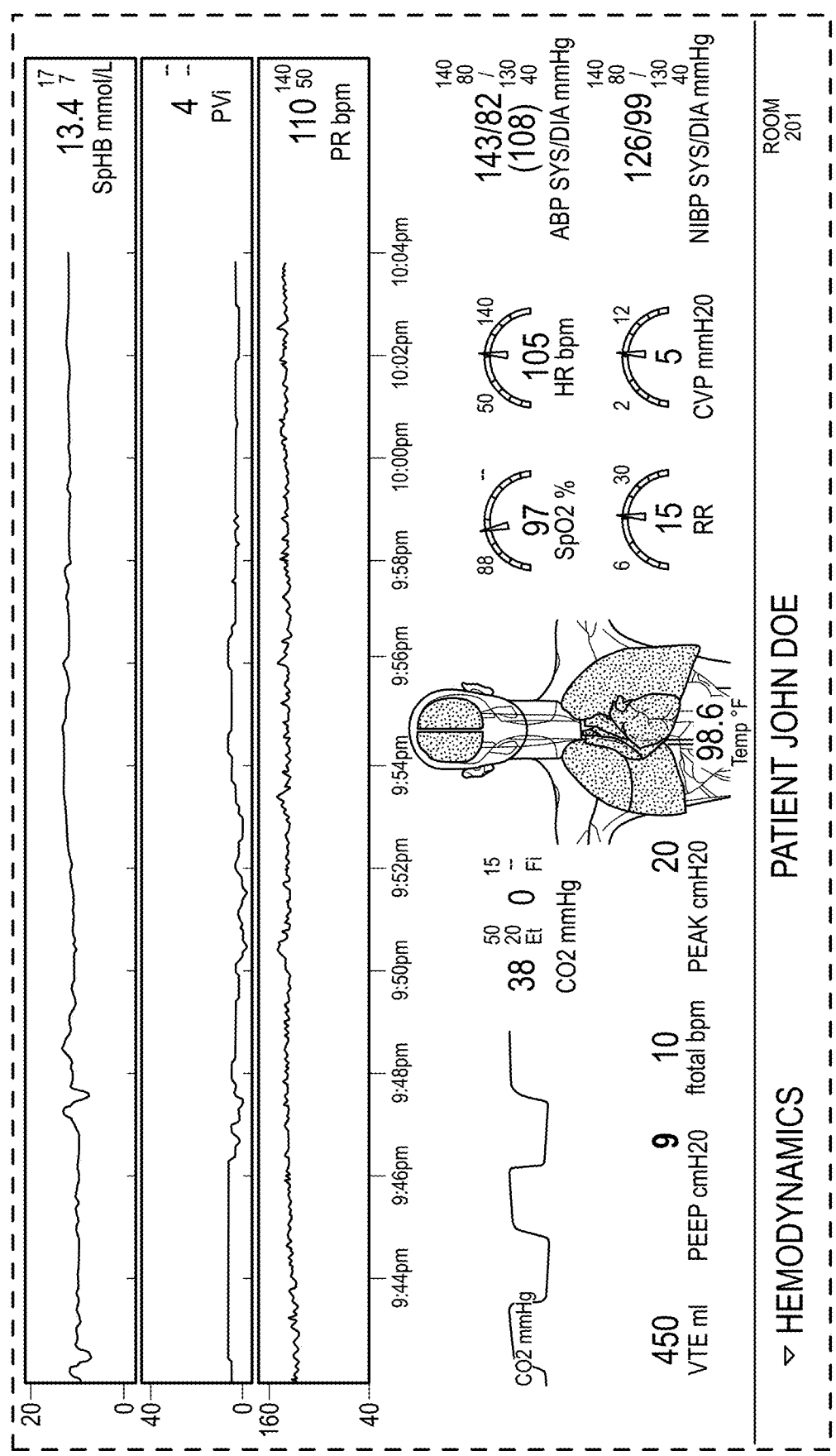
FIG. 31 is a front view of a display screen or portion thereof with a graphical user interface in accordance with a fourth embodiment.
Figure 32:
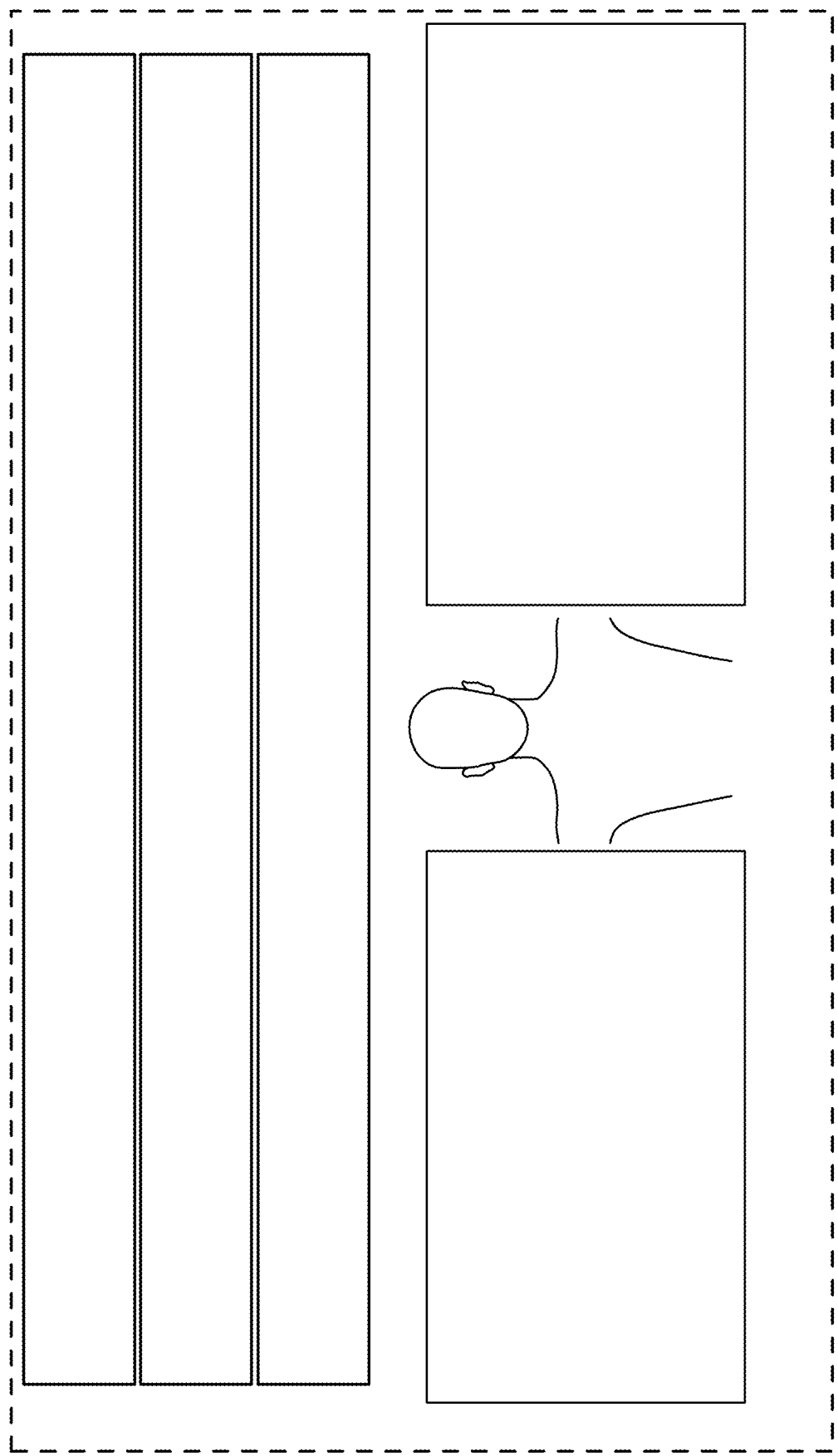
FIG. 32 is a front view of a display screen or portion thereof with a graphical user interface in accordance with a fifth embodiment.
Figure 33:
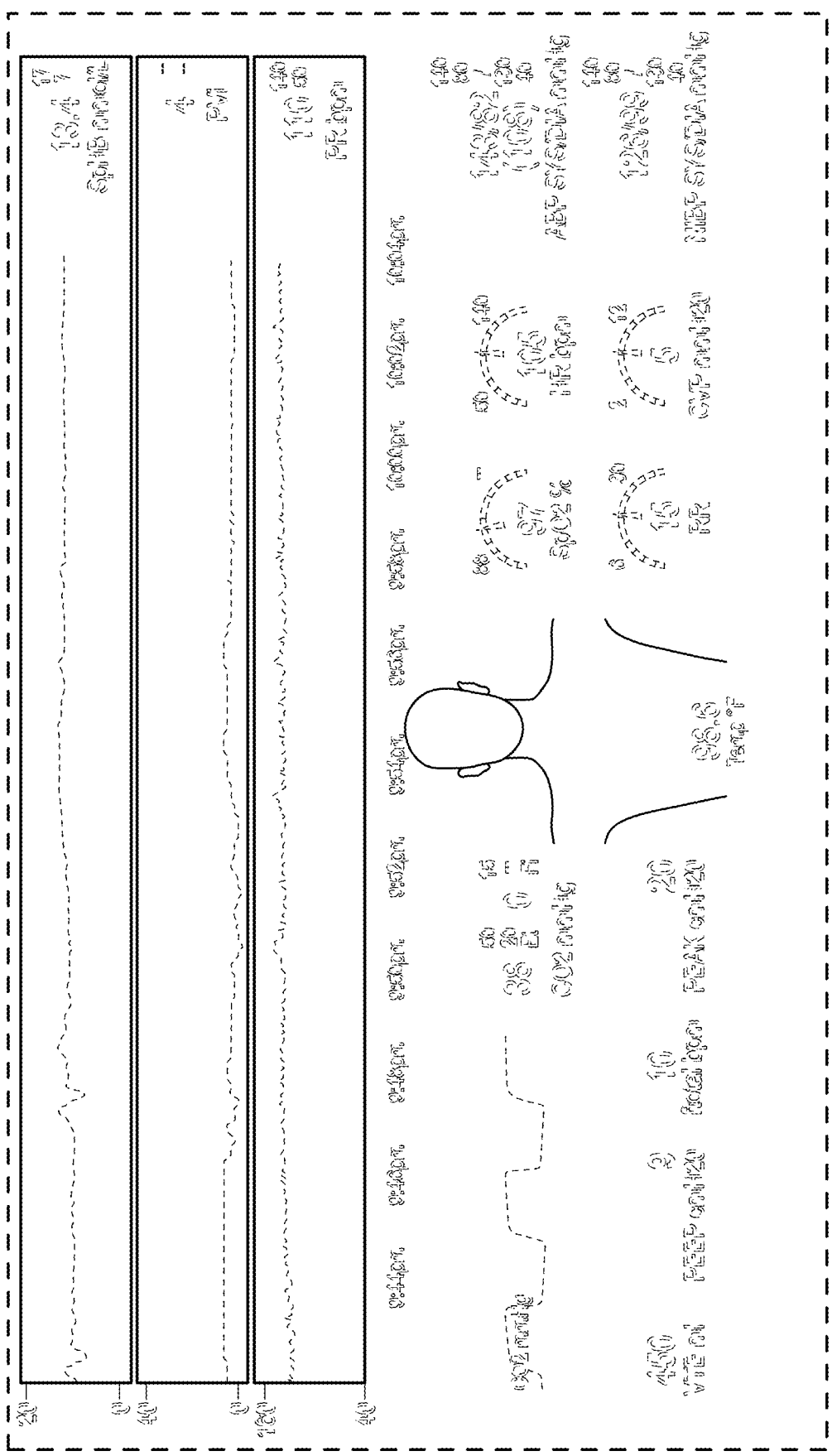
FIG. 33 is a front view of a display screen or portion thereof with a graphical user interface in accordance with a sixth embodiment.
Figure 34:
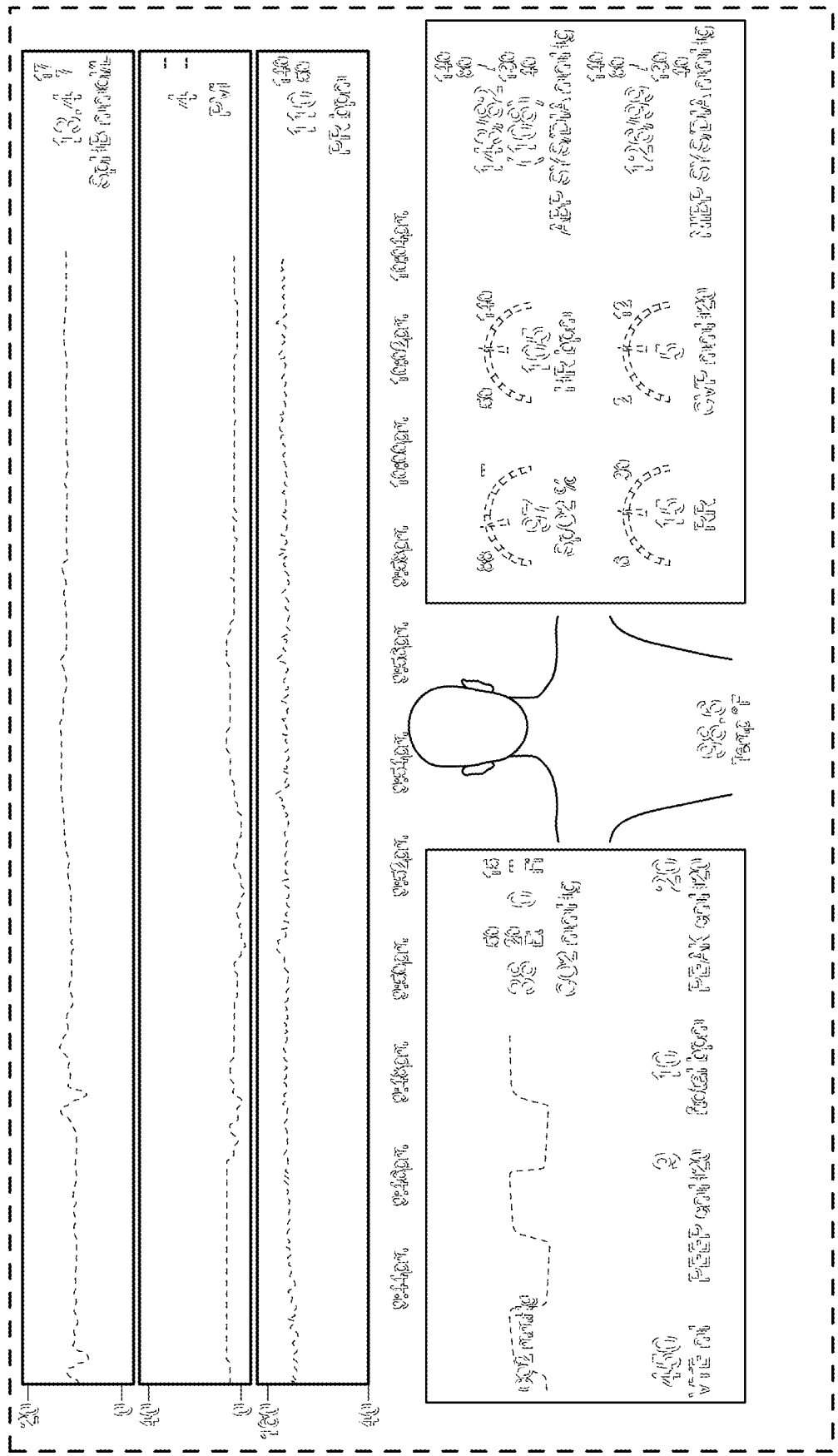
FIG. 34 is a front view of a display screen or portion thereof with a graphical user interface in accordance with a seventh embodiment.
Figure 35:
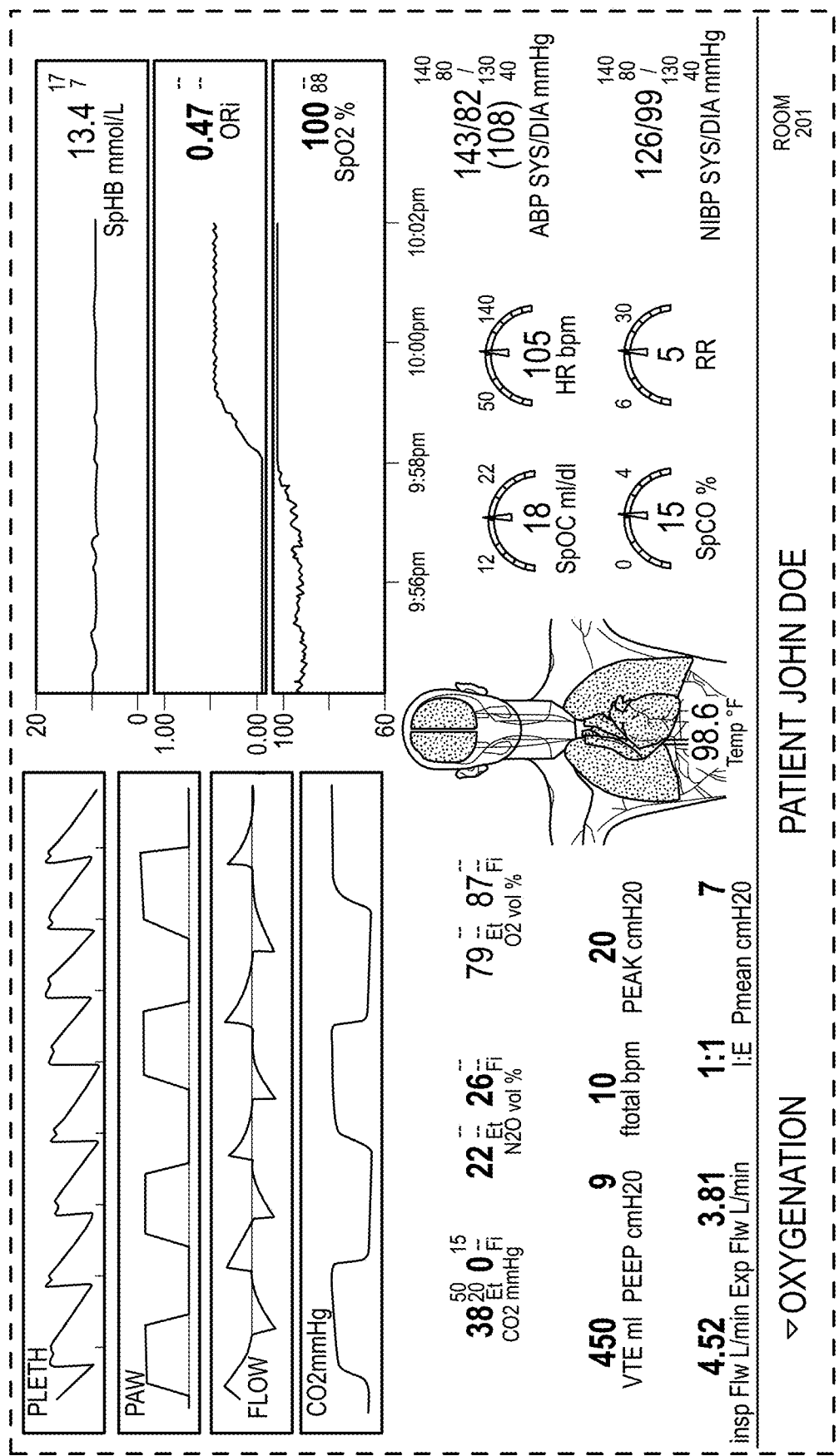
FIG. 35 is a front view of a display screen or portion thereof with a graphical user interface in accordance with an eighth embodiment.
Figure 36:
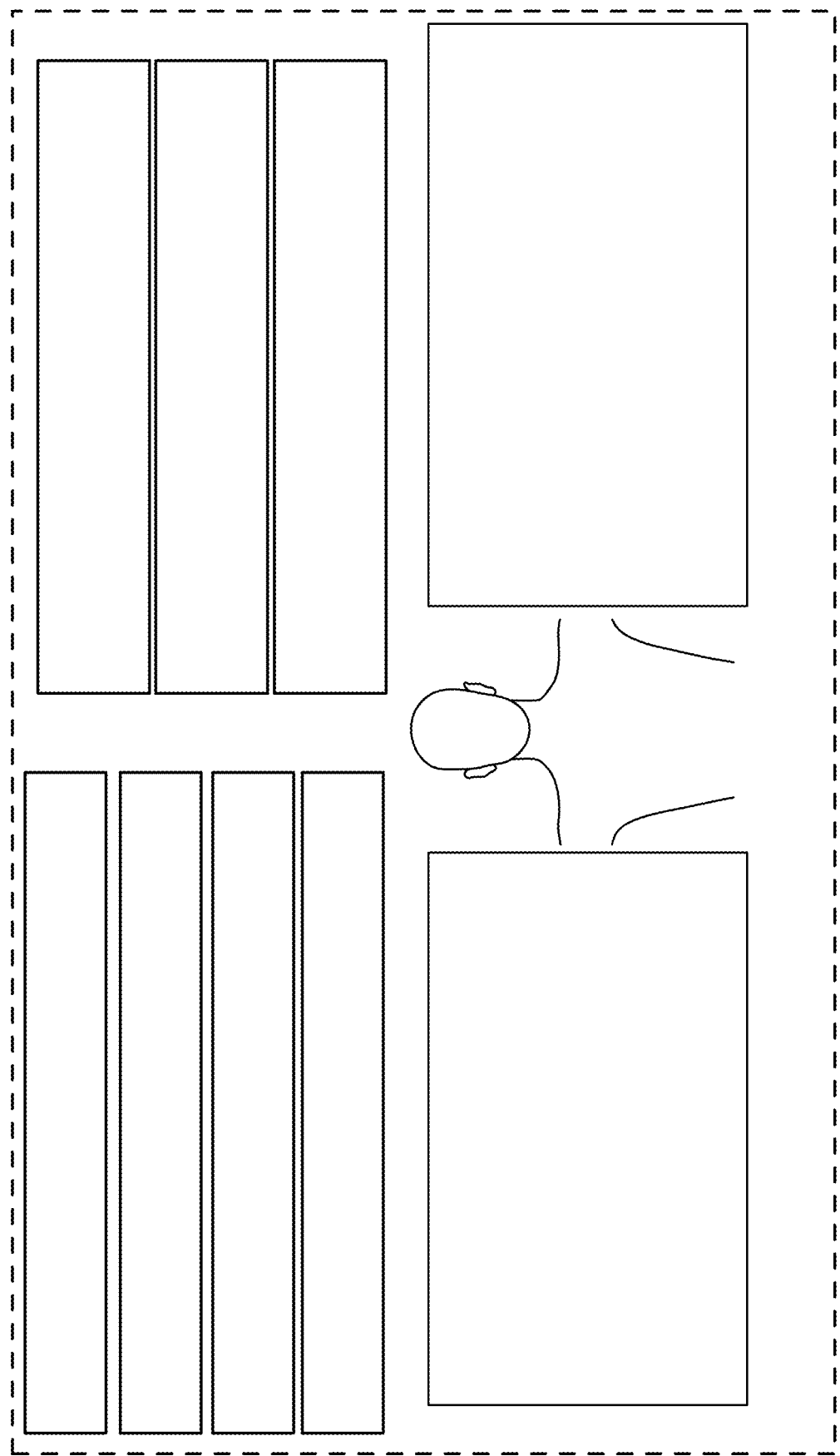
FIG. 36 is a front view of a display screen or portion thereof with a graphical user interface in accordance with a ninth embodiment.
Figure 37:
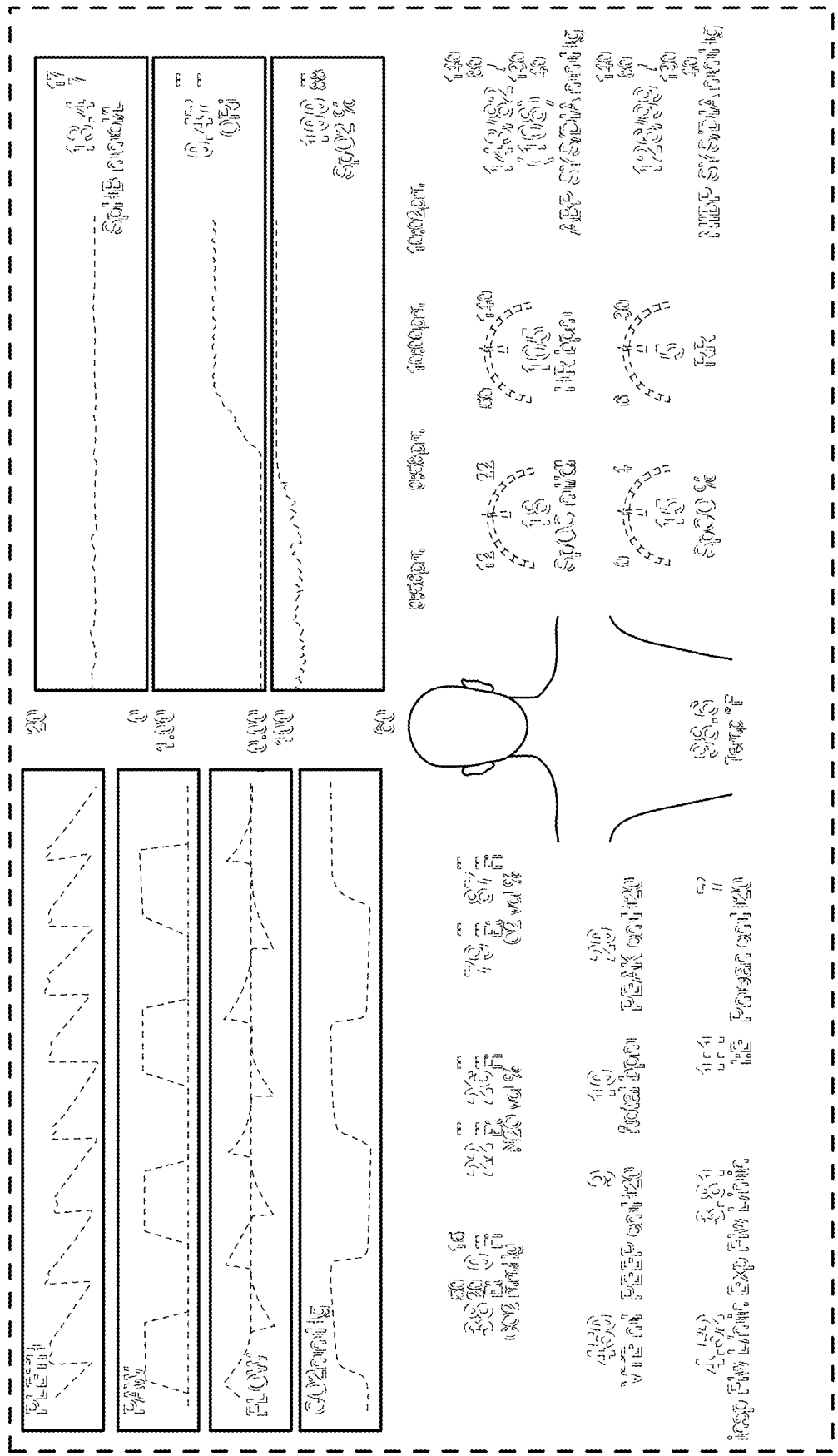
FIG. 37 is a front view of a display screen or portion thereof with a graphical user interface in accordance with a tenth embodiment.
Figure 38:
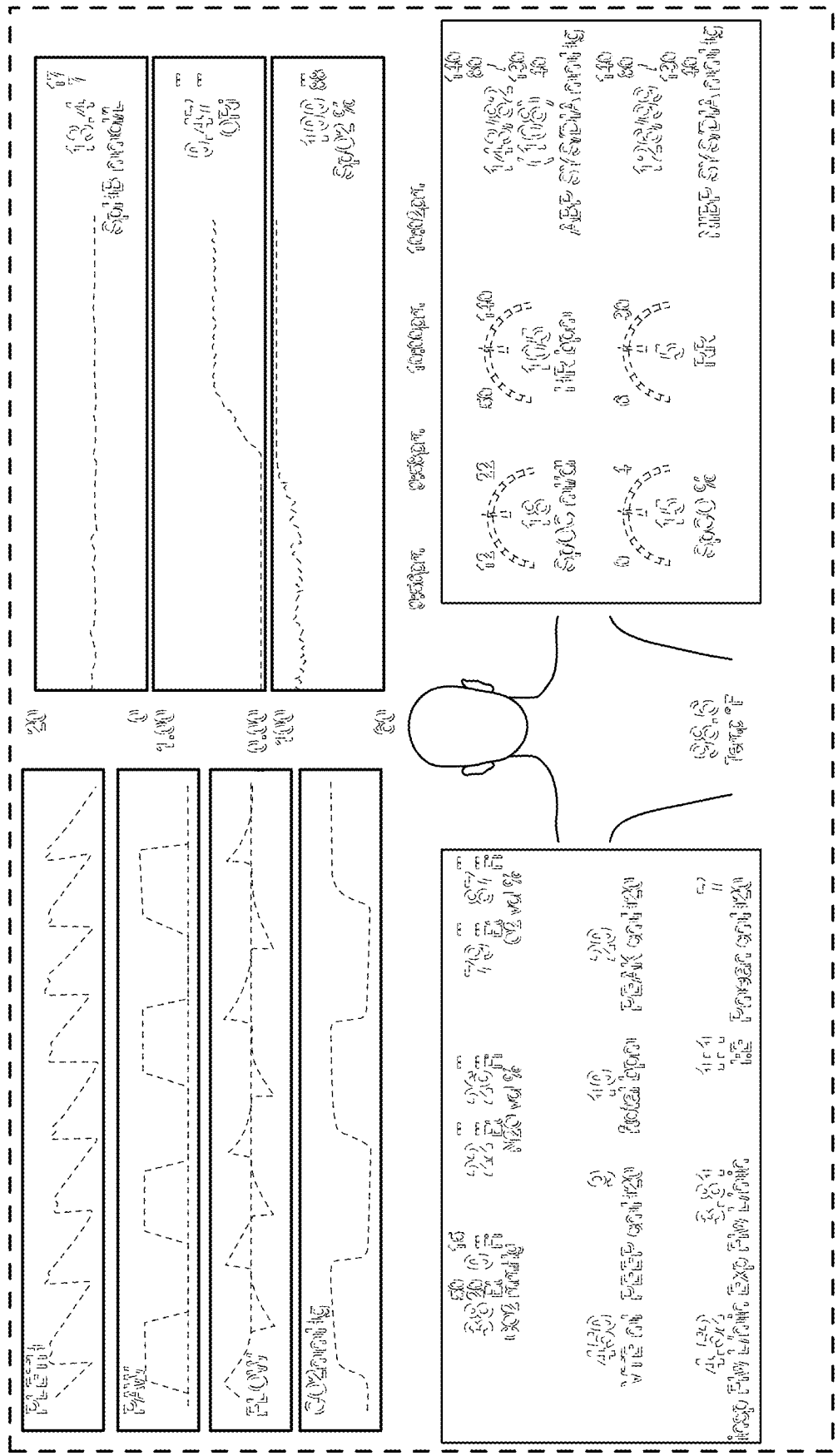
FIG. 38 is a front view of a display screen or portion thereof with a graphical user interface in accordance with an eleventh embodiment.
Figure 39:
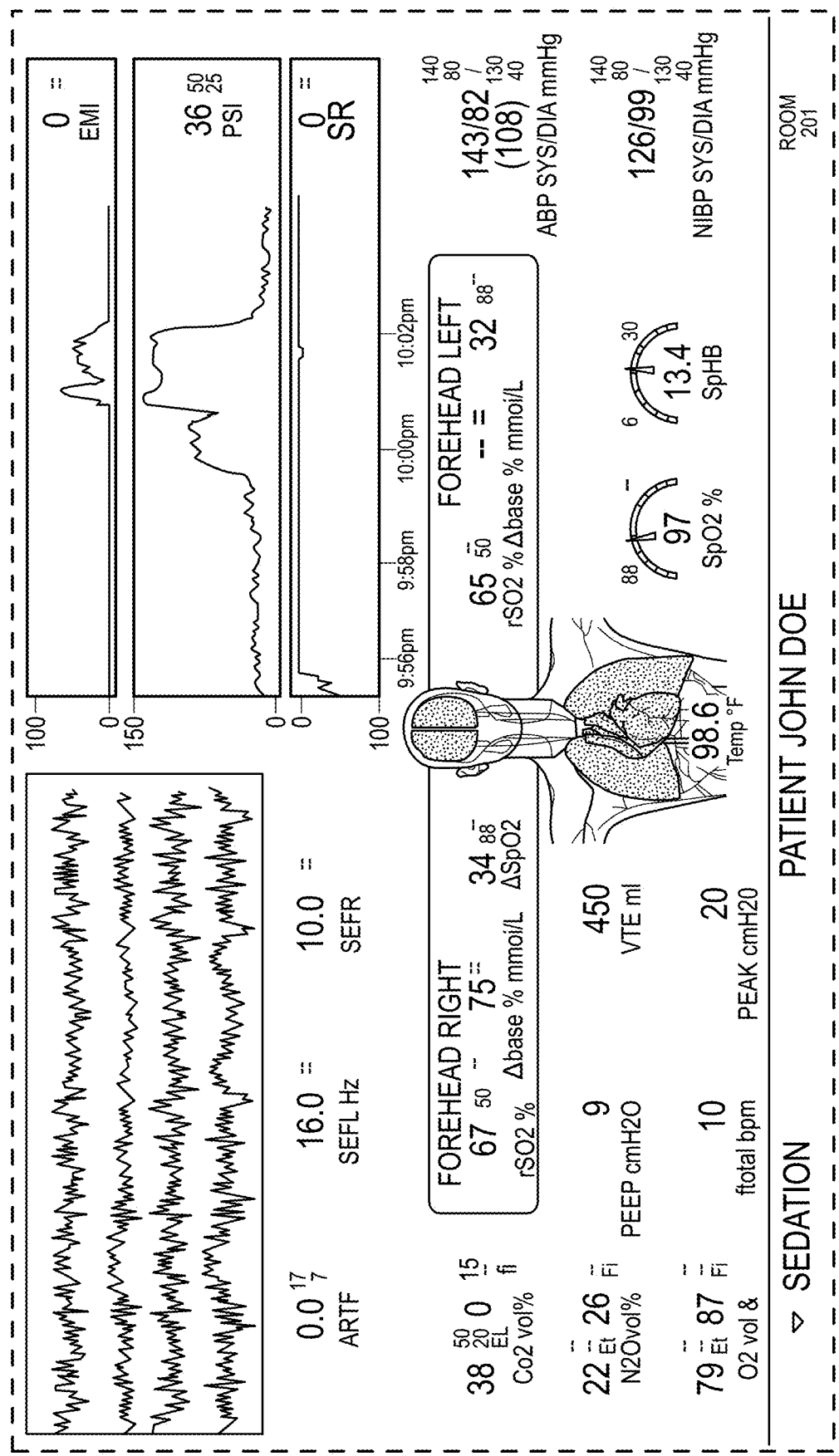
FIG. 39 is a front view of a display screen or portion thereof with a graphical user interface in accordance with a twelfth embodiment.
Figure 40:
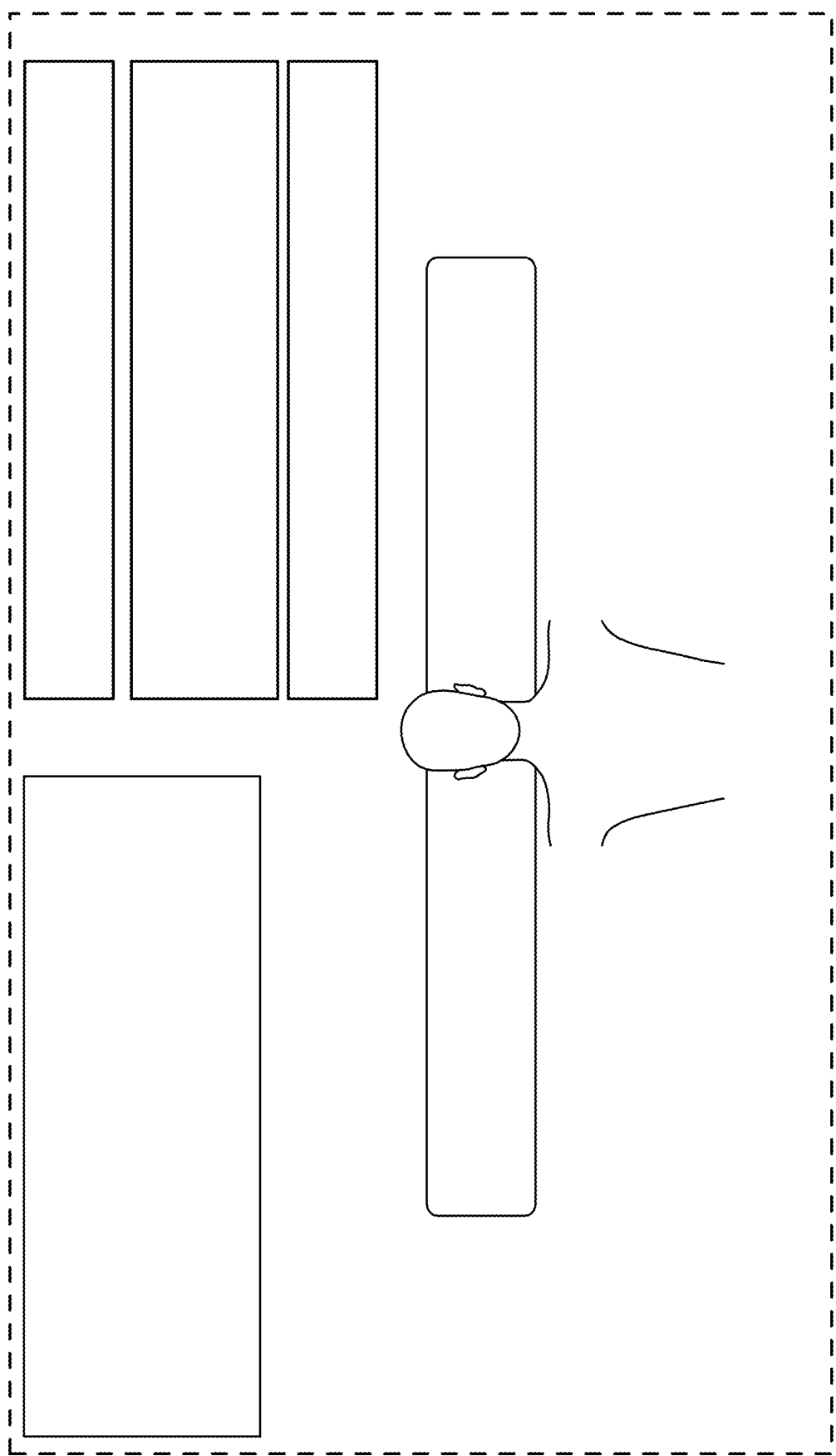
FIG. 40 is a front view of a display screen or portion thereof with a graphical user interface in accordance with a thirteenth embodiment.
Figure 41:
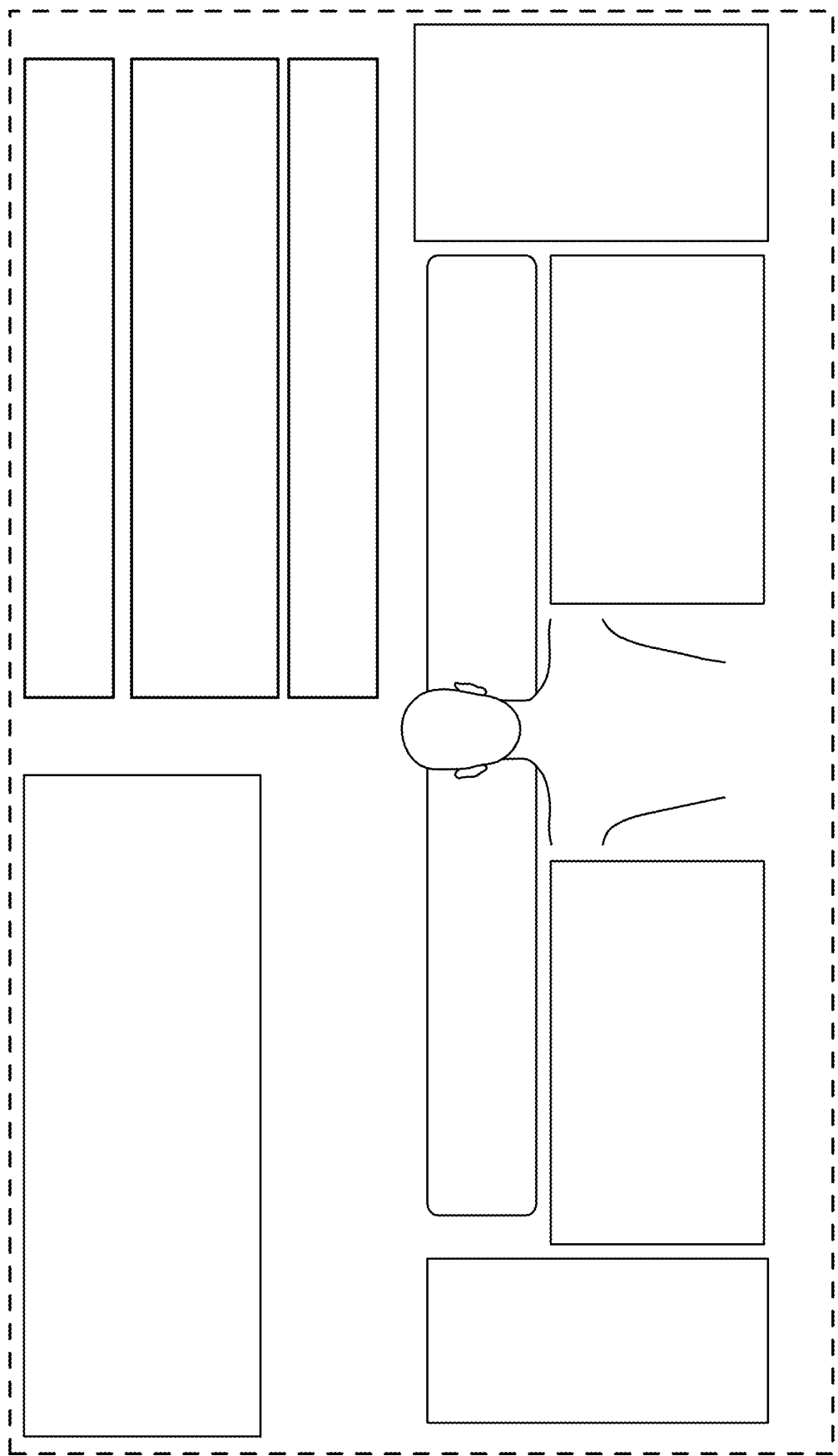
FIG. 41 is a front view of a display screen or portion thereof with a graphical user interface in accordance with a fourteenth embodiment.
Figure 42:
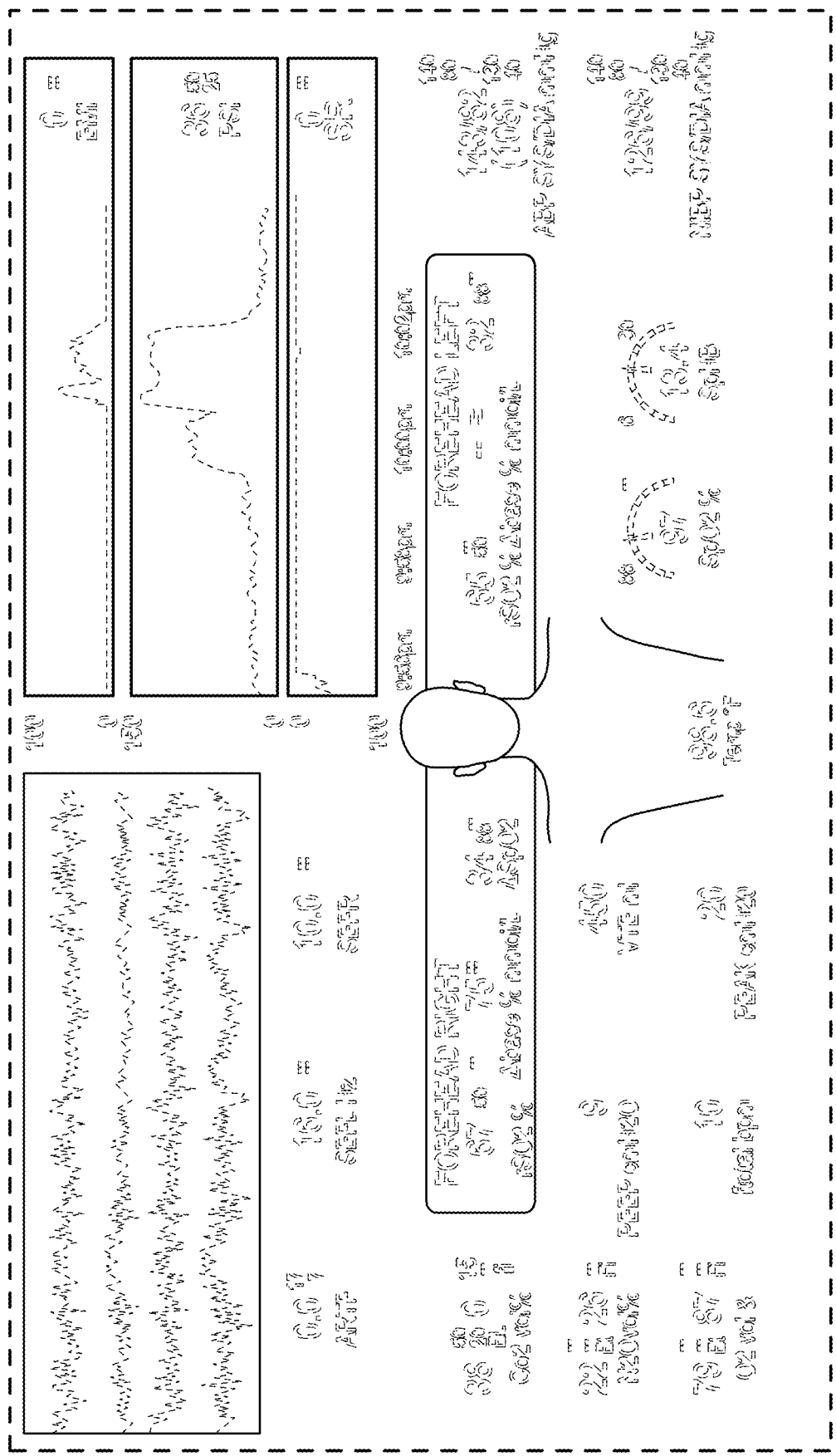
FIG. 42 is a front view of a display screen or portion thereof with a graphical user interface in accordance with a fifteenth embodiment.
Figure 43:
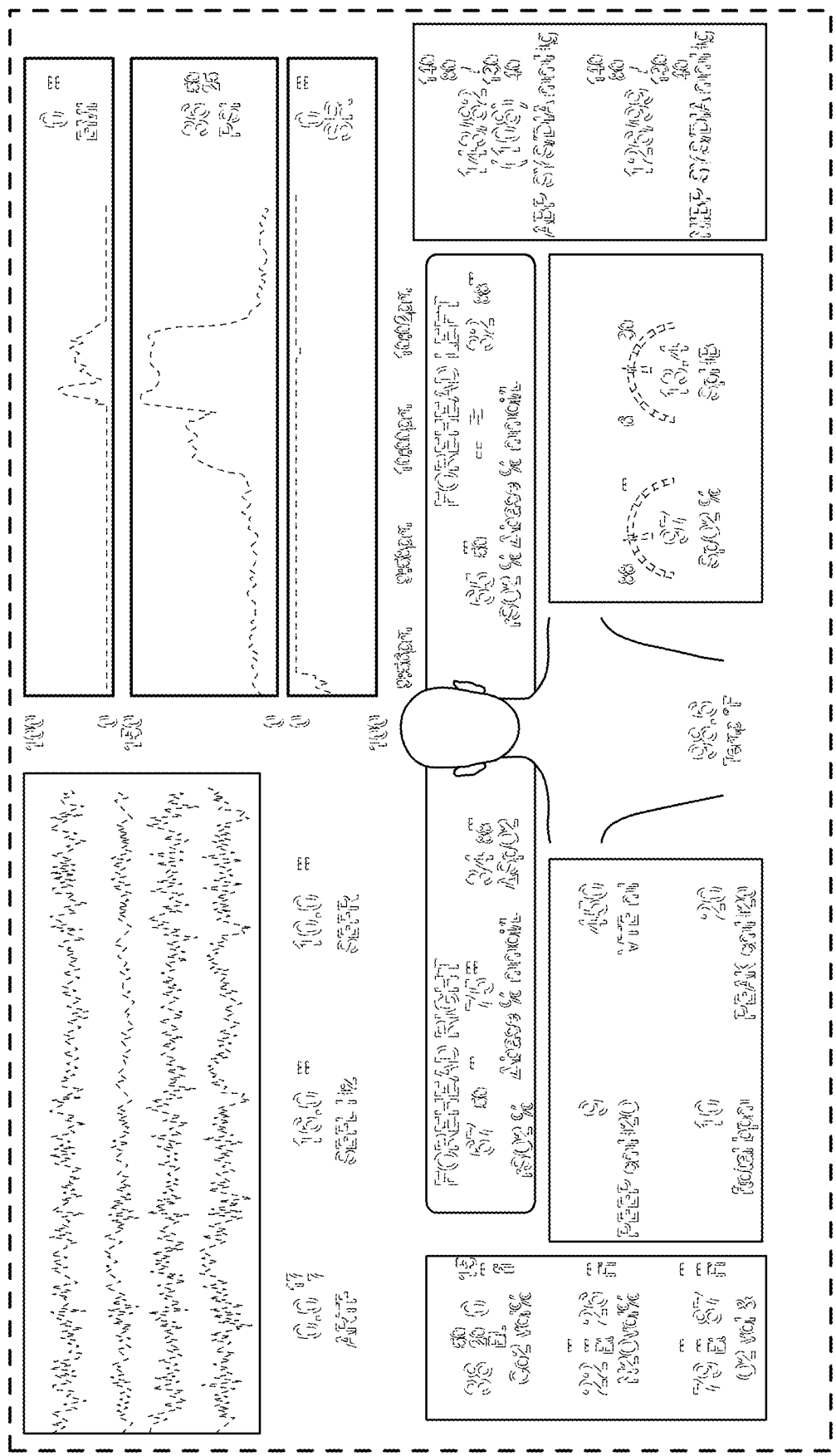
FIG. 43 is a front view of a display screen or portion thereof with a graphical user interface in accordance with a sixteenth embodiment.
Figure 44:
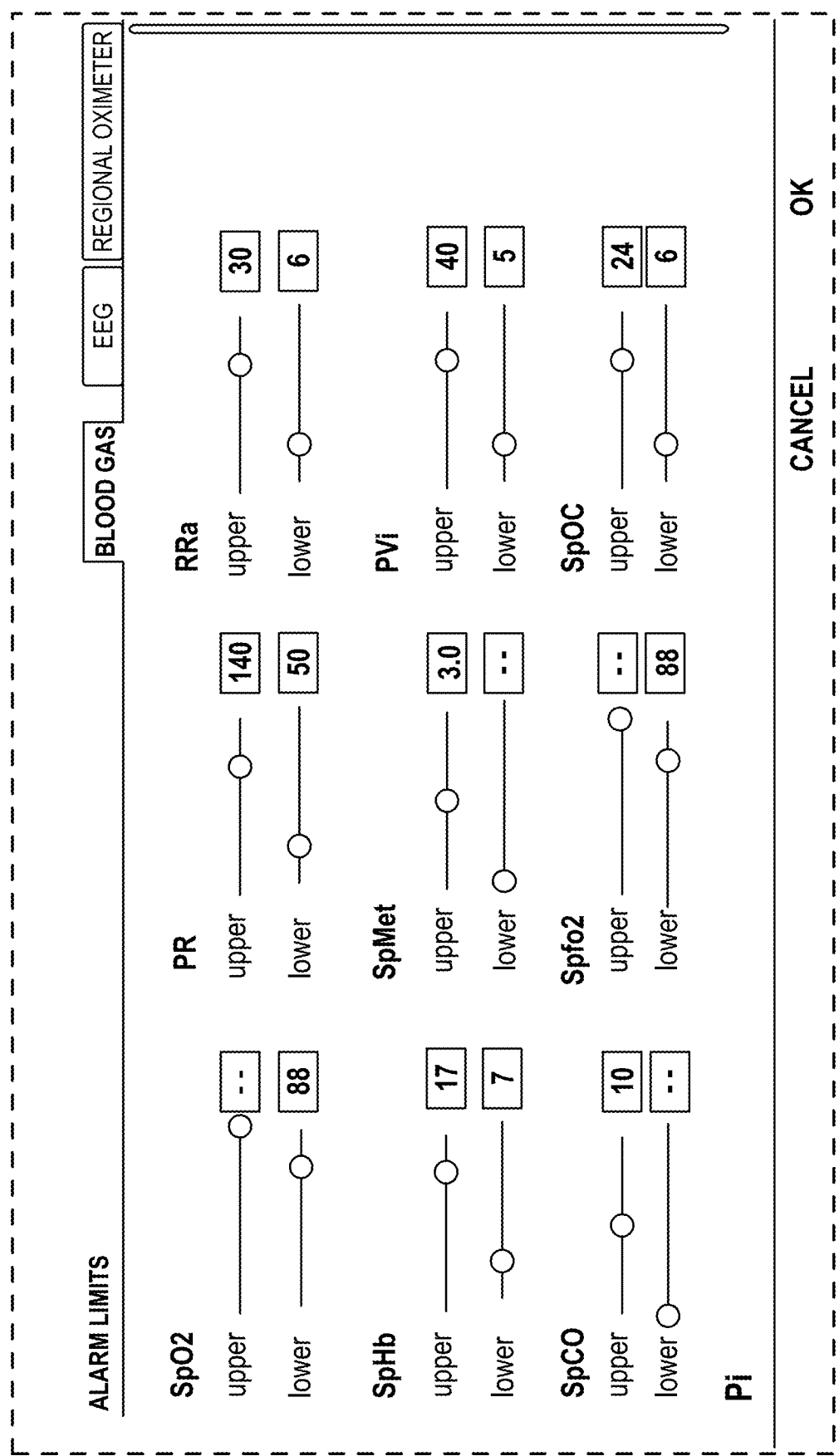
FIG. 44 is a front view of a display screen or portion thereof with a graphical user interface in accordance with a seventeenth embodiment.
Figure 45:
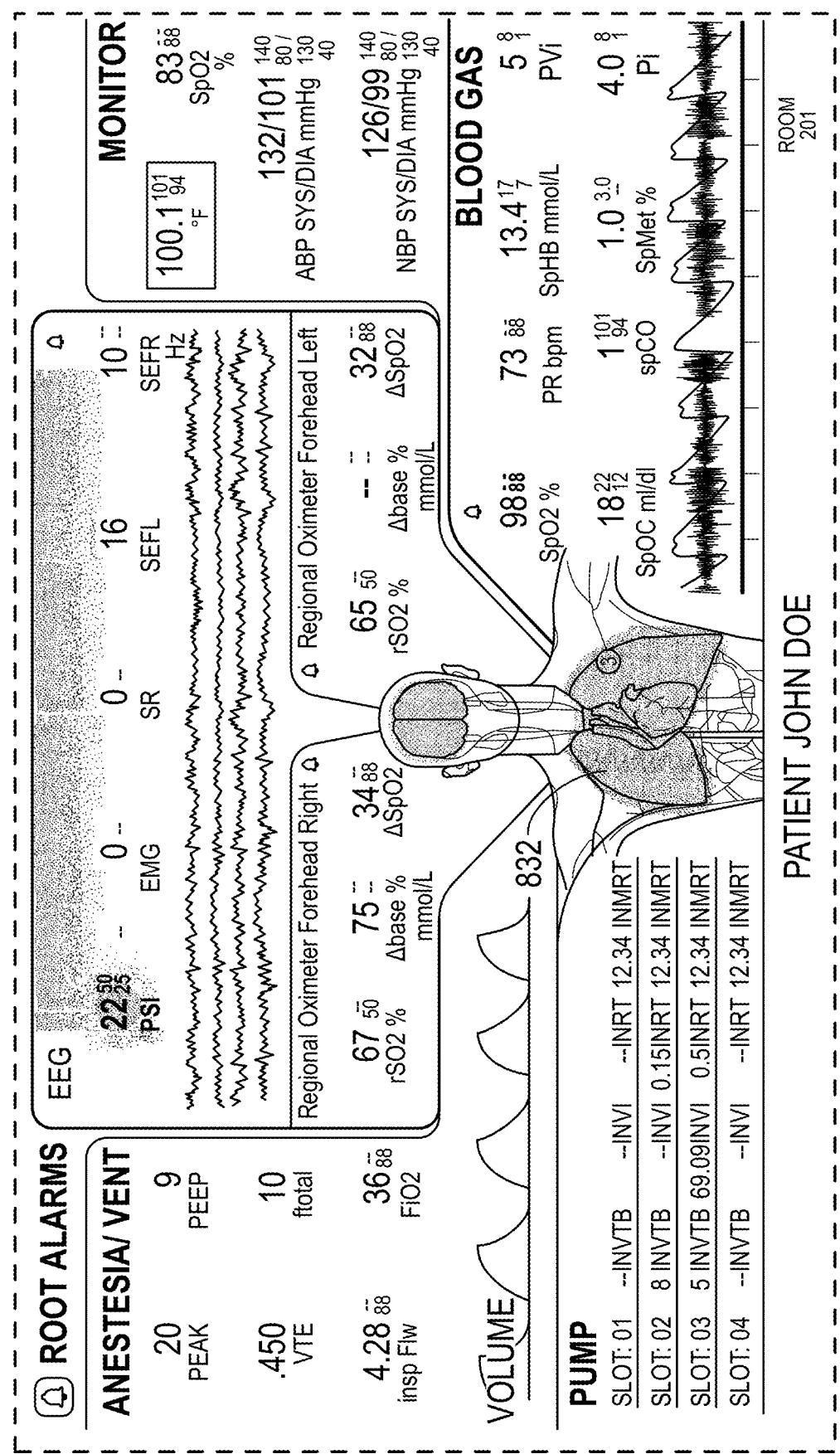
FIG. 45 is a front view of a display screen or portion thereof with a graphical user interface in accordance with an eighteenth embodiment.
Figure 46:
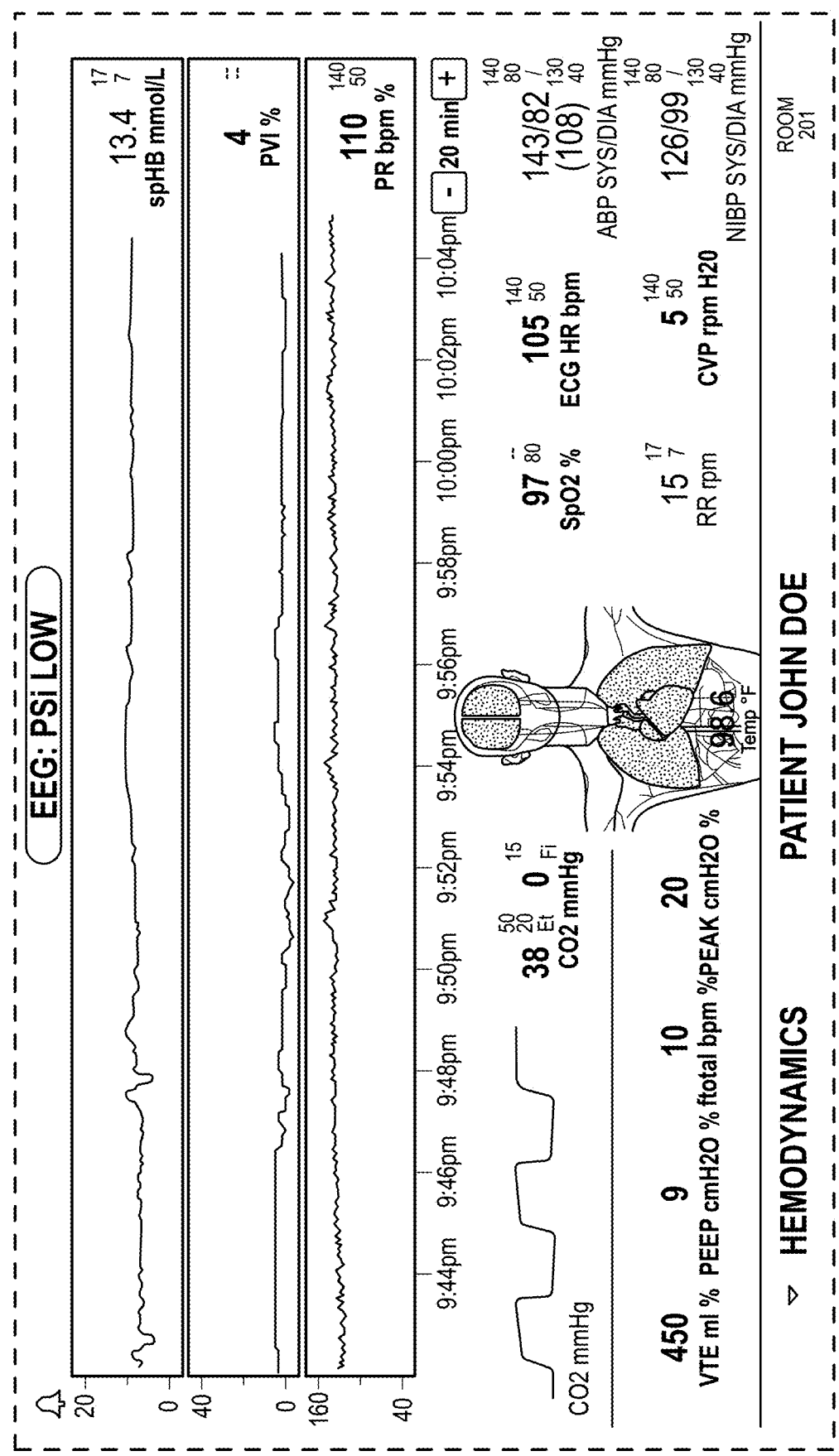
FIG. 46 is a front view of a display screen or portion thereof with a graphical user interface in accordance with a nineteenth embodiment.
Figure 47:
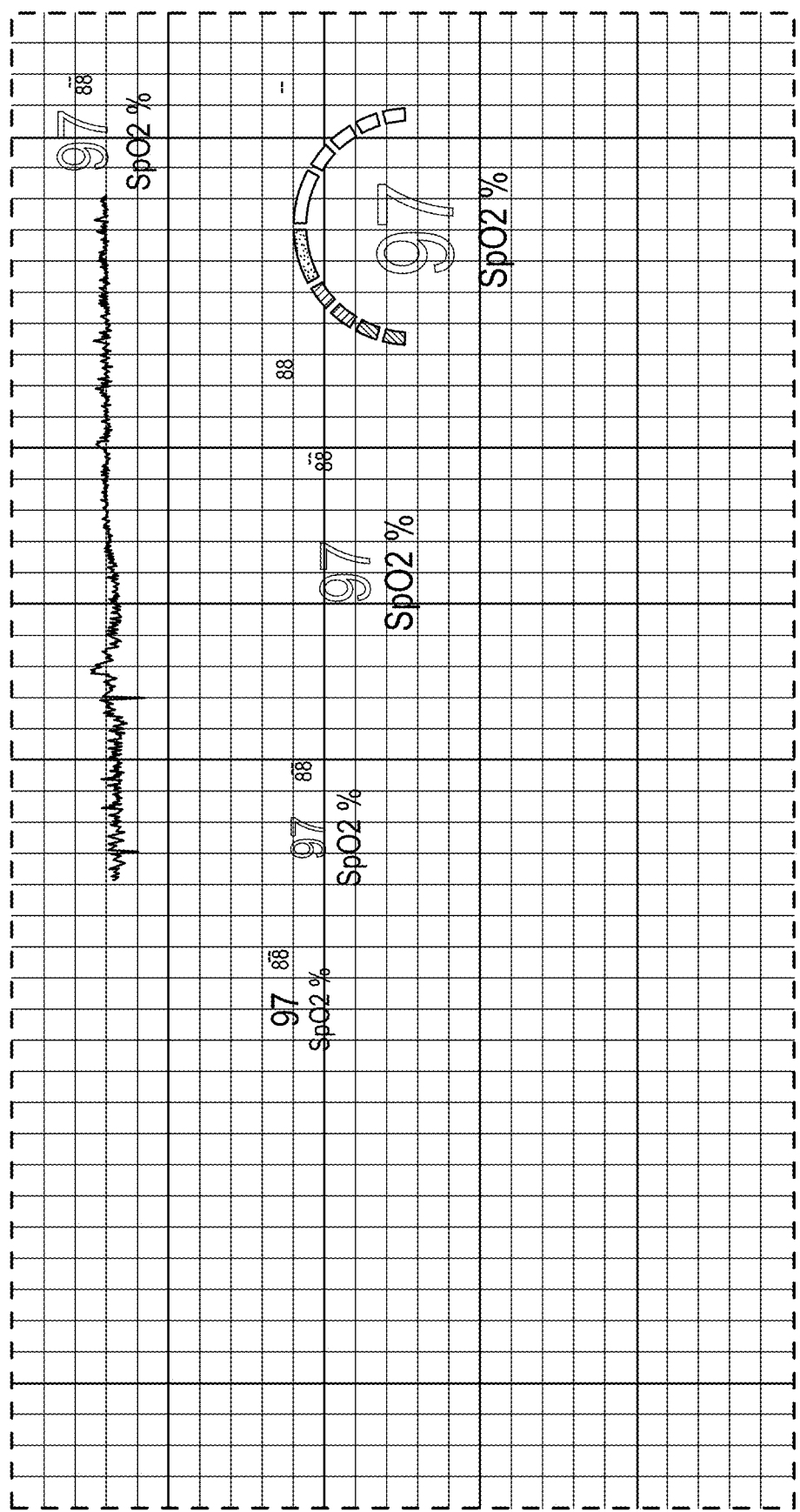
FIG. 47 is a front view of a display screen or portion thereof with a graphical user interface in accordance with a twentieth embodiment.
Figure 48:
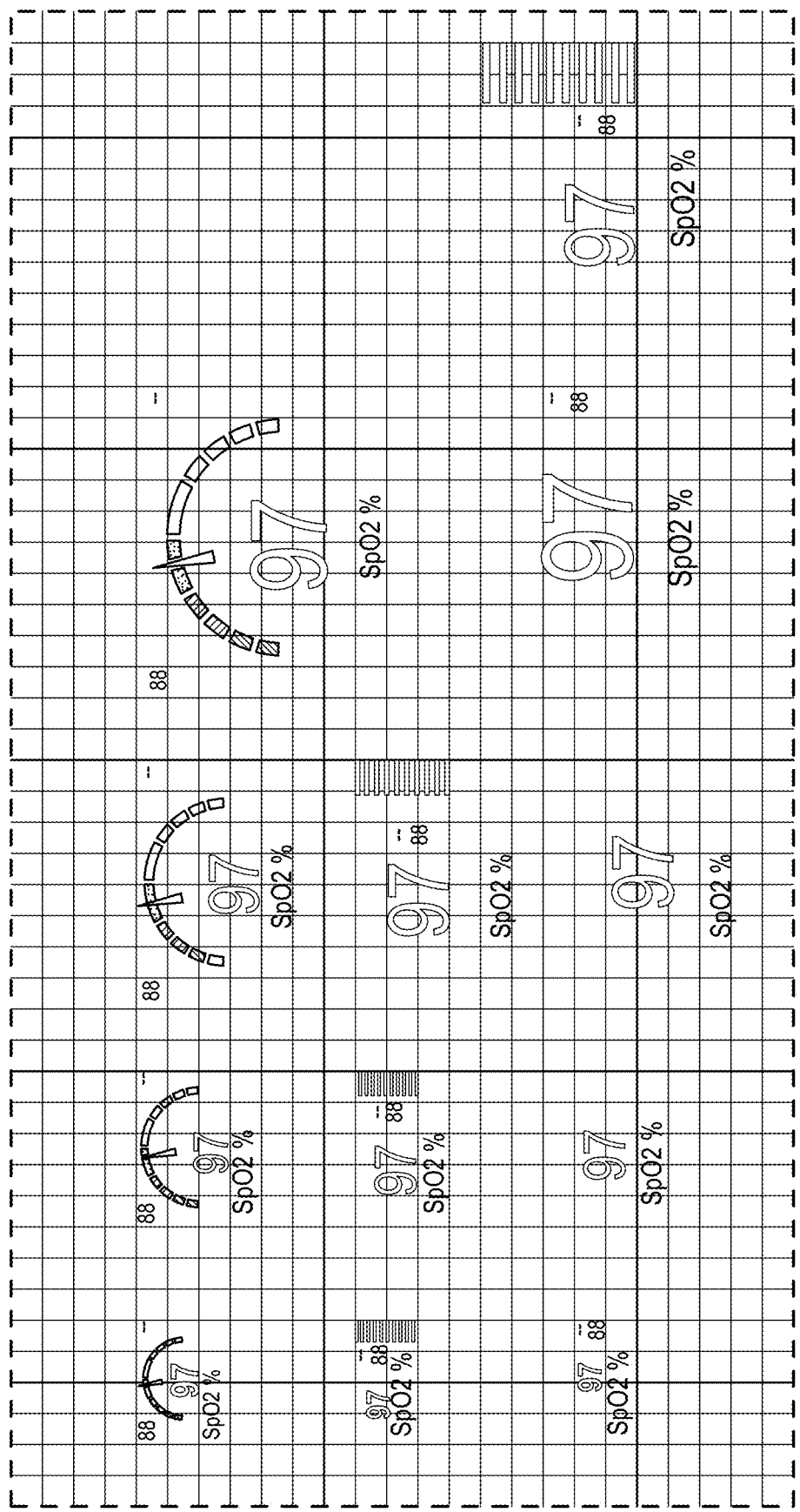
FIG. 48 is a front view of a display screen or portion thereof with a graphical user interface in accordance with a twenty-first embodiment.
Figure 49:
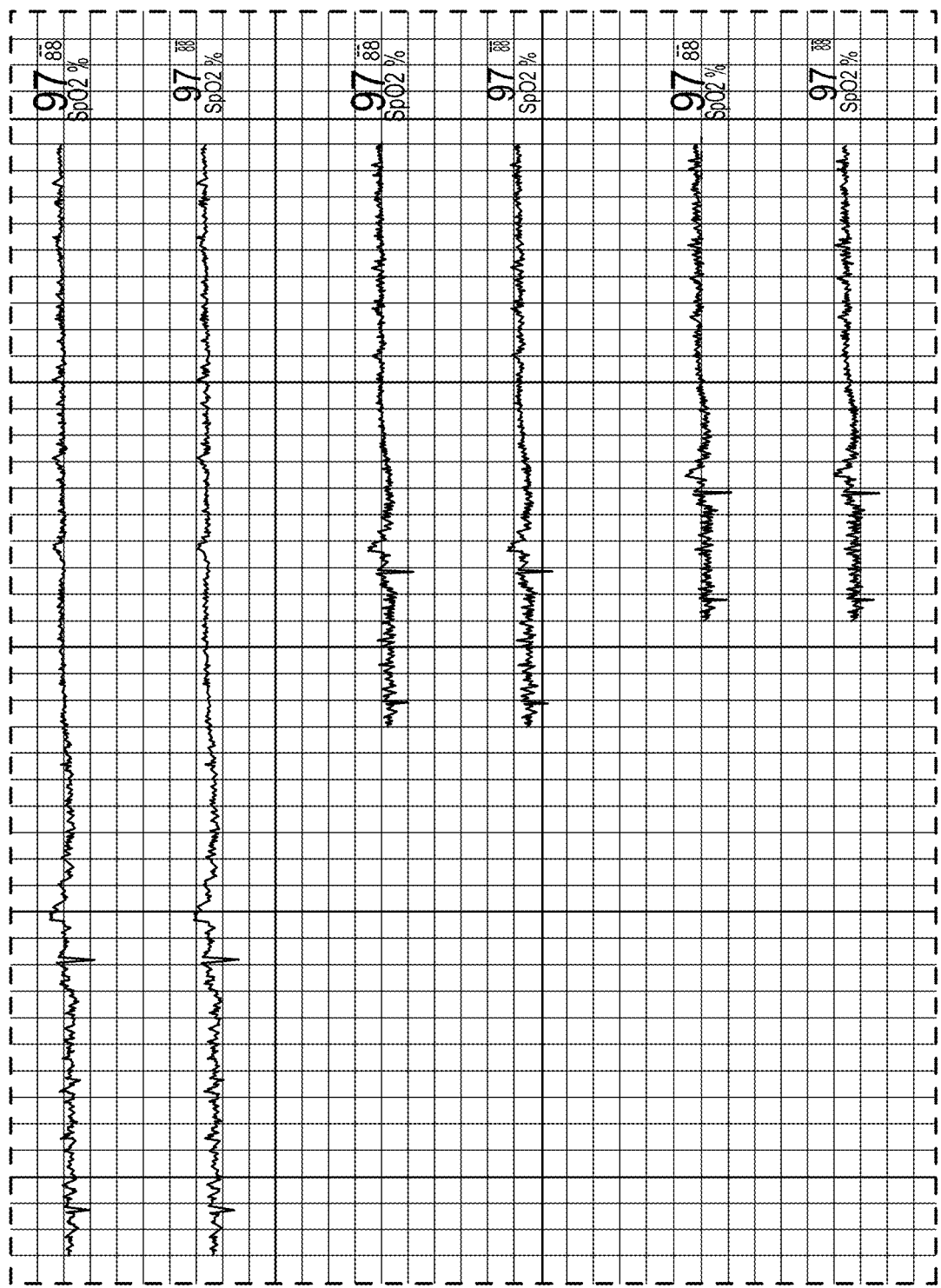
FIG. 49 is a front view of a display screen or portion thereof with a graphical user interface in accordance with a twenty-second embodiment.
Figure 50:
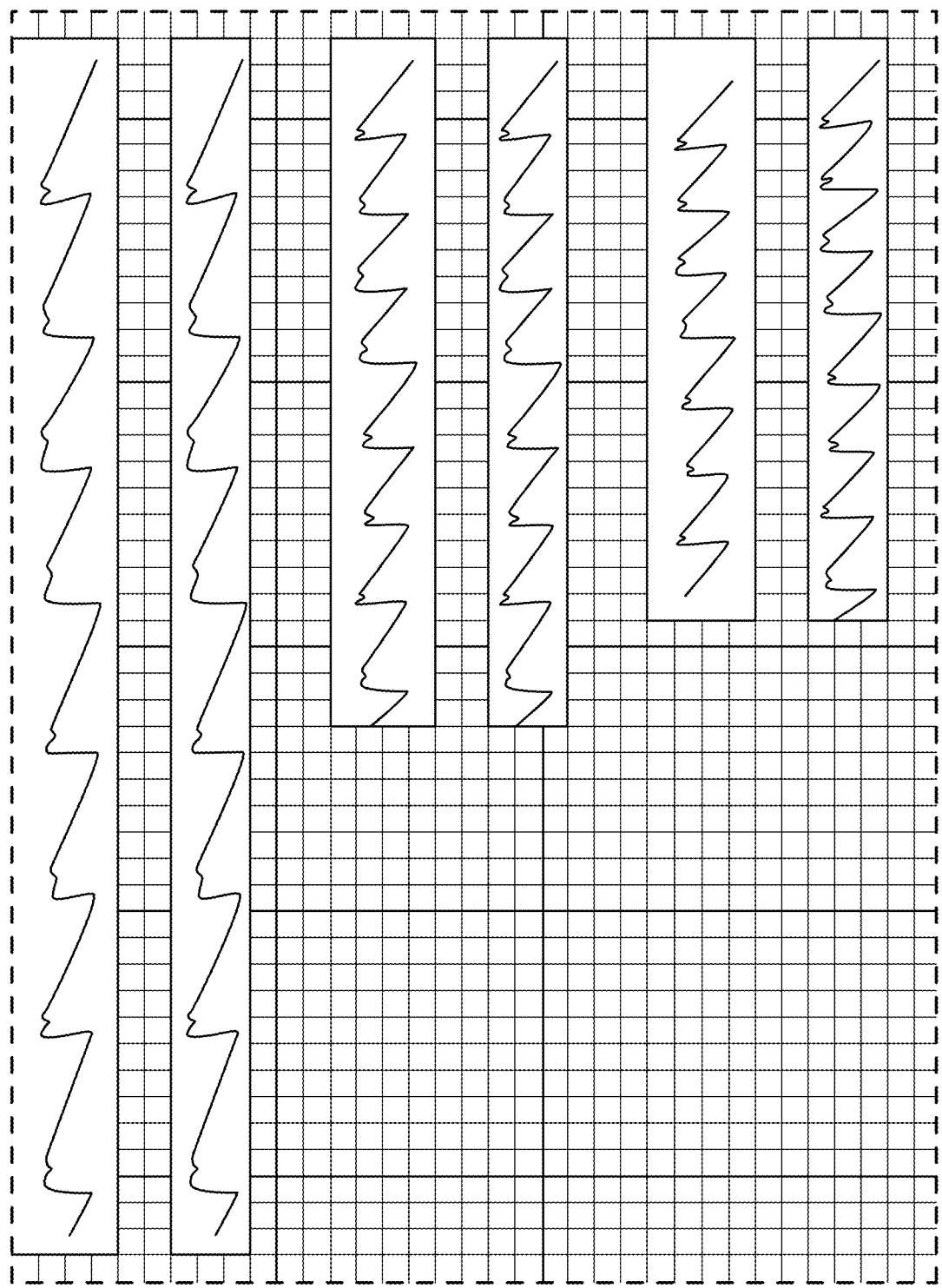
FIG. 50 is a front view of a display screen or portion thereof with a graphical user interface in accordance with a twenty-third embodiment.
Figure 51:
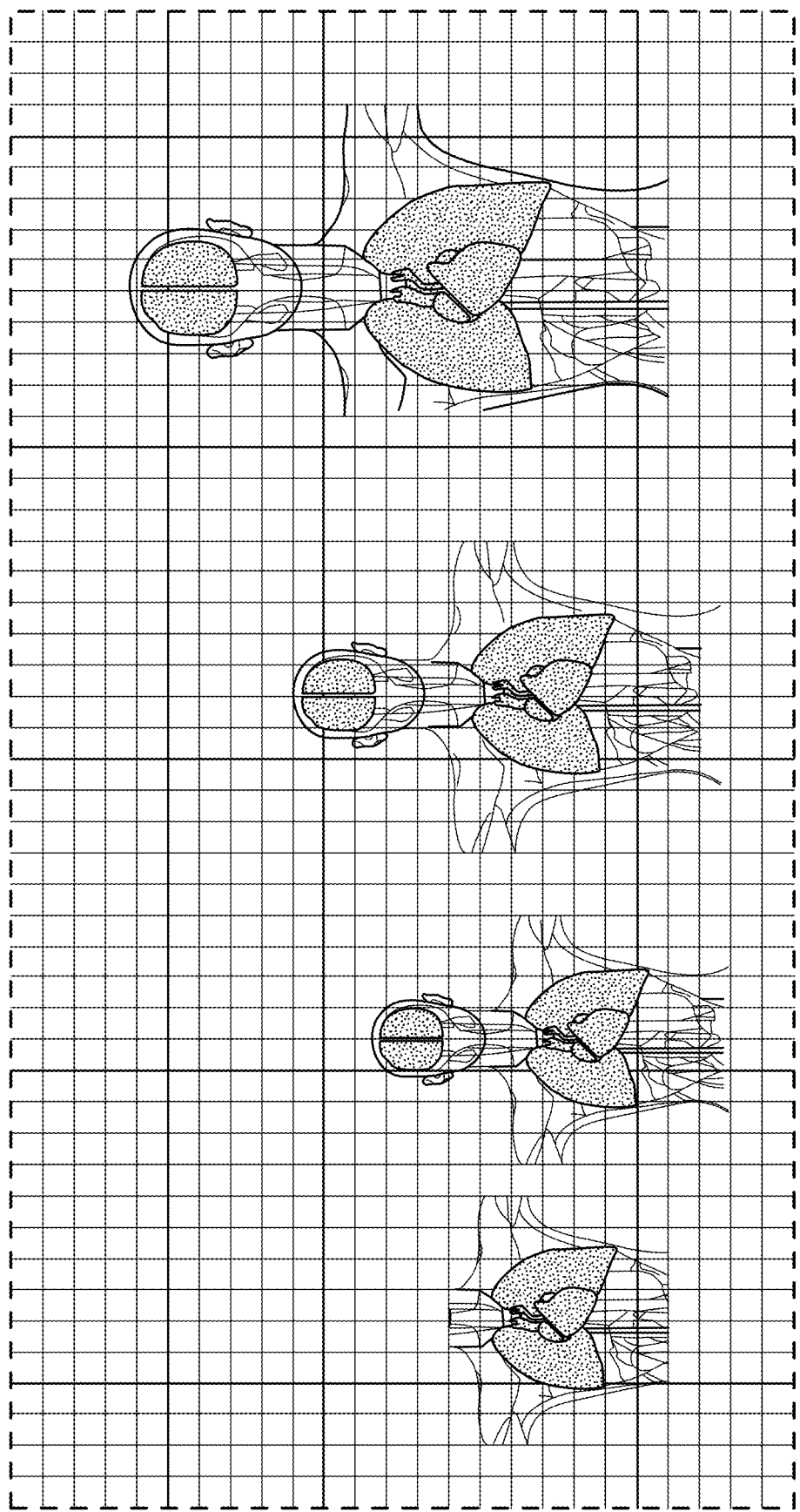
FIG. 51 is a front view of a display screen or portion thereof with a graphical user interface in accordance with a twenty-fourth embodiment.

FIG. 20 illustrates a layout saving screen 2000 for saving a configuration of a display of a host device, such as the display 476. The layout saving screen 2000 can include a layout name area 2002 where a user may input a template name (for example, "untitled layout 2018_05_18") for a custom layout that may be assigned and saved and then used to retrieve or share the custom layout. The custom layout can be saved locally to the host device or may be saved or shared with other devices, such as a server like the MMS 434 or a computer like the hub 100, and in turn used by the other devices to also share or similarly display measurement data.

FIGS. 21, 22, 23, 24, 25, 26, and 27 illustrate example templates for presenting information including measurement data as described herein. The different templates can be usable or desirable for different care conditions, use cases, or patient treatments. The different templates can moreover serve as a starting point for a user for constructing a layout and be further customized to include or exclude particular measurement data or interface controls or present data from different sources, in a revised priority or order, or with different formatting.

Design Embodiments

Figure 56:
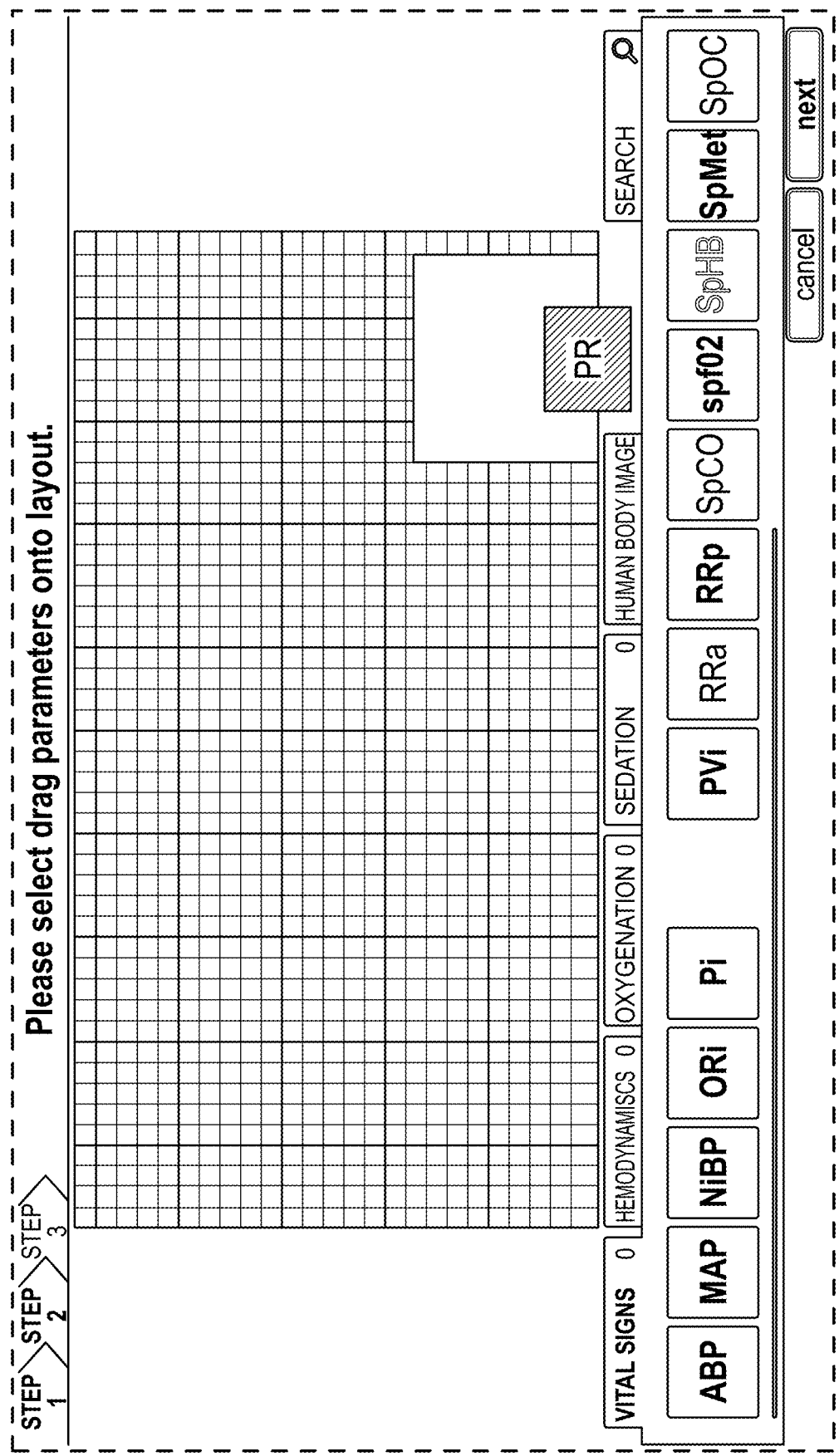
FIG. 56 is a front view of a display screen or portion thereof with a graphical user interface in accordance with a twenty-ninth embodiment.
Figure 57:
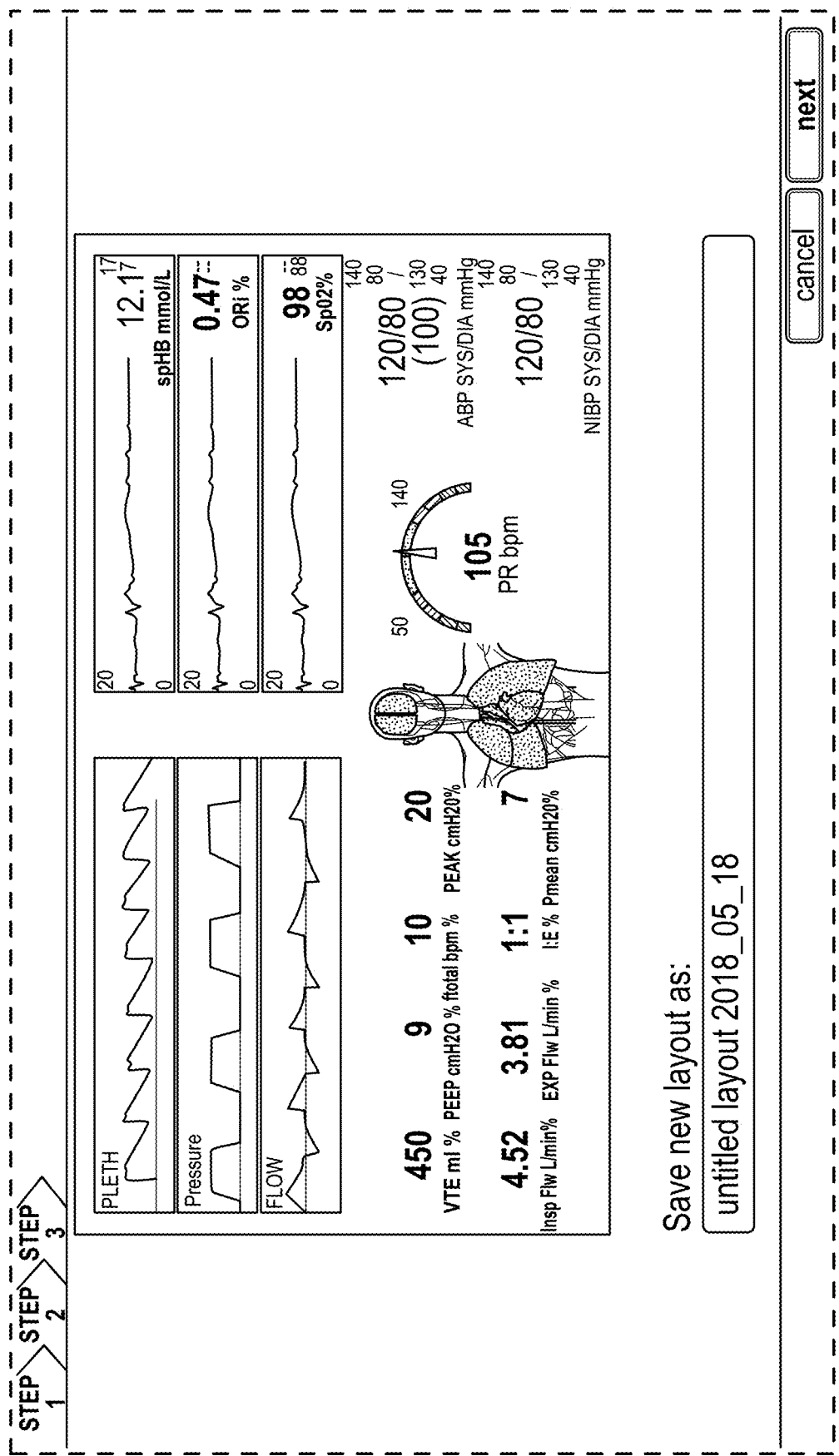
FIG. 57 is a front view of a display screen or portion thereof with a graphical user interface in accordance with a thirtieth embodiment.
Figure 58:
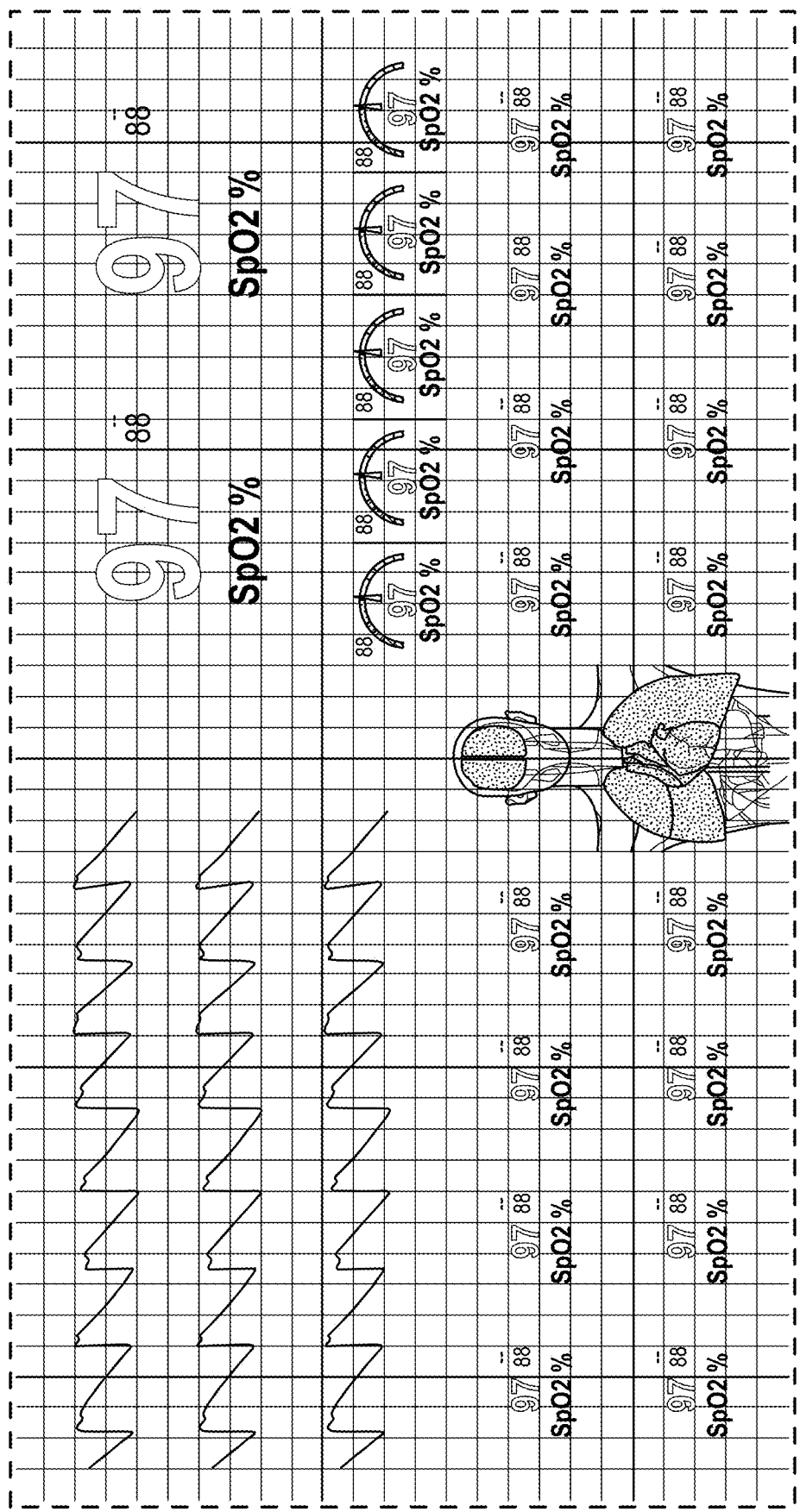
FIG. 58 is a front view of a display screen or portion thereof with a graphical user interface in accordance with a thirtieth-first embodiment.
Figure 59:
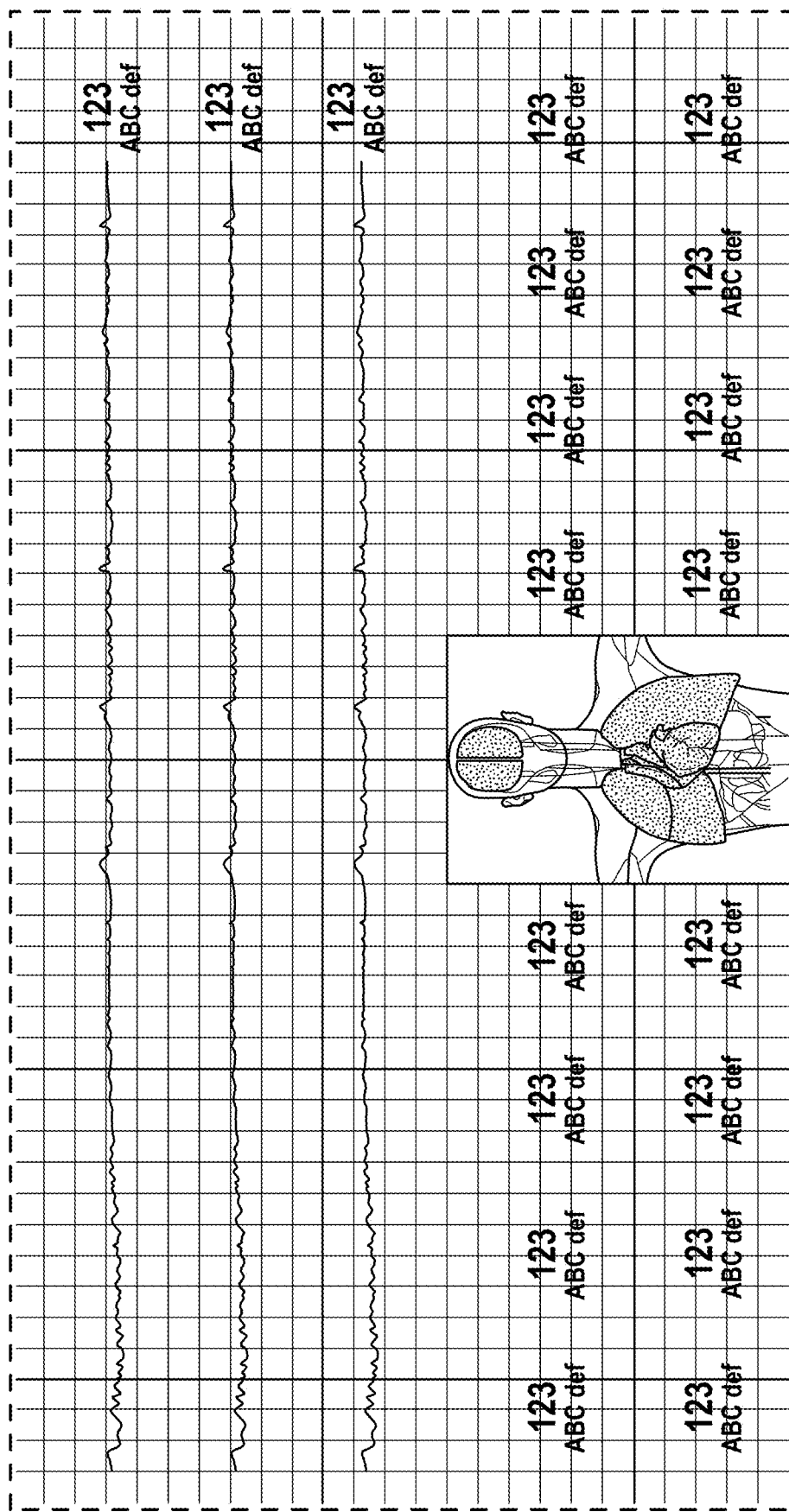
FIG. 59 is a front view of a display screen or portion thereof with a graphical user interface in accordance with a thirtieth-second embodiment.
Figure 60:
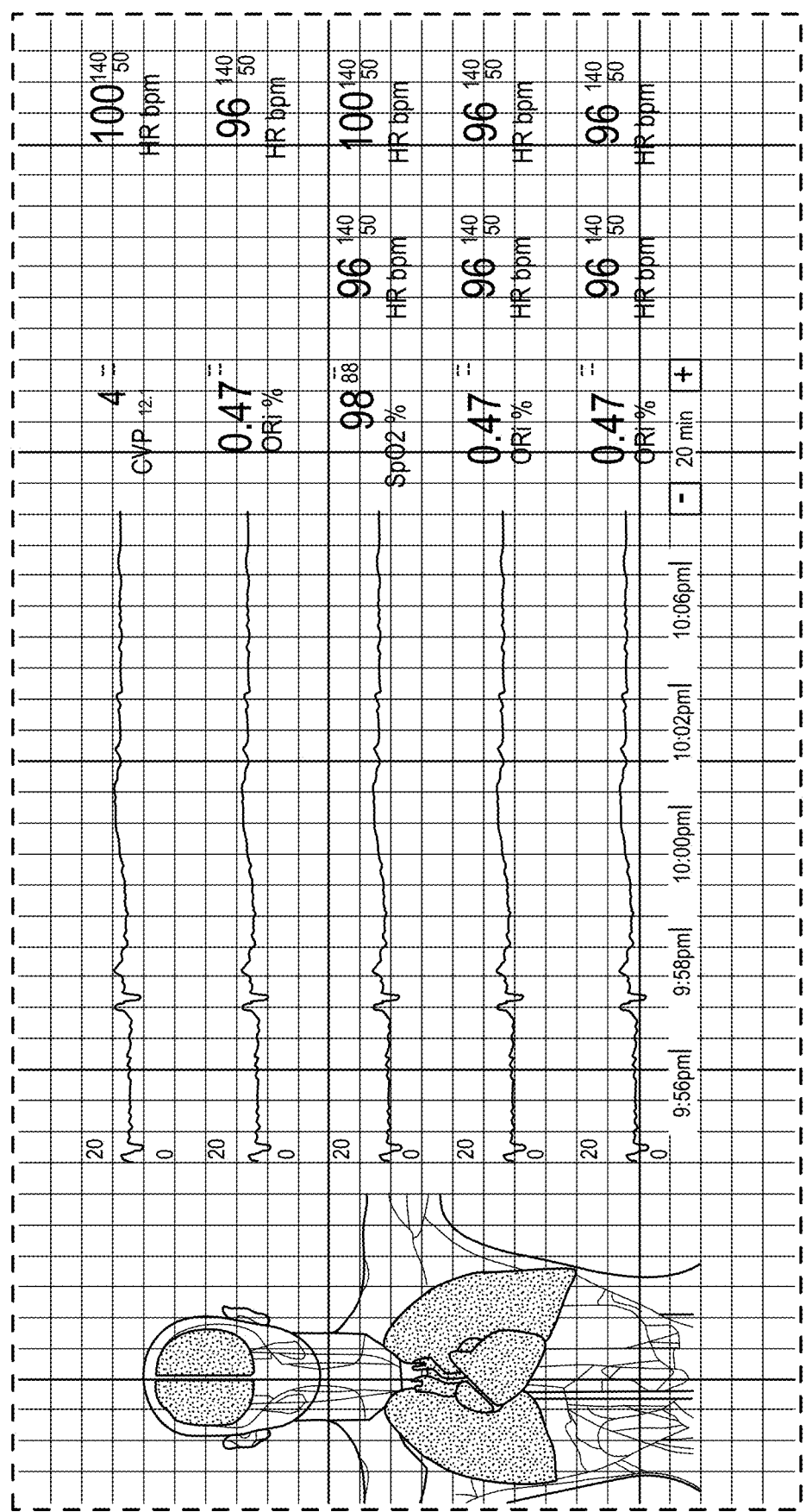
FIG. 60 is a front view of a display screen or portion thereof with a graphical user interface in accordance with a thirtieth-third embodiment.
Figure 61:
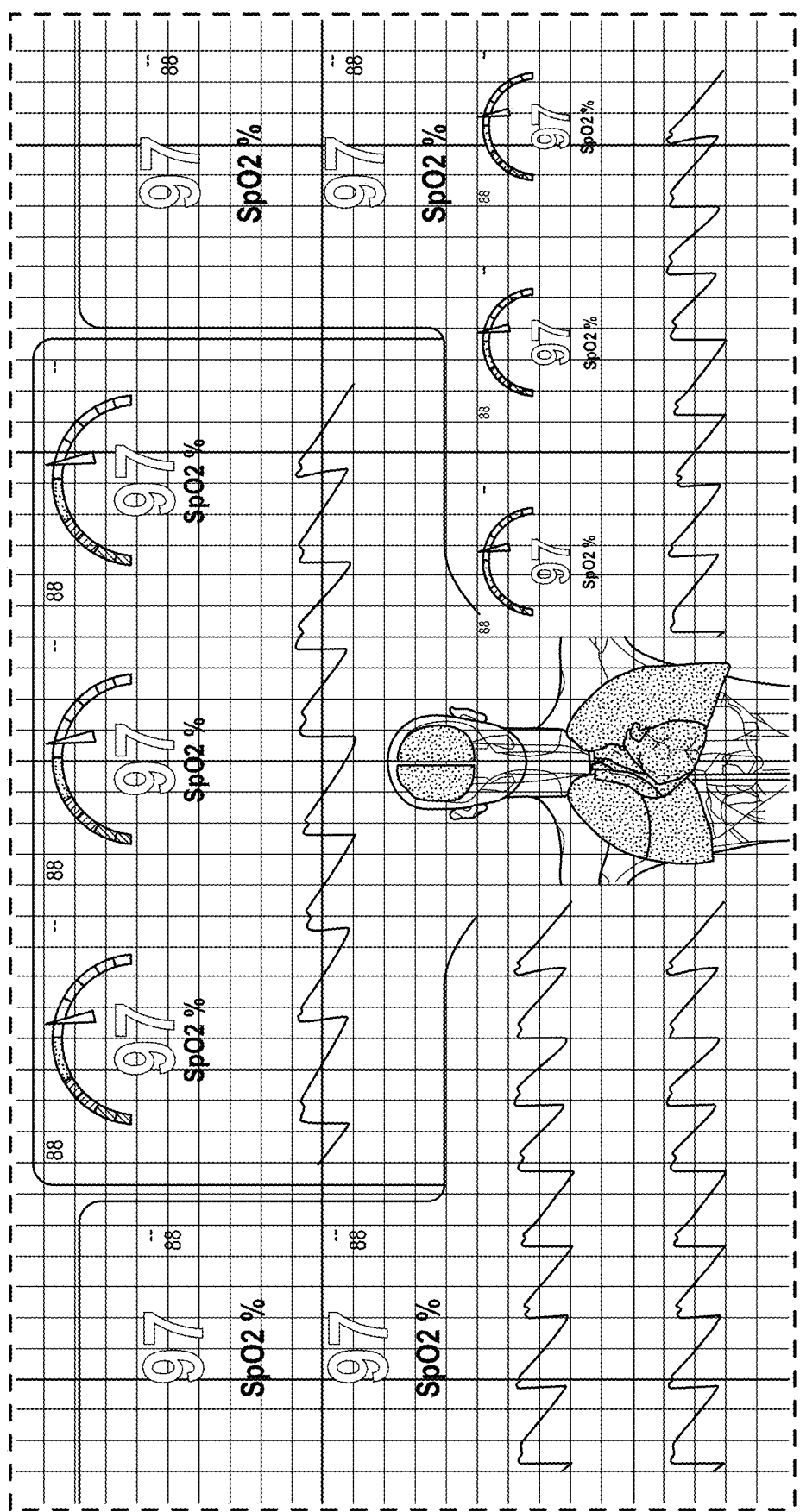
FIG. 61 is a front view of a display screen or portion thereof with a graphical user interface in accordance with a thirtieth-fourth embodiment.
Figure 62:
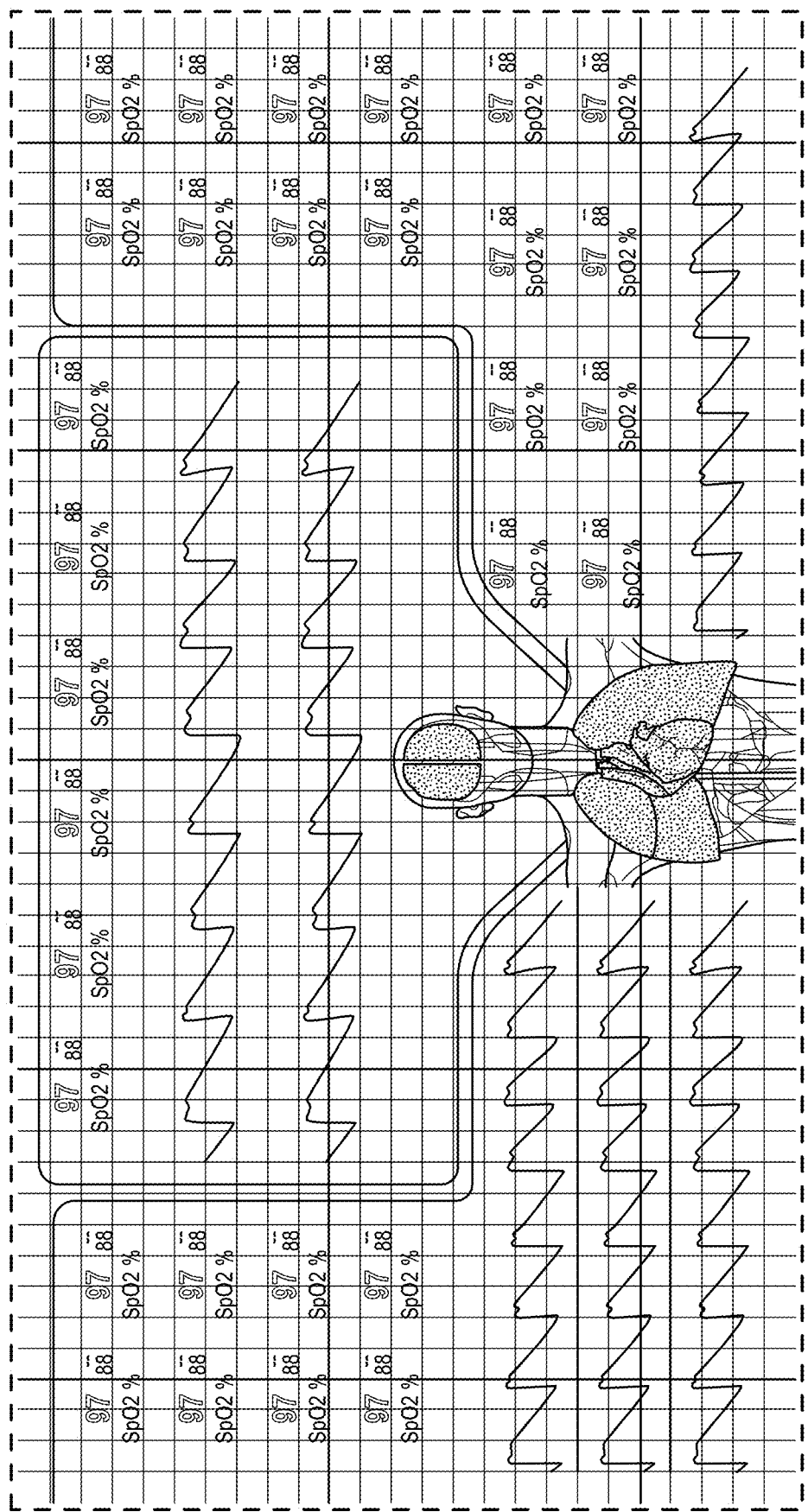
FIG. 62 is a front view of a display screen or portion thereof with a graphical user interface in accordance with a thirtieth-fifth embodiment.
Figure 63:
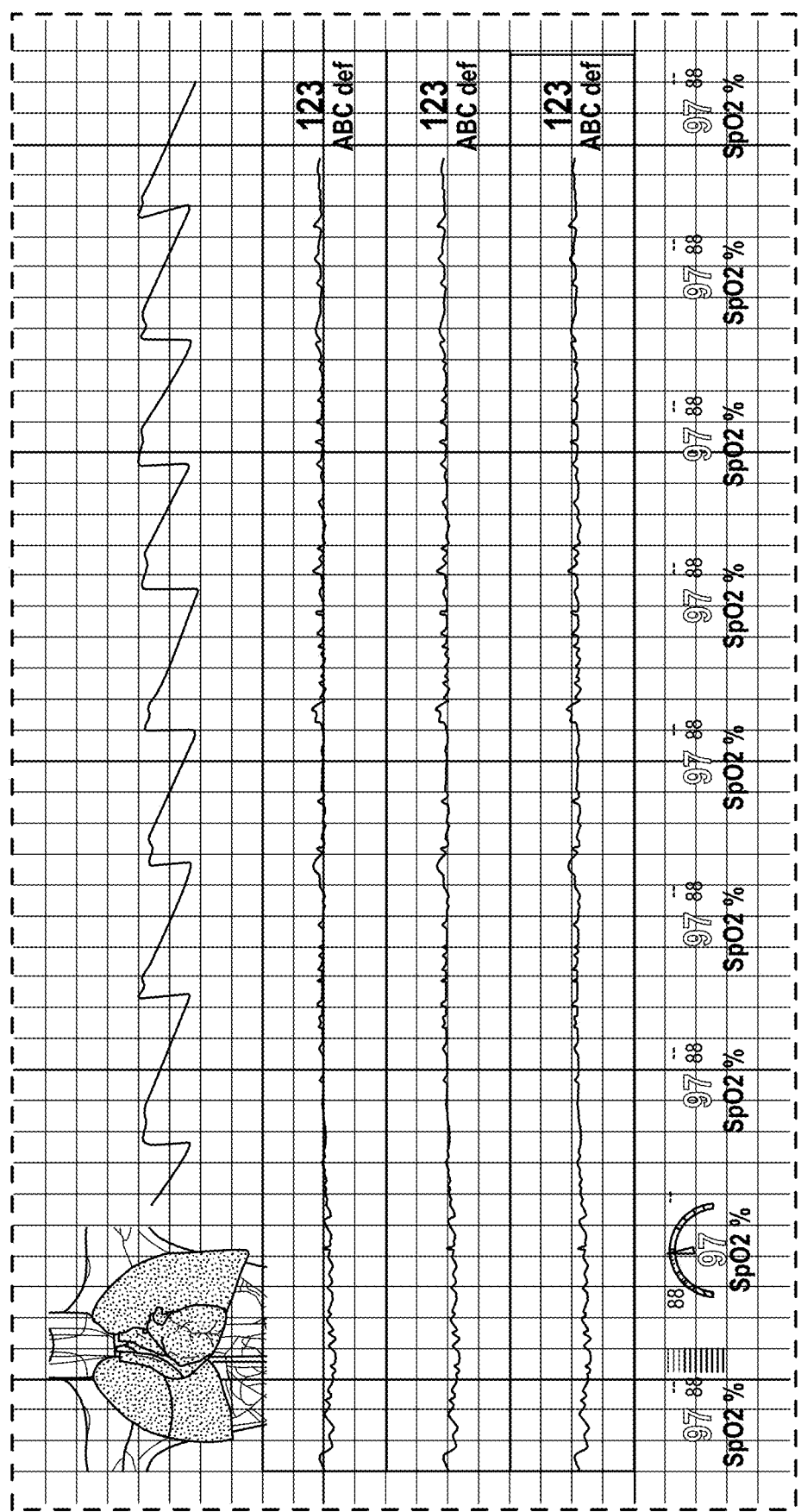
FIG. 63 is a front view of a display screen or portion thereof with a graphical user interface in accordance with a thirtieth-sixth embodiment.
Figure 64:
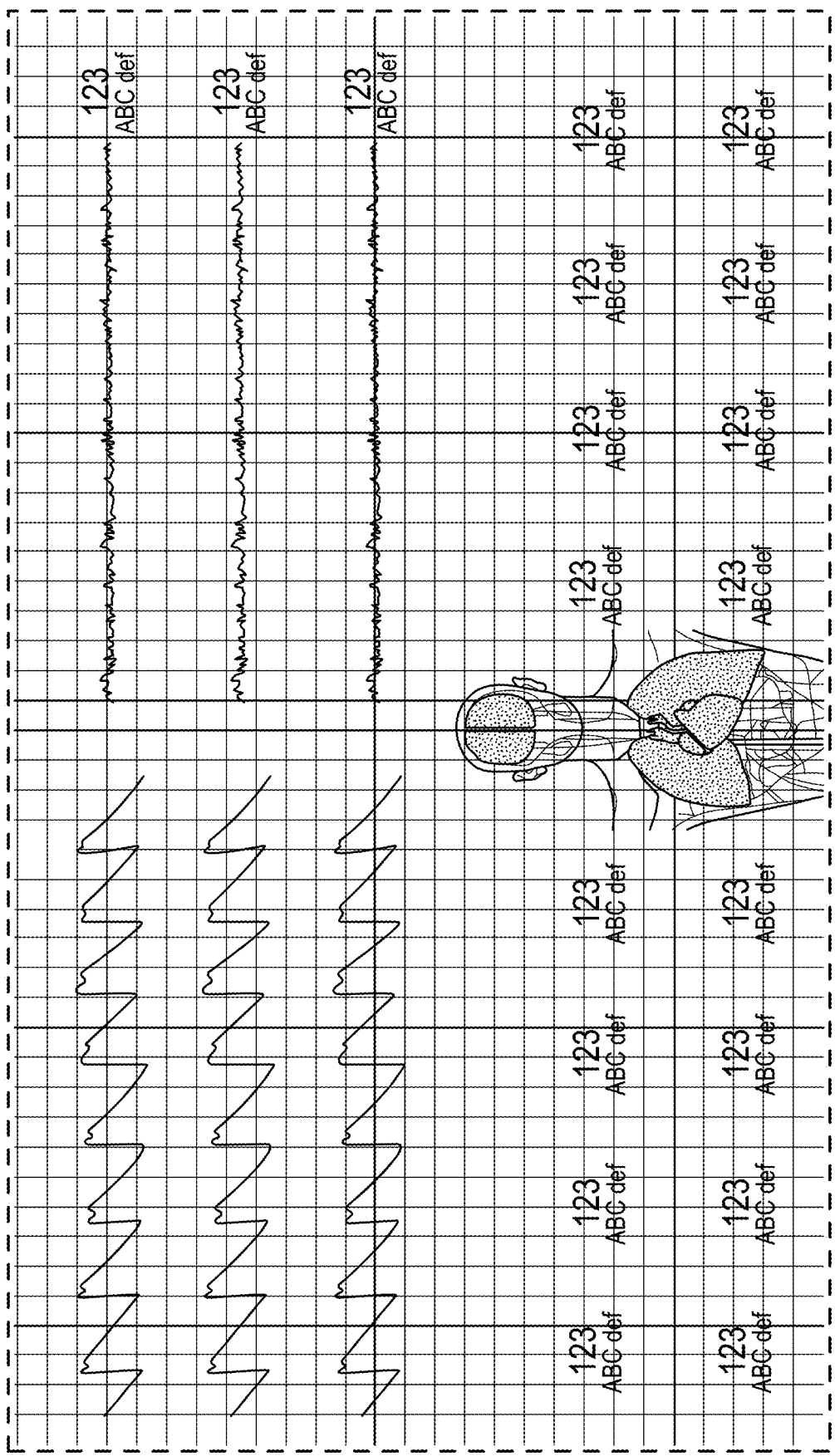
FIG. 64 is a front view of a display screen or portion thereof with a graphical user interface in accordance with a thirtieth-seventh embodiment.

FIGS. 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, and 64 illustrate example ornamental designs for a display screen or portion thereof with graphical user interface. The broken lines, including those showing a display screen or portion thereof and those depicting portions of a graphical user interface, do not form part of an ornamental design. The ornamental design for a display screen or portion thereof with a graphical user interface, shown in any of FIGS. 28-64, may be within a graphical user interface of a computer or monitor, such as those described herein. The pattern areas can depict areas of contrasting appearance. In FIG. 54, the different diagonal line pattern areas of the rectangle with the "PR" text and the rectangle without text and the non-pattern rectangle areas depict areas of contrasting appearance. In FIG. 56, the diagonal line pattern area of the rectangle with the "PR" text and the non-pattern rectangle areas depict areas of contrasting appearance.

Terminology

The term "plethysmograph" includes it ordinary broad meaning known in the art which includes data responsive to changes in volume within an organ or whole body (usually resulting from fluctuations in the amount of blood or air it contains).

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure. Although various specific parameter measurements are described herein, the specific parameter measurements may be merely illustrative of measurements that can be associated with various windows, sensors, or monitors. Additional or alternative specific parameter measurements may be used or provided.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, or microcode, and may refer to programs, routines, functions, classes, or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to claims.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Additionally, all publications, patents, and patent applications mentioned in this specification are herein incorporated by reference to the same extent as if each individual publication, patent, or patent application was specifically and individually indicated to be incorporated by reference.

What is claimed:

1. An improved display method for providing real-time and time-critical physiological parameters to a plurality of clinicians in a surgical care setting, the improved display method comprising:

presenting, on a display, a plurality of template elements corresponding to a plurality of display templates, the plurality of display templates being configured to display measurement values for a plurality of physiological parameters being monitored for a patient, at least one of the plurality of display templates being configured to display the measurement values in different locations from another of the plurality of display templates;

receiving a first user selection of a selected template element of the plurality of template elements that corresponds to a selected display template of the plurality of display templates, the selected display template comprising (i) a parameter display slot and (ii) a trend or waveform display slot, wherein the parameter display slot is located at a first location within the selected display template, wherein the parameter display slot is not associated with a parameter element at a first time, wherein the trend or waveform display slot is located at a second location within the selected display template, and wherein the trend or waveform display slot is not associated with a trend display element or a waveform display element at the first time;

presenting a plurality of parameter elements together with the selected display template on the display, the plurality of parameter elements comprising a first parameter element and a second parameter element;

receiving, at a second time, second user selections of (i) the first parameter element from among the plurality of parameter elements and (ii) the parameter display slot;

in response to receiving the second user selections, populating the parameter display slot at the first location with a first physiological parameter of the plurality of physiological parameters corresponding to the first parameter element;

receiving, at a third time, third user selections of (i) the second parameter element from among the plurality of parameter elements and (ii) the trend or waveform display slot; and in response to receiving the third user selections, populating the trend or waveform display slot at the second location with a second physiological parameter of the plurality of physiological parameters corresponding to the second parameter element.

2. The improved display method of claim 1, wherein the first physiological parameter comprises a pulse rate, and the second physiological parameter comprises an oxygen saturation.

3. The improved display method of claim 1, further comprising, responsive to a fourth user selection of a color change element, adjusting a color for displaying the measurement values for the first physiological parameter with the parameter display slot on the display.

4. A medical monitoring device configured to customize a display of measurements of physiological parameters monitored for a patient, the medical monitoring device comprising:

a memory device configured to store a screen layout; and
one or more processors configured to:

output the screen layout and a plurality of parameter display slots for presentation together on a display, the plurality of parameter display slots comprising a first parameter display slot and a second parameter display slot, wherein each slot of the first parameter display slot and the second parameter display slot are not associated with a parameter element at a first time, wherein the first parameter display slot is located at a first location within the screen layout, and wherein the second parameter display slot is located at a second location within the screen layout, output a plurality of parameter elements together with the screen layout on the display, the plurality of parameter elements comprising a first parameter element and a second parameter element, receive, at a second time, a first user input selecting (i) the first parameter element from among the plurality of parameter elements and (ii) the first parameter display slot, receive, at a third time, a second user input selecting (i) the second parameter element from among the plurality of parameter elements and (ii) the second parameter display slot, in response to receiving the first user input, populate the first parameter display slot at the first location on the screen layout with measurement values for a first physiological parameter, and in response to receiving the second user input, populate the second parameter display slot at the second location on the screen layout with measurement values for a second physiological parameter.

5. The medical monitoring device of claim 4, wherein the first user input comprises a drag and drop action, the drag and drop action comprising (i) a selection action indicating the first parameter element and (ii) a release action proximate to the first location.

6. The medical monitoring device of claim 4, wherein the first parameter element comprises a first identifier indicative of the first physiological parameter.

7. The medical monitoring device of claim 6, wherein the first identifier comprises an abbreviation for the first physiological parameter.

8. The medical monitoring device of claim 4, wherein the first parameter element comprises a numerical value configured to present the measurement values for the first physiological parameter.

9. The medical monitoring device of claim 8, wherein the second parameter display slot comprises a trend or a waveform.

10. The medical monitoring device of claim 4, wherein the first parameter display slot is a different size on the display from the second parameter display slot.

11. The medical monitoring device of claim 4, wherein the first physiological parameter comprises a pulse rate, and the second physiological parameter comprises a respiration rate.

12. The medical monitoring device of claim 4, wherein the one or more processors is configured to update the first parameter display slot and the second parameter display slot on the display to reflect changes in real time in the measurement values for the first physiological parameter and the measurement values for the second physiological parameter.

13. The medical monitoring device of claim 4, wherein the one or more processors is configured to transition between (i) a configuration mode in which the first parameter display slot is movable on the screen layout and (ii) an operation mode in which the first parameter display slot is not movable on the screen layout.

14. The medical monitoring device of claim 4, wherein the one or more processors is configured to limit areas in which the first parameter display slot is permitted to be assigned on the screen layout.

15. The medical monitoring device of claim 4, wherein the one or more processors is configured to:
   for a first period of time, update the first parameter display slot on the display to reflect changes in real time in the measurement values for the first physiological parameter determined from a first sensor, and
   for a second period of time, update the first parameter display slot on the display to reflect changes in real time in the measurement values for the first physiological parameter determined from a second sensor different from the first sensor.

16. The medical monitoring device of claim 15, wherein the one or more processors is configured to transition from the first period of time to the second period of time responsive to a connection of the second sensor to a patient monitor.

17. The medical monitoring device of claim 4, wherein the one or more processors is configured to transition from a configuration mode to an operation mode.

18. The medical monitoring device of claim 17, wherein the one or more processors is configured to transition from the operation mode to the configuration mode.

19. The medical monitoring device of claim 4, wherein the one or more processors is configured to output the screen layout for presentation in a first area of the display and the plurality of parameter elements for presentation in a second area of the display different from the first area.

20. The medical monitoring device of claim 4, wherein the one or more processors is configured to:
   receive alphanumeric characters as a third user input, and
   assign the alphanumeric characters to be a name for the screen layout.

* * * * *